United States Patent [19]

Rorer

[11] Patent Number: 4,511,392
[45] Date of Patent: Apr. 16, 1985

[54] HERBICIDAL SULFONAMIDES
[75] Inventor: Morris P. Rorer, Newark, Del.
[73] Assignee: E. I. Du Pont de Nemours and Company, Wilmington, Del.
[21] Appl. No.: 436,631
[22] Filed: Oct. 29, 1982

Related U.S. Application Data

[63] Continuation-in-part of Ser. No. 337,934, Jan. 7, 1982, abandoned.
[51] Int. Cl.³ .................. C07D 403/10; A01N 90/12
[52] U.S. Cl. .......................................... 71/90; 71/91; 71/92; 71/93; 544/209; 544/253; 544/212; 544/278; 544/321; 544/324; 544/331
[58] Field of Search ............... 71/90, 92, 91; 544/321, 544/324, 331

[56] References Cited

U.S. PATENT DOCUMENTS 4,214,890 7/1980 Levitt .................................. 544/321
4,238,621 12/1980 Levitt .................................. 544/321

Primary Examiner—Glennon H. Hollrah
Assistant Examiner—James H. Turnipseed

[57] ABSTRACT

This invention relates to ortho-(isoxazolyl, isothiazolyl, pyrazolyl, thiadiazolyl, oxadiazolyl, and triazolyl)benzenesulfonamides and their use as herbicides.

39 Claims, No Drawings

HERBICIDAL SULFONAMIDES

RELATED APPLICATION

This application is a continuation-in-part of my co-pending application U.S. Ser. No. 337,934, filed Jan. 7, 1982 now abandoned.

BACKGROUND OF THE INVENTION

This invention relates to ortho-heterocyclicbenzenesulfonamides and, more particularly, to ortho-(isoxazol-3, or 4-, or 5-yl)benzenesulfonamides, ortho-(isothiazol-3, or 4-, or 5-yl)benzenesulfonamides, ortho-(1H-pyrazol-1, or 3-, or 4-, or 5-yl)benzenesulfonamides, ortho-(1,3,4-oxadiazol-2-yl)benzenesulfonamides, ortho-(1,2,4-oxadiazol-3, or 5-yl)benzenesulfonamides, ortho-(1,2,5-oxadiazol-3-yl)benzenesulfonamides, ortho-(1,3,4-thiadiazol-2-yl)benzenesulfonamides, ortho-(1,2,4-thiadiazol-3-, or 5-yl)benzenesulfonamides, ortho-(1,2,5-thiadiazol-3-yl)benzenesulfonamides, ortho-(1,2,3-thiadiazol-4-, or 5-yl)benzenesulfonamides, ortho-(1H-1,3,4-triazol-1-, or 2-yl)benzenesulfonamides, ortho-(1H-1-methyl-1,2,4-triazol-3-, or 5-yl)benzenesulfonamides, or ortho-(1H-1,2,4-triazol-1-yl)benzenesulfonamides and their use in agriculturally suitable compositions as pre-emergence and/or post-emergence herbicides and as plant growth regulants.

DESCRIPTION OF THE PRIOR ART

U.S. Pat. Nos. 4,127,405 and 4,169,719 disclose herbicidal methoxymethylpyrimidine sulfonylurea compounds of the type which contain a —CH$_2$OCH$_3$ heterocyclic substituent.

European Patent Application No. 7687 discloses herbicidal sulfonylurea compounds such as, among others, where X is CH$_3$ or OCH$_3$;

Z is CH or N; and

Y is C$_1$-C$_4$ alkyl substituted with OCH$_3$, OC$_2$H$_5$, CN, C(O)L, or 1-3 atoms of F, Cl, or Br, where L is NH$_2$, OH, N(OCH$_3$)CH$_3$, NH(C$_1$-C$_4$ alkyl), N(C$_1$-C$_4$ alkyl) or C$_1$-C$_6$ alkoxy.

U.S. Pat. No. 4,378,991, issued Apr. 5, 1983 discloses herbicidal o-phenylbenzenesulfonylureas.

SUMMARY OF THE INVENTION

This invention relates to ortho-(heterocyclic)benzenesulfonamides of Formula I and to their agriculturally suitable salts, agricultural compositions containing them as an active ingredient, and to their method of use as general or selective pre-emergence and/or post-emergence herbicides and as plant growth regulants.

W″ is O or S;
W is O, S or NR;
W′ is O or S;
R is H or C$_1$-C$_4$ alkyl;
R$_1$ is H, F, Cl, Br, CH$_3$, CF$_3$ or OCH$_3$;
R$_2$ is H, CH$_3$, C$_2$H$_5$, Cl or Br;
R$_3$ is H, CH$_3$, C$_2$H$_5$, Cl, Br, OCH$_3$, OC$_2$H$_5$ or SCH$_3$;
R$_4$ is H or C$_1$-C$_4$ alkyl;
R$_5$ is H, CH$_3$, C$_2$H$_5$, Cl, Br, OCH$_3$, OC$_2$H$_5$ or SCH$_3$;
R$_6$ is H, CH$_3$ or C$_2$H$_5$;
R$_7$ is H or C$_1$-C$_4$ alkyl;
R$_{12}$ is H or CH$_3$;
R$_{12}$' is H or CH$_3$;
R$_{13}$ is H or CH$_3$;
R$_{14}$ is H, CH$_3$, C$_2$H$_5$, Cl, OCH$_3$, OC$_2$H$_5$ or SCH$_3$;
R$_{15}$ is C$_1$-C$_3$ alkyl;

X is CH$_3$, OCH$_3$ or Cl;

-continued

Y is $CH_3$, $C_2H_5$, $CH_2OCH_3$, $OCH_3$, $OC_2H_5$, $CH(OCH_3)_2$, $NH_2$, $NHCH_3$, $N(CH_3)_2$, $OCH_2CH_2OCH_3$, $OCH_2CF_3$, $SCH_3$, $CF_3$ or 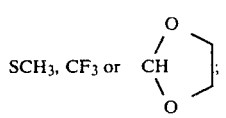;

Z is CH or N;
$X_1$ is $CH_3$, $OCH_3$ or Cl;
G is O or $CH_2$;
$X_2$ is $C_1$–$C_3$ alkyl or $CH_2CF_3$;
$Y_2$ is $CH_3O$, $C_2H_5O$, $CH_3S$ or $C_2H_5S$;

and their agriculturally suitable salts; provided that (a) when $R_2$ is Cl or Br, then W is O or S;

(b) when X is Cl, then Z is CH and Y is $OCH_3$, $OC_2H_5$, $NH_2$, $NHCH_3$ or $N(CH_3)_2$;

(c) when W" is S, then $R_{13}$ is H, A is

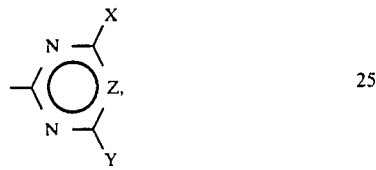

and Y is $CH_3$, $OCH_3$, $C_2H_5$, $OC_2H_5$, $CH_2OCH_3$, $CH(OCH_3)_2$ or

(d) when Q is

then one of $R_2$ or $R_3$ must be H, $CH_3$ or $C_2H_5$;

(e) when Q is

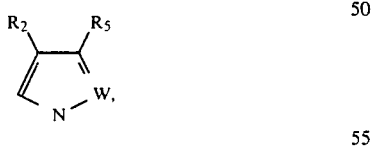

then one of $R_2$ or $R_5$ must be H, $CH_3$ or $C_2H_5$;

(f) the total number of carbon atoms of Q must be less than or equal to 8.

Preferred for their higher herbicidal activity and/or their more favorable ease of synthesis are:

(1) Compounds of Formula I where R and $R_{15}$ are independently $CH_3$ or $C_2H_5$; $R_2$, $R_3$, $R_4$, $R_5$, $R_6$, $R_7$ and $R_{14}$ are independently H or $CH_3$; and W" is O.

(2) Compounds of the Preferred (1) where $R_1$ and $R_{13}$ are H.

(3) Compounds of Preferred (2) where Y is $CH_3$, $CH_2OCH_3$, $OCH_3$, $OC_2H_5$,

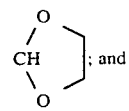; and

A is 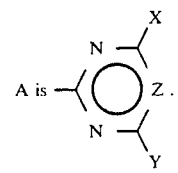.

(4) Compounds of preferred (3) where

Q is 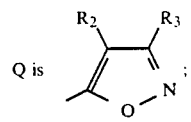;

(5) Compounds of preferred (3) where

Q is 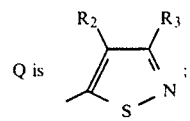;

(6) Compounds of preferred (3) where

Q is 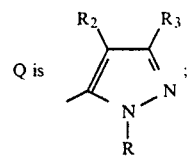;

(7) Compounds of preferred (3) where

Q is 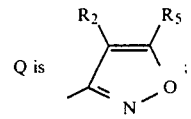;

(8) Compounds of preferred (3) where

Q is 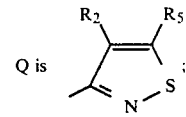;

(9) Compounds of preferred (3) where

Q is 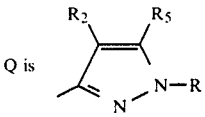;

(10) Compounds of preferred (3) where

Q is 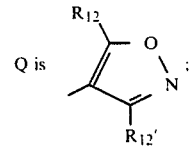;

(11) Compounds of preferred (3) where

-continued

Q is 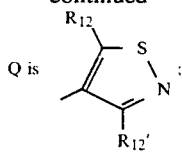

(12) Compounds of preferred (3) where

Q is 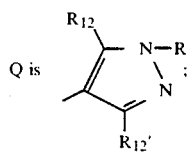

(13) Compounds of preferred (3) where

Q is 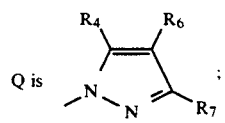

(14) Compounds of preferred (3) where

Q is 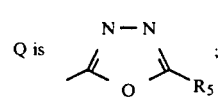

(15) Compounds of preferred (3) where

Q is 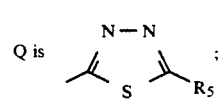

(16) Compounds of preferred (3) where

Q is 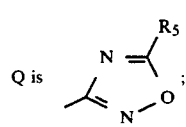

(17) Compounds of preferred (3) where

Q is 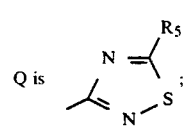

(18) Compounds of preferred (3) where

Q is 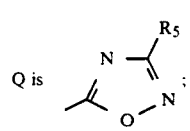

(19) Compounds of preferred (3) where

Q is 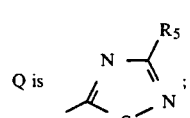

(20) Compounds of preferred (3) where

Q is 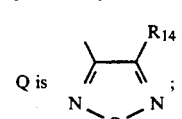

(21) Compounds of preferred (3) where

Q is 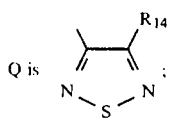

(22) Compounds of preferred (3) where

Q is 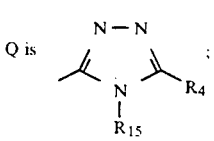

(23) Compounds of preferred (3) where

Q is 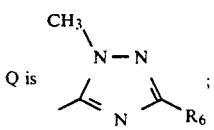

(24) Compounds of preferred (3) where

Q is 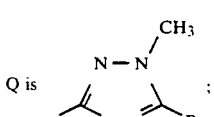

(25) Compounds of preferred (3) where

Q is 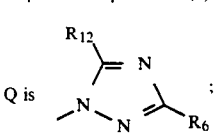

(26) Compounds of preferred (3) where

Q is 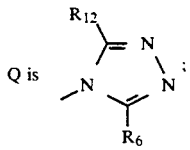

(27) Compounds of preferred (3) where

Q is 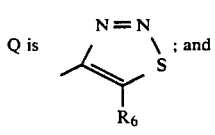; and

(28) Compounds of preferred (3) where

Q is 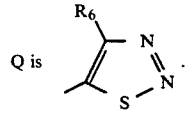

Specifically preferred are compounds of the broad scope selected from the group consisting of:
2-(isoxazol-5-yl)-N-[(4,6-dimethoxypyrimidin-2-yl)aminocarbonyl]benzenesulfonamide, m.p. 183°–187°;
2-(isoxazol-5-yl)-N-[(4-methoxy-6-methylpyrimidin-2-yl)aminocarbonyl]benzenesulfonamide, m.p. 185°–189°;

N-[(4,6-dimethoxypyrimidin-2-yl)aminocarbonyl]-2-(1-
 and/or 2-methyl-1H-pyrazol-3-yl)benzenesulfona-
 mide, m.p. 210°–212°;
N-[(4-methoxy-6-methyl-1,3,5-triazin-2-yl)aminocar-
 bonyl]-2-(1- and/or 2-methyl-1H-pyrazol-3-yl)ben-
 zenesulfonamide, m.p. 200°–205°;
N-[(4,6-dimethoxypyrimidin-2-yl)aminocarbonyl]-2-(1-
 methyl-1H-pyrazol-4-yl)benzenesulfonamide, m.p.
 220°–226°;
N-[(4-methoxy-6-methyl-1,3,5-triazin-2-yl)aminocar-
 bonyl]-2-(1-methyl-1H-pyrazol-4-yl)benzenesulfona-
 mide, m.p. 221°–224°;
N-[(4,6-dimethoxypyrimidin-2-yl)aminocarbonyl]-2-
 (isoxazol-4-yl)benzenesulfonamide, m.p. 175°–178°;
2-(isoxazol-4-yl)-N-[(4-methoxy-6-methylpyrimidin-2-
 yl)aminocarbonyl]benzenesulfonamide, m.p.
 181°–185°; and
2-(isoxazol-4-yl)-N-[(4-methoxy-6-methyl-1,3,5-triazin-
 2-yl)aminocarbonyl]benzenesulfonamide, m.p.
 178°–181°.

DETAILED DESCRIPTION OF THE INVENTION

Synthesis

The compounds of Formula (I) can be prepared by one or more of the methods described below in Equations 1 to 3a.

As shown in Equation 1 below, compounds of Formula (I), where W''' is O, can be prepared by reacting a sulfonamide of Formula (II) with an appropriate methyl carbamate of Formula (III) in the presence of an equimolar amount of trimethylaluminum, wherein $R_1$, $R_{13}$, Q and A are as previously defined.

Equation 1

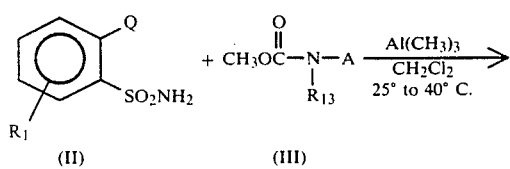

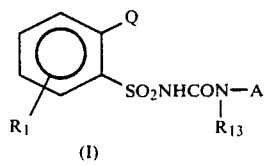

The reaction of Equation 1 is best run in methylene chloride at about 25° to 40° C. for 10 to 96 hours under a nitrogen atmosphere. The product can be isolated by addition of an aqueous acetic acid solution followed by extraction of the product into methylene chloride, or by filtration of a product of low solubility. The product can be purified by trituration with solvents such as 1-chlorobutane, ethyl acetate or ethyl ether or by column chromatography on silica gel.

As shown in Equation 1a, many compounds of Formula (I), where W''' is O, can also be prepared by reacting a sulfonylcarbamate of Formula (IIa) with an appropriate amine of Formula (VII).

Equation 1a

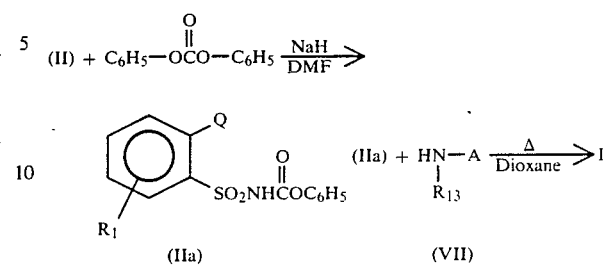

wherein $R_1$, $R_{13}$, A and Q are as defined above; except $R_3$ and $R_{14}$ are H or $C_1$–$C_2$ alkyl, $R_5$ is $C_1$–$C_2$ alkyl, and R is $C_1$–$C_4$ alkyl.

The reaction is carried out at 50°–100° C. in a solvent such as dioxane for 0.5 to 24 hours as taught in EPO Publication No. 44807. The required carbamates IIa are prepared by reacting the corresponding sulfonamide II with diphenylcarbonate in the presence of a strong base.

Some of the compounds of Formula (I) can also be prepared as shown in Equation 2 below.

Equation 2

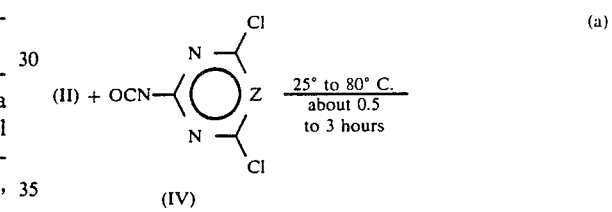

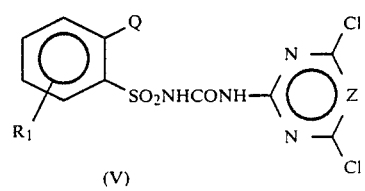

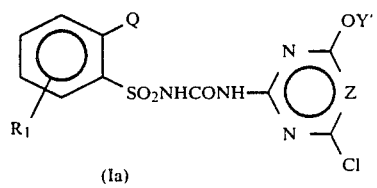

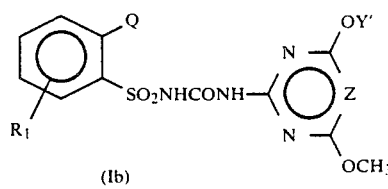

-continued

Equation 2

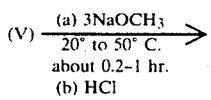

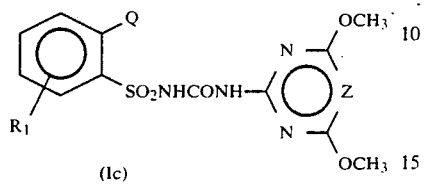

wherein Y' is CH$_3$ or C$_2$H$_5$ and R$_1$, Q and Z are as originally defined, except R$_3$ and R$_5$ are not Cl or Br and R$_{14}$ is not Cl.

The reactions of Equation 2 are run according to similar procedures taught in European Patent 30,140. Thus, in reaction 2a, a sulfonamide of Formula (II) is reacted with a dichloropyrimidinyl isocyanate or dichlorotriazinyl isocyanate of Formula (IV) in an inert solvent such as acetonitrile at reflux for 0.5 to 3 hours to form a sulfonylurea of Formula (V). The product is isolated by filtration. In reaction 2b, V is reacted with two mole equivalents of sodium methoxide or sodium ethoxide in tetrahydrofuran at 0° to 25° C. for about one hour, followed by acidification with hydrochloric acid to a pH of about 1, to form a sulfonylurea of Formula (Ia). The product is isolated by filtration. In reaction 2c, Ia is reacted with two mole equivalents of sodium methoxide in methanol at 25° to about 50° C. for about 1 hour, followed by acidification with hydrochloric acid to a pH of about 1, to form a sulfonylurea of Formula (Ib). Alternatively, as shown in reaction 2d, V can be reacted with at least three mole equivalents of sodium methoxide at 20° to 50° C. for about 1 hour, followed by acidification with hydrochloric acid to a pH of about 1, to provide Ic directly, where Y' of Ib is OCH$_3$. The products of reactions 2c and 2d are isolated by addition of water and filtration.

The heterocyclic isocyanates of Formula (IV) in Equation 2 above can be prepared by methods described in Swiss 579,062, U.S. Pat. Nos. 3,919,228, 3,732,223 and *Angew Chem. Int. Ed.*, 10, 402 (1976), the disclosures of which are herein incorporated by reference.

As shown in Equation 3 below, some of the compounds of Formula (I), where W''' is O, can also be prepared by reacting a sulfonyl isocyanate of Formula (VI) with an amine of Formula (VII).

Equation 3

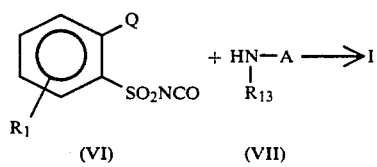

wherein R$_1$, R$_{13}$, Q and A are as originally defined.

The reaction of Equation 3 above can best be carried out in an inert, aprotic, organic solvent such as methylene chloride, tetrahydrofuran or acetonitrile at ambient pressure and temperature. The mode of addition is not critical; however, it is often convenient to add the sulfonyl isocyanate to a stirred suspension of amine VII. The reaction is generally exothermic. In some cases, the desired product is insoluble in the warm reaction medium and crystallizes from it in pure form. Products soluble in the reaction medium are isolated by evaporation of the solvent, trituration of the solid residues with solvents such as 1-chlorobutane, ethyl ether, ethyl acetate or pentane and filtration. Impure products may be purified by column chromatography on silica gel.

Many of the intermediate sulfonyl isocyanates of Formula (VI) in Equation 3 above can be prepared, although often times in low yields, from sulfonamides by methods described in U.S. Pat. No. 4,238,621. The method requires reacting sulfonamides with phosgene, in the presence of n-butyl isocyanate and a tertiary amine catalyst, at reflux in a solvent such as xylene. A preferred catalyst is 1,4-diazabicyclo[2.2.2]octane (DABCO).

Alternatively, many of the sulfonyl isocyanates VI can be prepared, although again in low yields, from sulfonamides by a two-step procedure. This consists of (1) reacting the sulfonamide with n-butyl isocyanate and a base such as potassium carbonate at reflux in an inert solvent such as 2-butanone to form a n-butyl sulfonylurea; and (2) reacting this compound with phosgene and DABCO catalyst at reflux in xylene solvent. This method is similar to a procedure taught by Ulrich and Sayigh, *New Methods of Preparative Organic Chemistry*, Vol. VI, p. 223–241, Academic Press, New York and London, W. Foerst Ed.

As shown in Equation 3a below, compounds of Formula (I), where W''' is S, can be prepared by reacting sulfonamide II with an appropriate triazine or pyrimidine isothiocyanate of Formula (VIIj).

Equation 3a

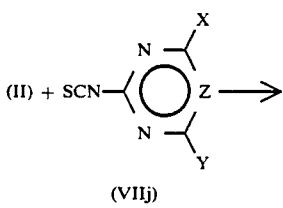

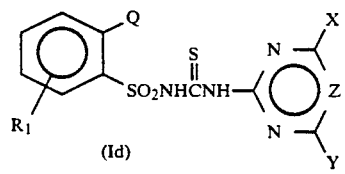

wherein R$_1$, Q, X, Y and Z are as originally defined.

The reaction of Equation 3a is carried out by dissolving or suspending the sulfonamide and isothiocyanate in a polar solvent such as acetone, acetonitrile, ethyl acetate or methyl ethyl ketone, adding an equivalent of a base such as potassium carbonate and stirring the mixture at ambient temperature up to the reflux temperature for one to twenty-four hours as taught in EPO Publication No. 35,893. The required isothiocyanates VIIj are prepared according to the method of Japan Patent Application Pub:Kokai 51-143686, June 5, 1976, or that of W. Abraham and G. Barnikow, Tetrahedron, 29, 691 (1973).

As shown in Equation 4 below, intermediate sulfonamides of Formula (II) described above can be prepared from amines of Formula (VIII) by a two-step procedure. This consists of (4a) diazotizing VIII and coupling the diazonium salt with sulfur dioxide to form a sulfonyl chloride of Formula (IX); and (4b) aminating IX with ammonium hydroxide or anhydrous ammonia to form II.

Equation 4

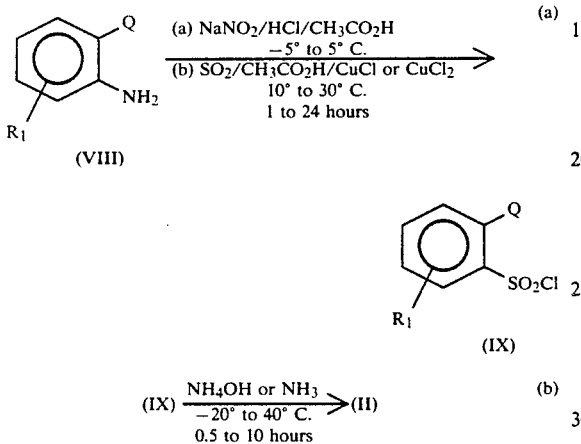

wherein $R_1$ and Q are as originally defined.

The reaction of Equation 4a is accomplished by treating a solution of amine VIII in a mixture of concentrated hydrochloric acid and glacial acetic acid with a solution of sodium nitrite in water at $-5°$ to $5°$ C. After stirring for 10–30 minutes at about 0° C. to insure complete diazotization, the solution is added to a mixture of an excess of sulfur dioxide and a catalytic amount of cuprous chloride or cupric chloride in glacial acetic acid at about 10° C. The temperature is kept at about 10° C. for $\frac{1}{4}$ to 1 hour, then raised to 20° to 30° C. and held at that temperature for 2 to about 24 hours. This solution is then poured into a large excess of ice water. The sulfonyl chloride IX can be isolated by filtration or by extraction into a solvent such as ethyl ether, methylene chloride or preferably, 1-chlorobutane, followed by evaporation of the solvent.

The amination described in the reaction of Equation 4b above is conveniently carried out by treating a solution of the sulfonyl chloride IX with at least two mole equivalents of anhydrous ammonia in a solvent such as ethyl ether or methylene chloride at $-20°$ to 30° C. If the sulfonamide product II is insoluble, it may be isolated by filtration followed by washing out the salts with water. If product II is soluble in the reaction solution, it may be isolated by filtering off the precipitated ammonium chloride and evaporation of the solvent. Alternatively, many sulfonamides II can be prepared by reaction of corresponding sulfonyl chlorides IX with excess aqueous ammonium hydroxide in tetrahydrofuran at 0° to about 40° C. for 0.5 to 10 hours. The sulfonamide product II is isolated by evaporation of the tetrahydrofuran solvent, addition of water to the residue and filtration.

Alternatively, the intermediate sulfonyl chloride IXa can be prepared as shown below in Equation 4a.

Equation 4a

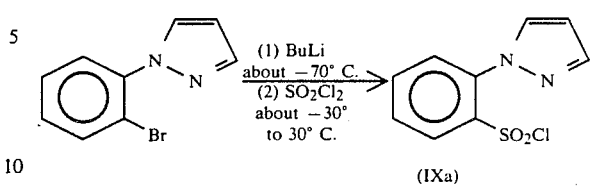

According to Equation 4a, a lithium salt, prepared by reaction of 1-(2-bromophenyl)pyrazole with butyl lithium in ether at about $-70°$ C., is added to sulfuryl chloride in hexane at about $-30°$ to $-20°$ C. and stirred for 0.5 to 10 hours at $-30°$ to 30° C. to yield sulfonyl chloride IXa, according to teachings of S. N. Bhattacharya et al., J. Chem. Soc. (C), 1265 (1968). Subsequent reaction of IXa with ammonia or ammonium hydroxide as described above provides the corresponding sulfonamide.

Starting with appropriate ortho-(heterocyclic)-bromobenzenes, and carrying out the procedures described in Equation 4a, or simple modifications thereof, one skilled in the art may prepare some of the other sulfonyl chlorides of Formula (IX) described above. Of necessity, the reactions are limited to those cases in which the ortho-hetero group, Q, is inert to lithium reagents under the conditions of the reactions, which will be obvious to one skilled in the art. For a general review of metalation with lithium reagents, see H. W. Gschwend and H. R. Rodriguez, Org. Reactions, 26, 1 (1979).

Some of the amines of Formula (VIII) in Equation 4 above are known. For instance, 4-(2-aminophenyl)isothiazole may be prepared by the procedure of J. H. Finley, J. Heterocycl. Chem., 6, 841 (1969); 2-(2-aminophenyl)-1,3,4-thiadiazole by the procedure of M. Ohta, J. Pharm. Soc. Japan, 73, 701 (1953); 2-(2-aminophenyl)-5-methyl-1,3,4-thiadiazole by the procedure of S. Leistner and G. Wagner, Z. Chem., 14, 305 (1974); 2-(2-aminophenyl)-1,3,4-oxadiazole by the procedure of M. Vincent et al., Bull. Soc. Chim. France, 1580 (1962); 3-(2-aminophenyl)-5-methyl-1,2,4-oxadiazole by the procedure of H. Goncalves et al., Bull. Soc. Chim. France, 2599 (1970); 4-(2-aminophenyl)-1,2,4-triazole by the procedure of M. Khan and J. Polya, J. Chem. Soc. C, 85 (1970); and 3-methyl-4-(2-aminophenyl)-1,2,4-triazole and 3,5-dimethyl-4-(2-aminophenyl)-1,2,4-triazole by the procedure of W. Ried and H. Lohwasser, Justus Liebigs Ann. Chem., 699, 88 (1966).

As shown in Equation 5 below, other amines of Formula (VIII) can be prepared by reduction of corresponding nitrobenzenes of Formula (X) with reagents described below.

Equation 5

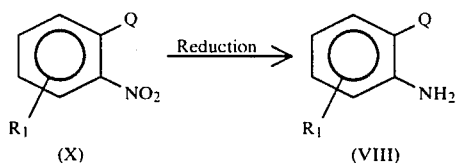

wherein $R_1$ and Q are as originally defined.

The reduction reactions of Equation 5 above can be run by methods known in the literature by one skilled in the art. For instance, many of the reductions can be run by one or more of the following methods:

(a) with stannous chloride or tin and hydrochloric acid, either neat or in an inert solvent such as methanol, at about 25° to 80° C. for 0.5 to 10 hours. For details refer to similar procedures described in G. Corsi et al., *Boll. Chim. Farm.*, 103, 115 (1964); J. H. Finley, *J. Heterocycl. Chem.*, 6, 841 (1969); A. Quilico et al., *Gazz. Chim. Ital.*, 76, 87 (1946); and M. Khan and J. Polya, *J. Chem. Soc. C.*, 85 (1970).

(b) with ferrous sulfate heptahydrate and 28% ammonium hydroxide in an inert solvent such as aqueous ethanol at about 40° to 80° C. for about 1 to 2 hours. For details refer to similar procedures described in T. Naito et al., *Chem. Pharm. Bull.*, 16, 160 (1968); Neth. Appl. 6,608,094; and U.S. Pat. No. 3,341,518;

(c) with ammonium chloride and iron powder in an inert solvent such as water at 50° to about 80° C. for 1 to 3 hours. For details refer to a similar procedure described in M. Ohta et al., *J. Pharm. Soc. Japan*, 73, 701 (1953);

(d) with sodium hydrogen sulfide in an inert solvent such as methanol at about 40° to 70° C. for about 0.5 to 1 hour. For details refer to similar procedures described in G. Corsi et al., *Boll. Chim. Farm.*, 103, 115 (1964); and U.S. Pat. No. 3,270,029;

(e) by catalytic reduction with 5% palladium-on-charcoal, in the presence of 2 to 5 equivalents of aqueous hydrochloric acid, in an inert solvent such as ethanol at 25° to 45° C. at 1 to 3 atmospheres of hydrogen. For details refer to a similar procedure described in U.S. Pat. No. 3,910,942; and Ger. Offen. No. 2,415,978;

(f) by catalytic reduction with 5% Raney Nickel in an inert solvent such as ethanol or dioxane at 25° to 45° C. at 1 to 3 atmospheres of hydrogen. For details refer to similar procedures described in U.S. Pat. No. 3,270,029 and Neth. Appl. 6,513,932;

(g) by catalytic reduction with 5% palladium-on-charcoal in an inert solvent such as methanol at 25° to 45° C. at 1 to 3 atmospheres of hydrogen for short reaction times, i.e., less than 1 hour. For details refer to a similar procedure described in M. Vincent et al., *Bull. Soc. Chim. France*, 1580 (1962), and, (h) by reduction with Raney Nickel catalyst and hydrazine hydrate in 95% ethanol at 25° to 80° C. for 0.2 to about 1 hour. For details refer to a similar procedure described in C. Ainsworth et al., *J. Med. Pharm. Chem.*, 5, 383 (1962).

(i) with sodium sulfide in 50% aqueous p-dioxane at about 25° to 80° C. for 0.25 to 1 hour, or with sodium sulfide and sodium bicarbonate in refluxing methanol for 1 to 10 hours. For details refer to Y. Lin and S. Lang, Jr., *J. Heterocycl. Chem.*, 17, 1273 (1980) and P. Smith and J. Boyer, *J. Am. Chem. Soc.*, 73, 2626 (1951) respectively; and, (j) with sodium hydrosulfite in ethanol-water at about 25° to 60° C. for 0.25 to 1 hour at a pH of less than 7. For details refer to U.S. Pat. No. 4,229,343.

The ortho-heteroaromatic nitrobenzenes of Formula (X) in Equation 5 above are important starting compounds for preparing the compounds I of this invention, which can be prepared by the following methods.

As shown in Equation 6 below, certain 5-(2-nitrophenyl)isoxazoles of Formula (Xa) can be prepared by reacting a 2-nitrophenyl alkyl ketone of Formula (XI) with an appropriate dimethylalkanamide dimethyl acetal of Formula (XII) to form a 3-dimethylamino-1-(2-nitrophenyl)-2-propen-1-one of Formula (XIII). Subsequent reaction of XIII with hydroxylamine hydrochloride provides Xa.

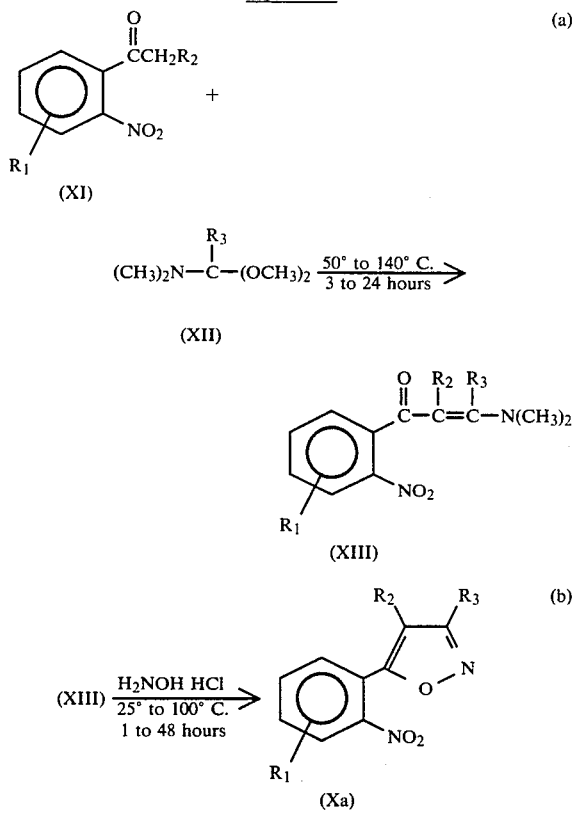

wherein
R$_1$ is as originally defined; and
R$_2$ and R$_3$ are H, CH$_3$ or C$_2$H$_5$.

The reaction of Equation 6a is run at 50° to 140° C. for 3 to 24 hours in a solvent such as toluene or dimethylformamide or excess dimethyl alkanamide dimethyl acetal. The product can be isolated by evaporating the solvent. For more details, refer to similar procedures described in *Technical Information Bulletin*, "DMF Acetals", Aldrich Chemical, December 1973, and Lin and Lang, *J. Org. Chem.*, 45, 4857 (1980). The preparation of dimethyl alkanamide dialkyl acetals is reviewed in Abdulla and Brinkmeyer, *Tetrahedron*, 35, 1675 (1979).

The reaction of Equation 6b above is run in an inert solvent such as ethanol or aqueous dioxane at 25° to 100° C. for 1 to 48 hours. The product is isolated by addition of water and extraction with methylene chloride. For more details refer to similar procedures described in Lin and Lang, *J. Heterocycl. Chem.*, 14, 345 (1977).

Another method for preparing some 5-(2-nitrophenyl)isoxazoles is shown in Equation 7 below. The method requires transforming a 2-nitrophenyl alkyl ketone of Formula (XI) by a series of procedures to a 5-(2-nitrophenyl)isoxazolin-3-one of Formula (XVI). Subsequent reaction of XVI with phosphorus oxychloride or phosphorus oxybromide provides 3-halo-5-(2-nitrophenyl)isoxazoles of Formula (Xa'). Reaction of Xa' with a sodium methoxide, sodium ethoxide or sodium methylmercaptide then provides 3-alkoxy or 3- methylthio-5-(2-nitrophenyl)isoxazoles of Formula (Xa'').

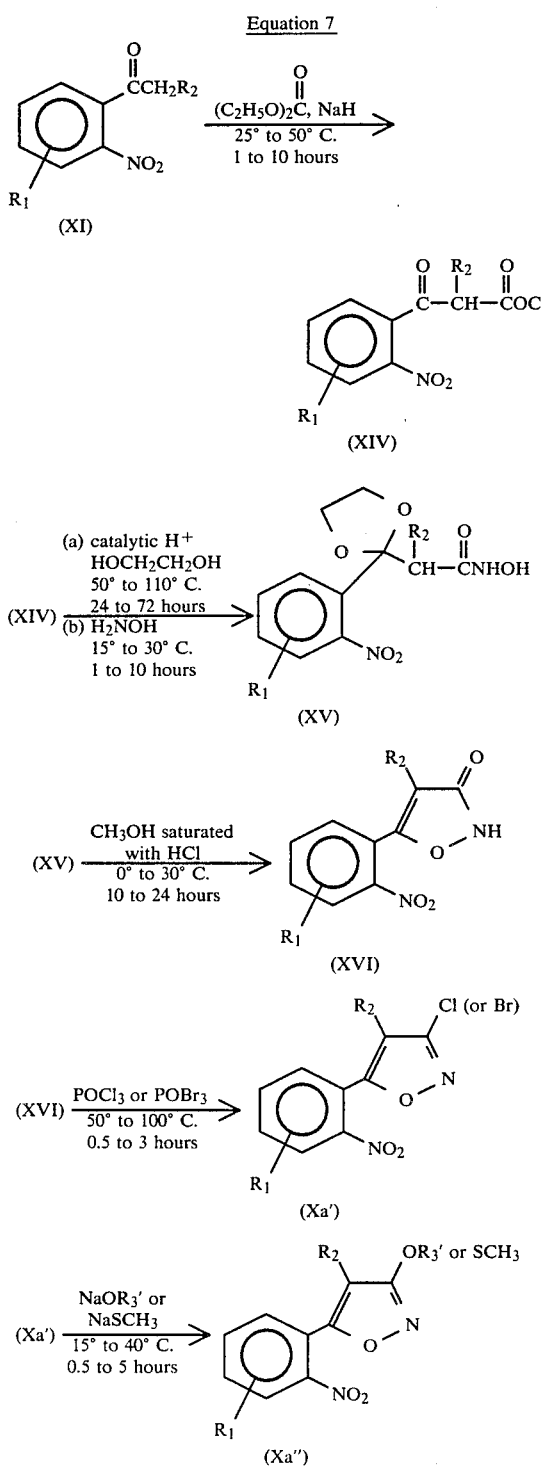

wherein
R₁ as originally defined;
R₂ is H, CH₃ or C₂H₅; and
R₃' is CH₃ or C₂H₅.

The 5-(2-nitrophenyl)isoxazolin-3-one of Formula (XVI) in Equation 7 above can be prepared by a series of reactions similar to those described in the art for transforming acetophenone to 5-phenylisoxazolin-3-one, e.g., R. Jacquier et al., *Bull. Soc. Chim.*, 3694 (1969) and ibid., 1978 (1970). Thus, by substituting 2-nitrophenyl alkyl ketone XI for acetophenone and carrying out the appropriate reactions in the cited art, and which are illustrated in reactions of Equations 7a to 7c, one skilled in the art can prepare XVI. The reaction of Equation 7d is run in a solvent such as toluene at 50° to 100° C. for 0.5 to 3 hours. The product is isolated by evaporation of the solvent and purified by column chromatography on silica gel. Reaction 7e is run in a solvent such as methanol or tetrahydrofuran at about 15° to 40° C. for 0.5 to 5 hours. The product is isolated by addition of water and extraction with methylene chloride. The product is purified by column chromatography on silica gel.

As shown in Equation 8 below, 4-halo-5-(2-nitrophenyl)isoxazoles of Formula (Xa'''') can be prepared by halogenating 5-(2-nitrophenyl)isoxazoles of Formula (Xa''') with halogenating reagents described below.

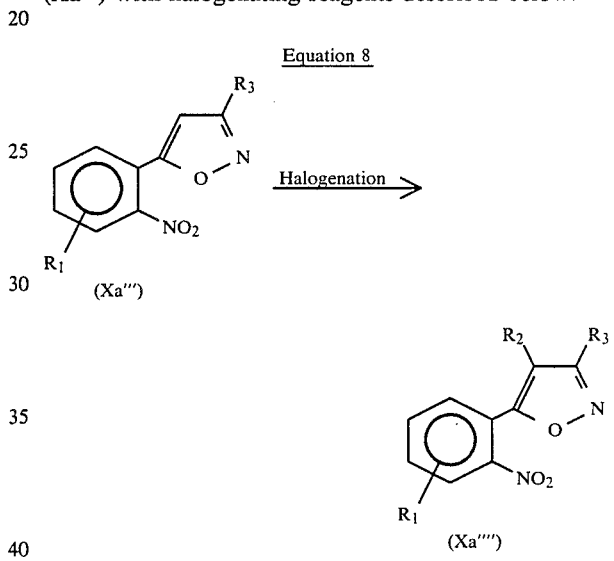

wherein
R₁ and R₃ are as originally defined; and
R₂ is Cl or Br.

The reaction of Equation 8 can be run by one or more of the following methods known in the art for halogenating phenylisoxazoles in the 4-position of the isoxazole ring in preference to the phenyl ring or other positions of the isoxazole ring:

(a) reacting Xa''' with sulfuryl chloride or sulfuryl bromide at 15° to 80° C. for 0.5 to 3 hours, either neat or in a solvent such as methylene chloride or carbon tetrachloride, according to the teachings of J. Carr et al., *J. Heterocycl. Chem.* 20, 934 (1977);

(b) reacting Xa''' with chlorine or bromine at 15° to 60° C. for 0.5 to 5 hours in methylene chloride or acetic acid, according to the teachings of ibid; or (c) reacting Xa''' with bromine or chlorine and iron powder catalyst in a solvent such as carbon tetrachloride at 25° to 80° C. for 0.5 to 3 hours, according to the teachings of N. Kochetkov et al., *Zhur. Obshchei. Khim.*, 28, 359 (1958). The preparation of Xa''' is described in Equations 6 and 7 above.

As shown in Equation 9 below, 4-(2-nitrophenyl)isoxazoles of Formula (Xb) can be prepared by reacting a 3-(dimethylamino)-2-(2-nitrophenyl)acrolein of Formula (XVII) with hydroxylamine hydrochloride.

Equation 9

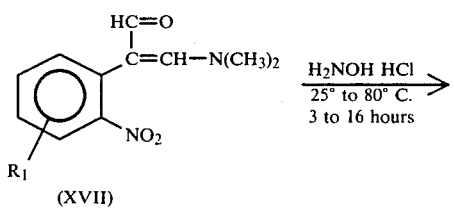

wherein
$R_1$ is as originally defined.

The reaction of Equation 9 is run in ethanol at 25° to 80° C. for 3 to 16 hours. The product is isolated by addition of water and extraction with methylene chloride. The product is purified by recrystallization or column chromatography on silica gel. The starting material XVII is prepared by known methods, e.g., U. Hengartner et al., *J. Org. Chem.*, 44, 3748 (1979).

5-Methyl-4-(2-nitrophenyl)isoxazoles of Formula (Xb') can be prepared as shown in Equation 10 below. The method requires reacting a 2-nitrophenylpropanone of Formula (XVIII) with ethyl formate and sodium ethoxide to form a 3-oxo-2-(2-nitrophenyl)-butyraldehyde of Formula (XIX). Subsequent reaction of XIX with hydroxylamine provides Xb'.

Equation 10

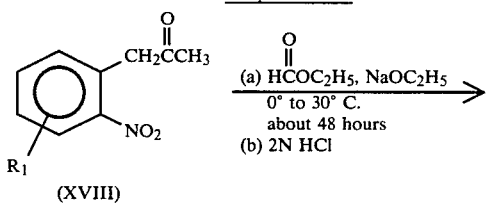

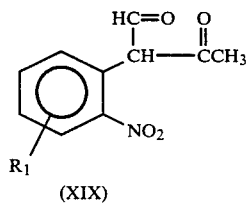

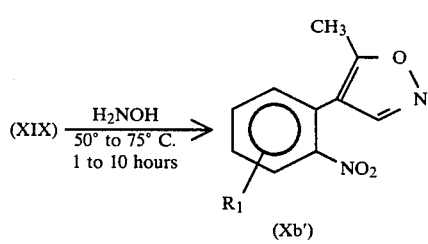

wherein
$R_1$ is as originally defined.

The reaction of Equation 10a is run in ethanol at 0° to about 30° C. for about 48 hours. The product is isolated by addition of water and 2N HCl and extraction with methylene chloride. The reaction of Equation 10b is also run in ethanol at reflux for about 1 to 10 hours. The product is isolated by addition of water and extraction with methylene chloride. For more details refer to similar procedures described in H. Yasuda, *Yakugaku Zasshi*, 79, 623 (1959).

As shown in Equation 11 below, 3,5-dimethyl-4-(2-nitrophenyl)isoxazoles of Formula (Xb'') can be prepared by reacting a 3-(2-nitrophenyl)pentan-2,4-dione of Formula (XX) with hydroxylamine.

Equation 11

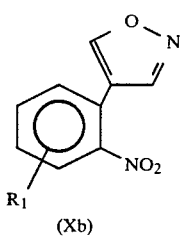

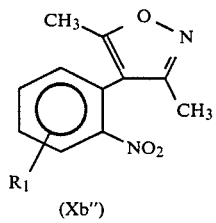

wherein
$R_1$ is as originally defined.

The reaction of Equation 11 is run in ethanol at 50° to 75° C. for about 3 to 10 hours. The product is isolated by addition of water and extraction with methylene chloride. For more details refer to similar procedures described in Bobranski and Wojtowski, *Roczniki Chem.*, 38, 1327 (1964). The starting compounds XX can be prepared by reacting an appropriate 2-halo-nitrobenzene with the sodium salt of pentan-2,4-dione by methods obvious to one skilled in the art.

Equation 12 below illustrates a method for preparing 3-(2-nitrophenyl)isoxazoles of Formula (Xc).

Equation 12

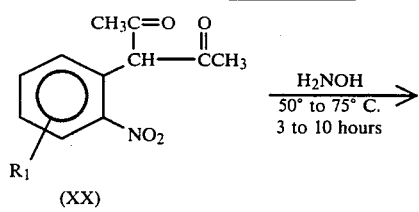

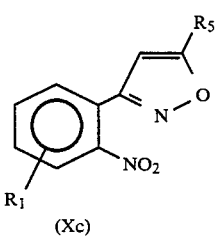

wherein $R_1$ is as originally defined; and
$R_5$ is H, $CH_3$, $C_2H_5$, $OCH_3$ or $OC_2H_5$.

The reaction of Equation 12 is run by procedures similar to those taught by M. Langella et al., *Chim. Ind. (Milan)*, 47, 996 (1965) for the preparation of 3-(2-nitrophenyl)isoxazole, and by G. Gaudiano et al., *Gazz. Chim. Ital.*, 89, 2466 (1959) for the preparation of 5-ethoxy-3-(2-nitrophenyl)isoxazole. Thus, a 2-nitrophenylhydroxamic acid chloride of Formula (XXI) is reacted with an appropriate acetylenic Grignard reagent in tetrahydrofuran at 0° to 30° C. for 1 to about 16 hours. The product is isolated by addition of water and ammonium chloride and extraction with methylene chloride. The acetylenic Grignard reagents are prepared from substituted acetylenes by procedures described in the cited references.

Equation 13 below illustrates a method for preparing 3-(2-nitrophenyl)isoxazoles of Formula (Xc').

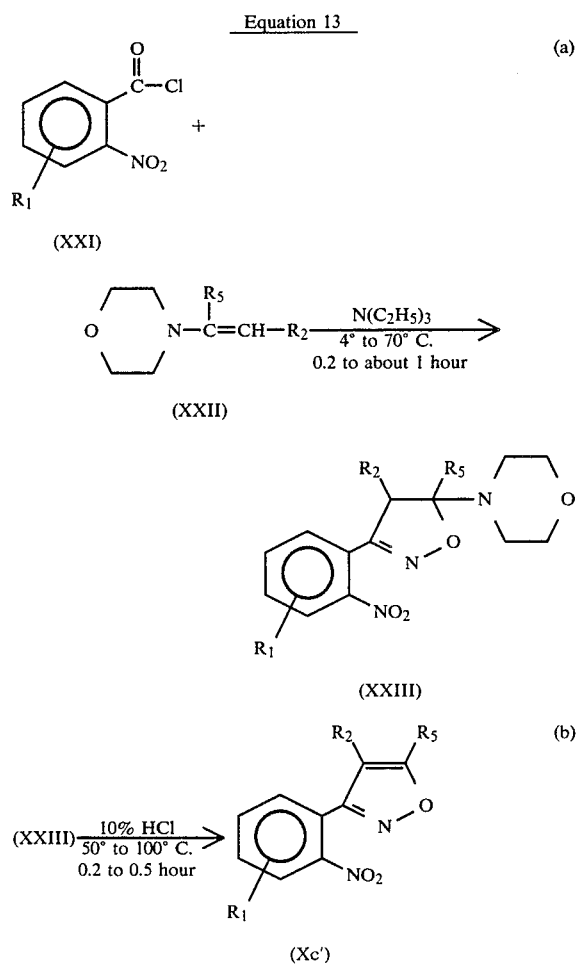

wherein
$R_1$ is as originally defined;
$R_2$ is $CH_3$ or $C_2H_5$; and
$R_5$ is H, $CH_3$ or $C_2H_5$.

The reactions of Equation 13 above can be run by procedures similar to those described in G. Bianchetti et al., *Gazz. Chim. Ital.*, 93, 1714 (1963) for the preparation of various 3-phenylisoxazoles. Thus, in reaction 13a, a 2-nitrophenylhydroxamic acid chloride of Formula (XXI) is reacted with an equimolar amount of triethylamine and a N-alkenylmorpholine of Formula (XXII) in chloroform at reflux for 0.2 to about 1 hour to form a 5-(N-morpholinyl)-3-(2-nitrophenyl)isoxazoline of Formula (XXIII). In reaction 13b, XXIII is reacted with 10% hydrochloric acid at reflux for about 0.2 to 0.5 hour to form Xc'. The product Xc' is isolated by extraction with methylene chloride.

Equation 14 below illustrates a method for preparing 3-(2-nitrophenyl)isoxazoles of Formula (Xc'').

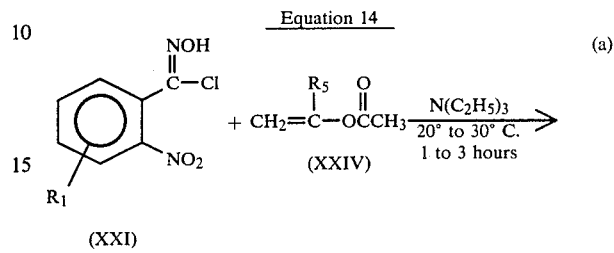

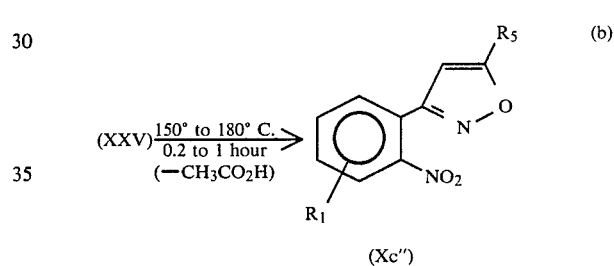

wherein
$R_1$ is as originally defined; and
$R_5$ is H, $CH_3$ or $C_2H_5$.

The reactions of Equation 14 above can be run by procedures similar to those described in R. Micetich, *Can. J. Chem.*, 48, 467 (1970) for the preparation of various 3-phenylisoxazoles. Thus, in reaction 14a, a 2-nitrophenylhydroxamic acid chloride XXI is reacted with equimolar amounts of a vinyl acetate of Formula (XXIV) and triethylamine in a solvent such as ether or tetrahydrofuran at about 30° C. for 1 to 3 hours to form a 5-acetoxy-3-(2-nitrophenyl)isoxazoline of Formula (XXV). In reaction 14b, XXV is heated at about 150° to 180° C. for a short period to form Xc''.

Equation 15 below illustrates a method for preparing 5-halo-3-(2-nitrophenyl)isoxazoles of Formula (Xc''') and 5-alkoxy- or 5-methylthio-3-(2-nitrophenyl)isoxazoles of Formula (Xc'''').

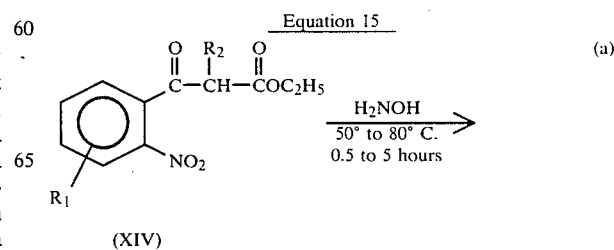

-continued
Equation 15

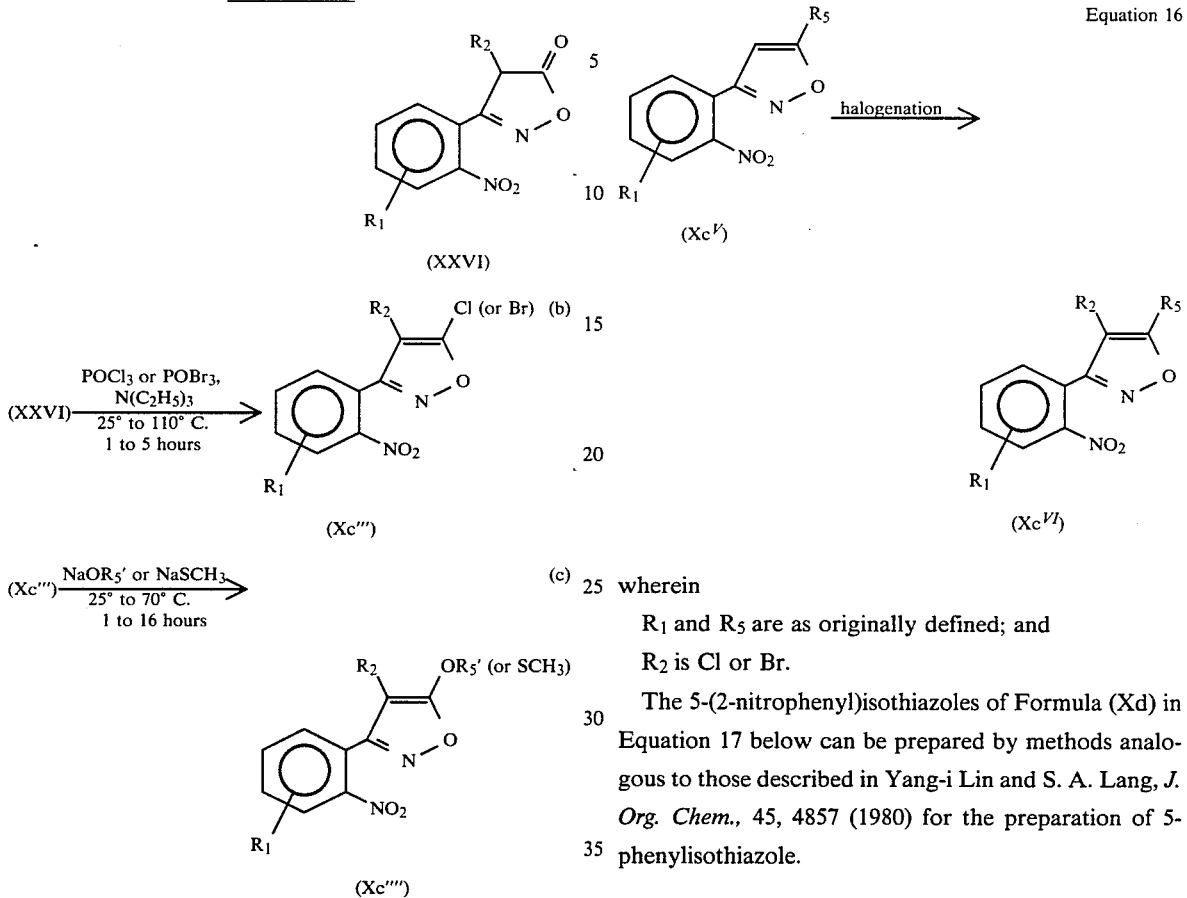

wherein
$R_1$ is as originally defined;
$R_2$ is H, $CH_3$ or $C_2H_5$; and
$R_5'$ is $CH_3$ or $C_2H_5$.

The reactions of Equations 15a and 15b above can be run by procedures similar to those described in U.S. Pat. No. 3,781,438 for the preparation of 5-halo-3-phenylisoxazoles. Thus, in reaction 15a, an ethyl 2-(2-nitrobenzoyl)acetate, propionate or butyrate of Formula (XIV) is reacted with hydroxylamine hydrochloride and sodium acetate in ethanol at reflux for 0.5 to 5 hours to form a 3-(2-nitrophenyl)isoxazolin-5-one of Formula (XXVI). In reaction 15b, XXVI is reacted with an equimolar amount of triethylamine and excess phosphorus oxychloride or phosphorus oxybromide in toluene at 25° to 110° C. for 1 to 5 hours to form Xc'''.

The reaction of Equation 15c above can be run by procedures similar to those described in J. Carr et al., *J. Med. Chem.*, 20, 934 (1977) and R. Micetich et al., *Can. J. Chem.*, 48, 1371 (1970). Thus, Xc''' is reacted with sodium methoxide, sodium ethoxide or sodium methylmercaptide in tetrahydrofuran at 25° to 70° C. for 1 to 16 hours to form (Xc'''').

As shown in Equation 16 below, 4-halo-3-(2-nitrophenyl)isoxazoles of Formula ($Xc^{VI}$) can be prepared by halogenating 3-(2-nitrophenyl)isoxazoles of Formula ($Xc^V$). The reaction is run using reagents and procedures described above in Equation 8. The preparation of $Xc^V$ is described above in Equations 12, 14 and 15.

wherein
$R_1$ and $R_5$ are as originally defined; and
$R_2$ is Cl or Br.

The 5-(2-nitrophenyl)isothiazoles of Formula (Xd) in Equation 17 below can be prepared by methods analogous to those described in Yang-i Lin and S. A. Lang, *J. Org. Chem.*, 45, 4857 (1980) for the preparation of 5-phenylisothiazole.

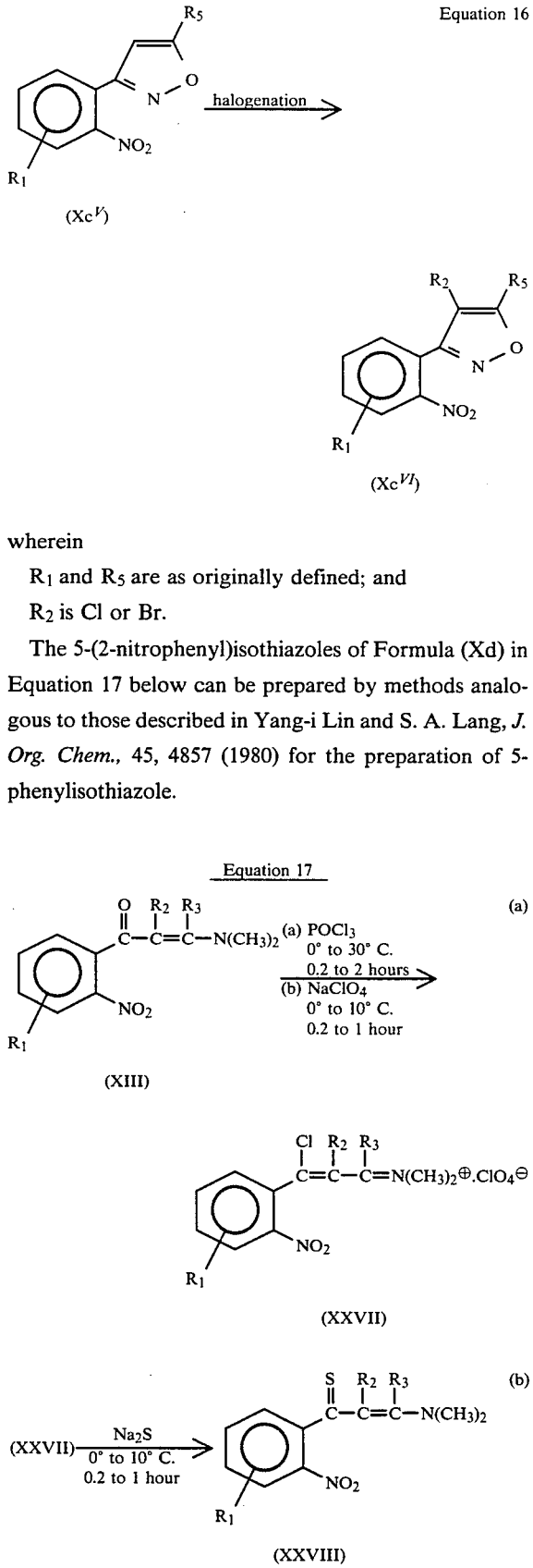

-continued
Equation 17

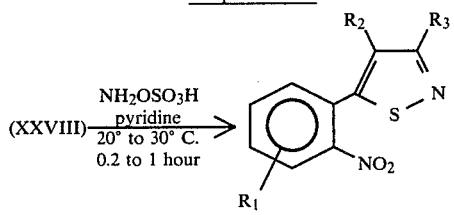

(Xd)

wherein
R₁ is as originally defined; and
R₂ and R₃ are H, CH₃ or C₂H₅.

According to Equation 17 above, in reaction 17a a 3-dimethylamino-1-(2-nitrophenyl)-2-propen-1-one of Formula (XIII) is reacted with phosphorus oxychloride in methylene chloride at 0° to 30° C. for 0.2 to about 2 hours, followed by treatment with sodium perchlorate in water at 0° to 10° C. for 0.2 to about 1 hour to form a perchlorate salt of Formula (XXVII). In reaction 17b, XXVII is reacted with sodium sulfide nonahydrate in dimethylformamide and water at 0° to 10° C. for 0.2 to about 1 hour to form a 3-dimethylamino-1-(2-nitrophenyl)-2-propene-1-thione of Formula (XXVIII). And in reaction 17c, XXVIII is reacted with hydroxylamine-O-sulfonic acid (HSA) and two mole equivalents of pyridine in methanol at 20° to 30° C. for 0.2 to about 1 hour to form Xd. The preparation of the starting compounds XIII is described in Equation 6 above.

3-Alkoxy-5-(2-nitrophenyl)isothiazoles of Formula (Xd') in Equation 18 below can be prepared by methods similar to those described in Ber., 96, 944 (1963); German No. 1,193,050 and German No. 1,197,088. The cited references describe the preparation of other 3-alkoxy-5-phenylisothiazoles.

Equation 18

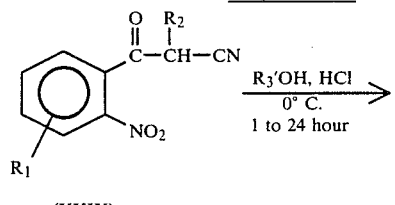

(XXIX)

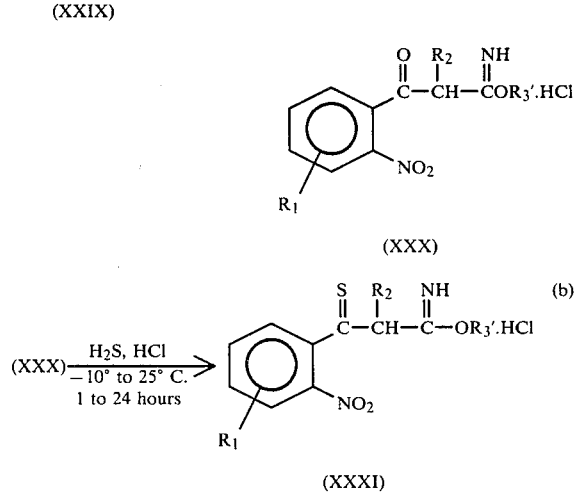

-continued
Equation 18

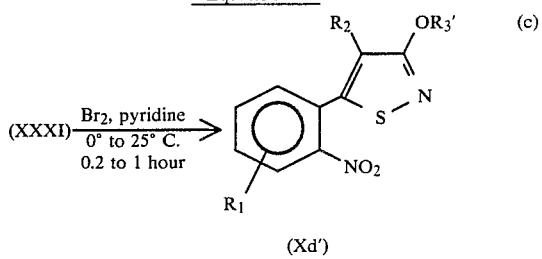

(Xd')

wherein
R₁ is as originally defined;
R₂ is H, CH₃ or C₂H₅; and
R₃' is CH₃ or C₂H₅.

According to Equation 18, in reaction 18a a 2'-cyano-2-nitroacetophenone of Formula (XXIX) is reacted with methanol or ethanol in a solvent such as ethyl ether or toluene saturated with hydrogen chloride gas at about 0° C. for 1 to 24 hours to form a 2-nitrobenzoylacetamido alkyl ester of Formula (XXX). In reaction 18b, XXX is reacted with hydrogen sulfide in absolute methanol or ethanol saturated with hydrogen chloride gas at about −10° to 25° C. for 1 to 24 hours to form a 2-nitrothiobenzoylacetamido alkyl ester of Formula (XXXI). And in reaction 18c, XXXI is reacted with bromine in ethyl acetate containing pyridine at 0° to about 25° C. for about 0.2 to 1 hour to form Xd'.

Equation 19 below illustrates a method of preparing 3-halo-5-(2-nitrophenyl)isothiazoles of Formula (Xd") and 3-methylthio-5-(2-nitrophenyl)isothiazoles of Formula (Xd''').

Equation 19

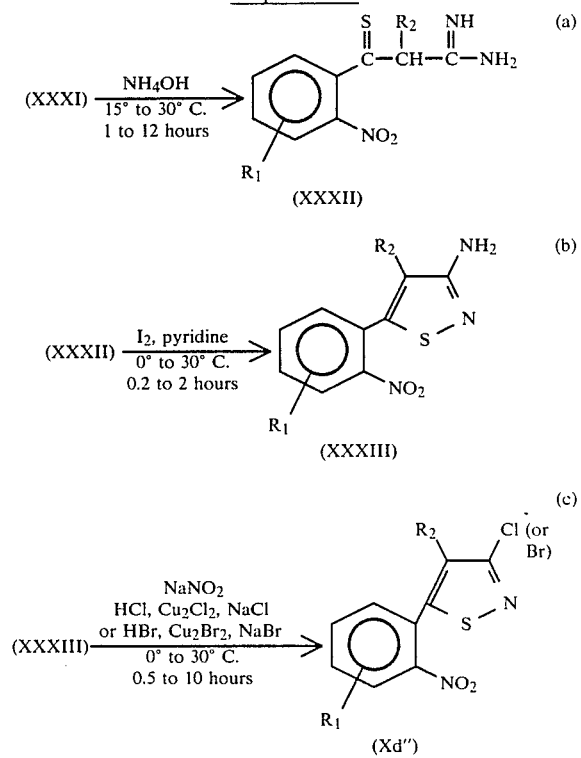

-continued
Equation 19

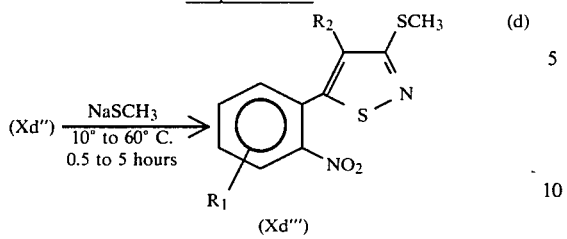

(d)

wherein
R$_1$ is as originally defined; and
R$_2$ is H, CH$_3$ or C$_2$H$_5$.

The reactions of Equations 19a and 19b above can be run by procedures similar to those described in *Ber.*, 96, 944 (1963); German Pat. No. 1,193,050; and German Pat. No. 1,197,088 for the preparation of other 3-amino-5-phenylisothiazoles. Thus, in reaction 19a, a 2-nitrothiobenzoylacetamido alkyl ester of Formula (XXXI) is reacted with aqueous 24% NH$_4$OH at 15° to 30° C. for 1 to about 12 hours to form a 2-nitrothiobenzoylacetamidine of Formula (XXXII). In reaction 19b, XXXII is reacted with iodine in methanol containing pyridine at 0° to about 30° C. for about 0.2 to 2 hours to form a 3-amino-5-(2-nitrophenyl)isothiazole of Formula (XXXIII).

In the reaction of Equation 19c above, Xd″ is prepared from XXXIII via Sandmeyer reactions, according to the teachings of J. Goerdeler and M. Roegler, *Chem. Ber.*, 103, 112 (1970). Thus, XXXIII is reacted with sodium nitrite in concentrated HCl containing Cu$_2$Cl$_2$ and NaCl or in concentrated HBr containing Cu$_2$Br$_2$ and NaBr at 0° to 30° C. for 0.5 to 10 hours to give Xd″. And in reaction 19d, Xd″ is reacted with sodium methylmercaptide in tetrahydrofuran at 10° to 60° C. for 0.5 to 5 hours to form Xd‴. The product is isolated by addition of water and extraction with methylene chloride.

The 4-halo-5-(2-nitrophenyl)isothiazoles of Formula (Xd$^V$) in Equation 20 below are prepared by halogenating 5-(2-nitrophenyl)isothiazoles of Formula (Xd″″) with chlorine or bromine in the presence of a base such as sodium acetate. The reaction is run in acetic acid at 10° to 100° C. for 0.5 to 5 hours. For more details refer to similar procedures described in the art for halogenating other 5-phenylisothiazoles, e.g., D. Buttimore et al., *J. Chem. Soc.*, 2032 (1963); T. Naito et al., *Chem. Pharm. Bull.*, 16, 148 (1968); and J. Goerdeler and W. Mittler, *Ber.*, 96, 944 (1963).

Equation 20

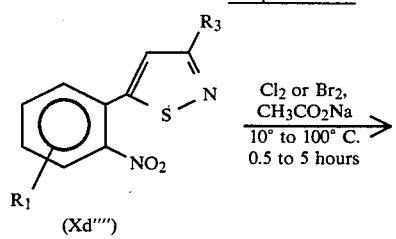

-continued
Equation 20

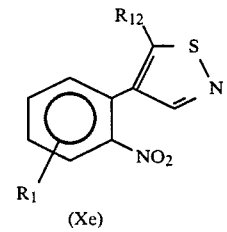

wherein
R$_1$ and R$_3$ are as originally defined; and
R$_2$ is Cl or Br.

The 4-(2-nitrophenyl)isothiazoles of Formula (Xe) in Equation 21 below can be prepared by nitrating 4-phenylisothiazoles of Formula (XXXIV) with concentrated nitric acid in concentrated sulfuric acid, according to the teachings of J. H. Finley and G. P. Volpp, *J. Heterocycl. Chem.*, 6, 841 (1969).

Equation 21

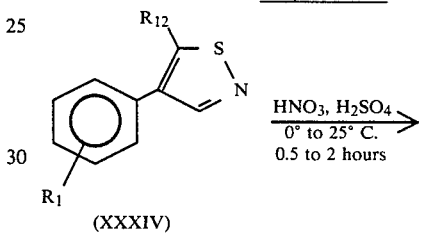

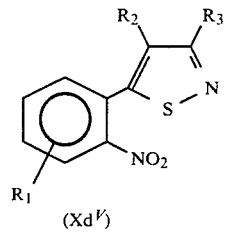

wherein
R$_{12}$ is H or CH$_3$.

The reaction of Equation 21 above is run at 0° to 25° C. for 0.5 to 2 hours. Following usual work-up the product Xe is purified by column chromatography on silica gel. The starting compounds XXXIV can be prepared by known methods. Several such methods are described in M. Muehlstaedt, *J. Prakt. Chem.*, 318, 507 (1976); M. Ohashi et al., *J. Chem. Soc.*, 1148 (1970); R. A. Olofson et al., *Tetrahedron*, 22, 2119 (1966); and F. Huebenett et al., *Angew Chem.*, 75, 1189 (1963).

As shown in Equation 22 below, the 3-(2-nitrophenyl)isothiazoles of Formula (Xf) and (Xf′) can be prepared by a series of procedures starting from a 2-nitrobenzonitrile of Formula (XXXV).

Equation 22

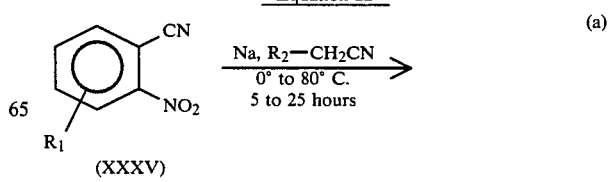

(a)

-continued
Equation 22

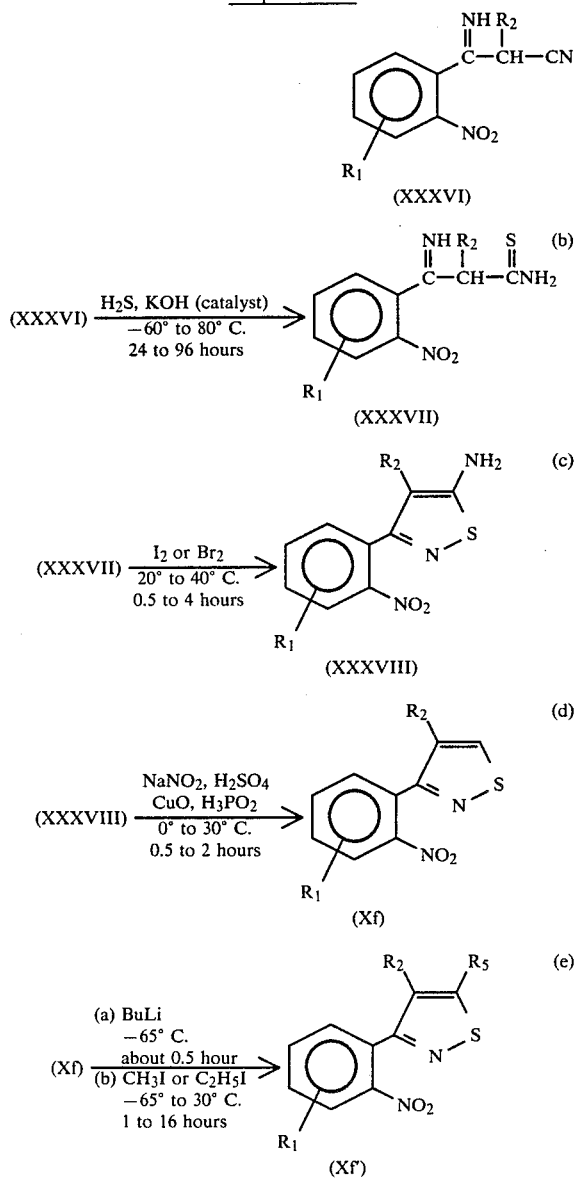

wherein
R₁ is as originally defined; and
R₂ and R₅ are H, CH₃ or C₂H₅.

The reactions of Equation 22 above can be run by procedures known in the art. Thus, in reaction 22a, 2-nitrobenzonitrile XXXV can be reacted with an appropriate alkyl nitrile and sodium metal in a solvent such as ether or toluene at 0° to 80° C. for about 5 to 25 hours to form a 2-imino-2-(2-nitrophenyl)propionitrile of Formula (XXXVI), according to the teachings of U.S. Pat. No. 3,479,365; Netherlands No. 6,608,094; and T. Naito et al., *Bull. Chem. Soc. Japan*, 41, 965 (1968).

In the reaction of Equation 22b, XXXVI can be reacted with hydrogen sulfide and potassium hydroxide catalyst in methylene chloride at −60° to 80° C. in a sealed tube for 24 to 96 hours to form a 2-imino-2(2-nitrophenyl)thiopropionamide of Formula (XXXVII), according to the teachings of T. Naito et al., *Chem. Pharm. Bull.*, 16, 148 (1968) and J. Goerdeler and H. Pohland, *Chem. Ber.*, 94, 2950 (1961).

In the reaction of Equation 22c above, XXXVII can be cyclized by reaction with iodine or bromine in a solvent such as ether, chloroform or ethanol containing potassium carbonate at 20° to 40° C. for 0.5 to 4 hours to form a 5-amino-3-(2-nitrophenyl)isothiazole of Formula (XXXVIII), according to the teachings of ibid., Netherlands No. 6,608,094 and J. Goerdeler and H. Pohland, *Angew Chem.*, 72, 77 (1962).

In the reaction of Equation 22d above, a diazonium salt, prepared from XXXVIII and sodium nitrite in sulfuric acid at 0° C. for 0.5 hour, can be reacted with cuprous oxide and 50% hypophosphorous acid at 0° to 30° C. for about 2 hours to form a 3-(2-nitrophenyl)isothiazole of Formula (Xf), according to the teachings of M. Beringer et al., *Helv. Chim. Acta.*, 49, 2466 (1966).

And in the reaction of Equation 22e above, Xf can be reacted with butyl lithium in tetrahydrofuran at −65° C. for about 0.5 to form a 5-lithio-3-(2-nitrophenyl)isothiazole reagent, according to the teachings of T. Naito et al., *Chem. Pharm. Bull.*, 16, 148 (1968). Subsequent reaction of this reagent with methyl or ethyl iodide, at −65° to 30° C. for 1 to 16 hours, can provide Xf', according to the teachings of ibid.

The 5-halo-3-(2-nitrophenyl)isothiazoles of Formula (Xf'') in Equation 23 below can be prepared from 5-amino-3-(2-nitrophenyl)isothiazoles of Formula (XXXVIII) by Sandmeyer reactions.

Equation 23

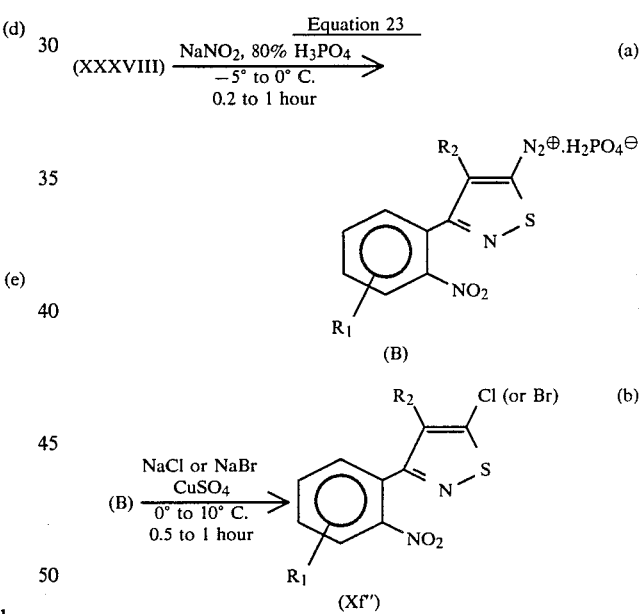

wherein
R₁ is as originally defined; and
R₂ is H, CH₃ or C₂H₅.

The reactions of Equation 23 above can be run by procedures similar to those described in J. Goerdeler and H. Pohland, *Chem. Ber.*, 94, 2950 (1961) for the preparation of 5-chloro-3-phenylisothiazole. Thus, in reaction 23a, XXXVIII is diazotized with sodium nitrite in 80% phosphoric acid at −5° to 0° C. for about 0.5 hour. In reaction 23b, the diazonium salt B is reacted with sodium chloride or sodium bromide and copper sulfate catalyst at 0° to 10° C. for about 1 hour to form Xf''. The preparation of XXXVIII is described in Equation 22 above.

The 5-alkoxy- and 5-methylthio-3-(2-nitrophenyl)isothiazoles of Formula (Xf''') in Equation 24 below are prepared by reacting a 5-halo-3-(2-nitrophenyl)isothiazole of Formula (Xf″) with sodium methoxide, sodium ethoxide or sodium methylmercaptide.

Equation 24

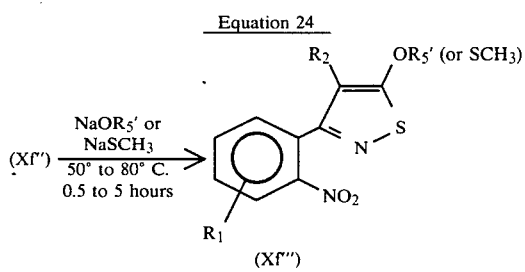

wherein
$R_1$ is as originally defined;
$R_2$ is H, $CH_3$ or $C_2H_5$; and
$R_5'$ is $CH_3$ or $C_2H_5$.

The reaction of Equation 24 is run in a solvent such as methanol, ethanol or tetrahydrofuran at reflux for about 0.5 to 5 hours. The product is isolated by evaporation of solvent, addition of water and filtration. The reaction of 5-haloisothiazoles with alkoxides or thioalkoxides to form 5-alkoxy- or 5-alkylthioisothiazoles is known in the art, e.g., K. R. H. Wooldrige, *Adv. in Heterocycl. Chem.*, 14, p. 24 (1972).

The 4-halo-3-(2-nitrophenyl)isothiazoles of Formula (Xf$^V$) in Equation 25 below are prepared by halogenating 3-(2-nitrophenyl)isothiazoles of Formula (Xf‴) according to procedures described above in Equation 20. The preparation of Xf‴ is described above in Equations 22–24.

Equation 25

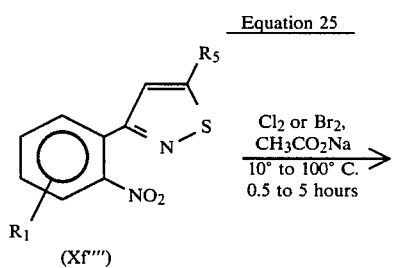

wherein
$R_1$ and $R_5$ are as originally defined; and
$R_2$ is Cl or Br.

Equation 26 below illustrates a method for preparing 3-(2-aminophenyl)-1H-pyrazoles of Formula (VIIIa) and 5-(2-aminophenyl)-1H-pyrazoles of Formula (VIIIb).

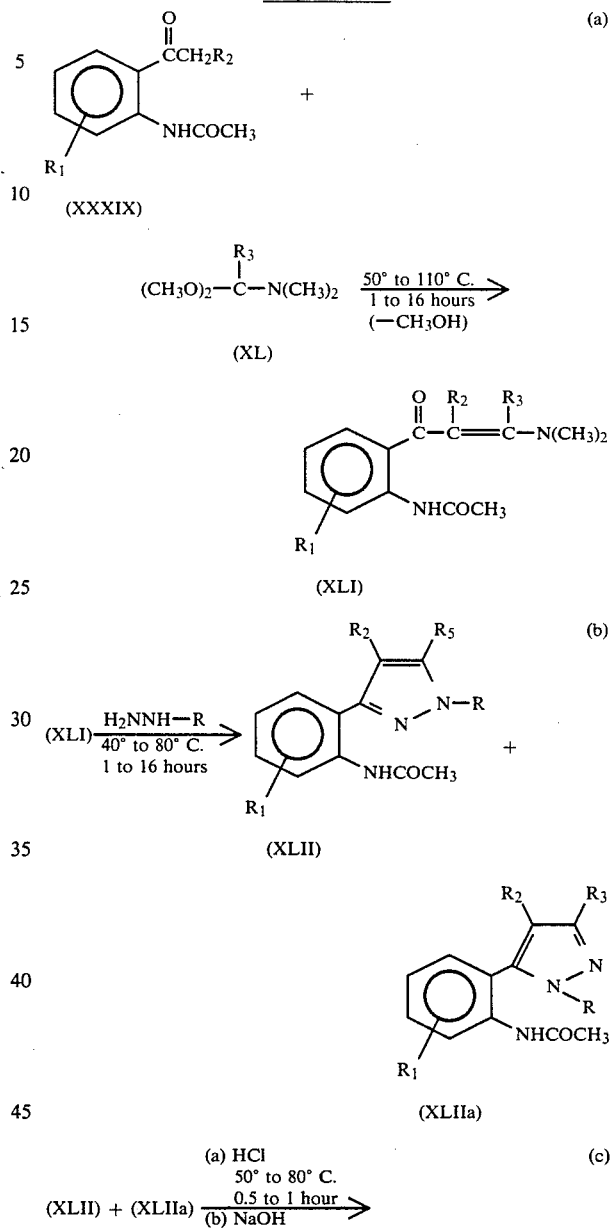

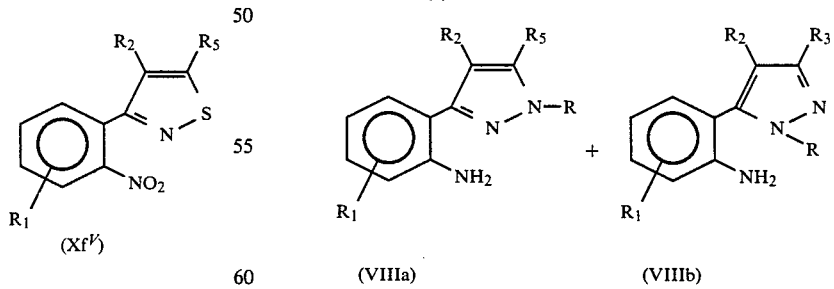

wherein
R and $R_1$ are as originally defined; and
$R_2$, $R_3$ and $R_5$ are H, $CH_3$ or $C_2H_5$.

According to Equation 26 above, in reaction 26a, a 2-acetamidophenyl alkyl ketone of Formula (XXXIX) is reacted with a dimethylalkanamide dimethyl acetal of Formula (XL) to form a 3-dimethylamino-1-(2- acetamidophenyl)-2-propen-1-one of Formula (XLI). The reaction can be run by procedures described above for the reaction of Equation 6a.

In the reaction of Equation 26a, XLI is reacted with an appropriate hydrazine to form a mixture containing 3-(2-acetamidophenyl)-1H-pyrazole of Formula (XLII) and 5-(2-acetamidophenyl)-1H-pyrazole of Formula (XLIIa). The reaction is run in ethanol at reflux for 1 to 16 hours. The product mixture is isolated by evaporation of the solvent.

And in the reaction of Equation 26c, amines VIIIa and VIIIb are obtained by acid hydrolysis of acetamides XLII and XLIIa in the following manner. A mixture containing XLII and XLIIa in concentrated hydrochloric acid is heated at reflux for about 1 hour, cooled and filtered. The solid, composed of hydrochloride salts of VIIIa and VIIIb, is neutralized in water with 50% NaOH. A mixture containing amines VIIIa and VIIIb is isolated by extraction with methylene chloride. Amines VIIIa and VIIIb may be separated by high pressure liquid chromatography by one skilled in the art. More preferably, the mixture is reacted directly by procedures described in Equations 4 and 1 or 2 above to provide corresponding compounds I of the invention as a mixture.

Equation 27 below illustrates a method for preparing 5-halo-3-(2-nitrophenyl)-1H-pyrazoles of Formula (Xg) and 3-halo-5-(2-nitrophenyl)-1H-pyrazoles of Formula (Xh).

Equation 27

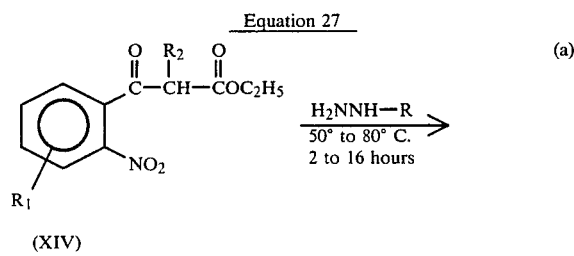

(XIV)

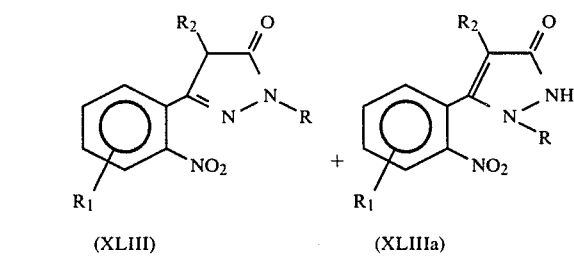

(XLIII)    (XLIIIa)

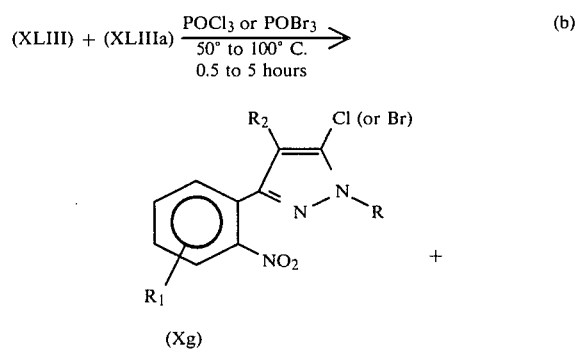

(Xg)

-continued
Equation 27

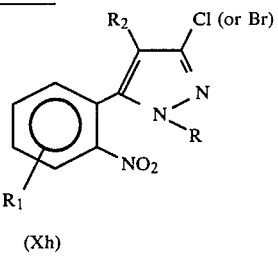

(Xh)

wherein
R is $C_1$-$C_3$ alkyl;
$R_1$ is as originally defined; and
$R_2$ is H, $CH_3$ or $C_2H_5$.

According to Equation 27 above, in reaction 27a, an ethyl 3-(2-nitrophenyl)-3-oxopropanoate of Formula (XIV) is reacted with an alkylhydrazine to form a mixture containing a 3-(2-nitrophenyl)pyrazolin-5-one of Formula (XLIII) and a 5-(2-nitrophenyl)pyrazolin-3-one of Formula (XLIIIa). The reaction is run in ethanol at reflux for 2 to 16 hours. The product is isolated by addition of water and extraction with methylene chloride.

And in the reaction of Equation 27b, the mixture containing XLIII and XLIIIa is reacted with phosphorus oxychloride or phosphorus oxybromide to form a mixture containing Xg and Xh. The reaction is run in toluene at 50° to 100° C. for 0.5 to 5 hours. The product mixture is isolated by evaporation of the solvent and may be purified by column chromatography on silica geol. The mixture may be separated by high pressure liquid chromatography by one skilled in the art.

Equation 28 below illustrates a method for preparing 5-alkoxy- and 5-methylthio-3-(2-nitrophenyl)-1H-pyrazoles of Formula (Xg') and 3-alkoxy- and 3-methylthio-5-(2-nitrophenyl)-1H-pyrazoles of Formula (Xh').

Equation 28

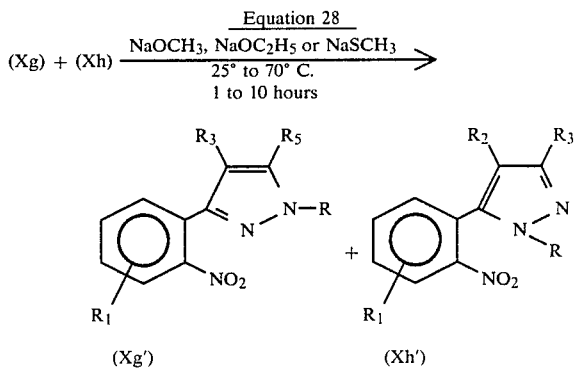

(Xg')    (Xh')

wherein
R is $C_1$-$C_3$ alkyl;
$R_1$ is as originally defined;
$R_2$ is H, $CH_3$ or $C_2H_5$; and
$R_3$ and $R_5$ are $OCH_3$, $OC_2H_5$ or $SCH_3$.

According to Equation 28 above, a mixture containing a 5-halo-3-(2-nitrophenyl-1H-pyrazole of Formula (Xg) and a 3-halo-5-(2-nitrophenyl)-1H-pyrazole of Formula (Xh) is reacted with sodium methoxide, sodium ethoxide or sodium methylmercaptide to form a mixture containing Xg' and Xh'. The reaction is run in a solvent such as methanol or tetrahydrofuran at 25° to 70° C. for 1 to 10 hours. The product mixture is isolated by addition of water followed by extraction with methylene chloride. The mixture may be purified by column chromatography on silica gel. The mixture may be separated by high pressure liquid chromatography by one skilled in the art.

As shown in Equation 29 below, 4-(2-nitrophenyl)-1H-pyrazoles of Formula (Xi) are prepared by reacting a 3-dimethylamino-2-(nitrophenyl)acrolein of Formula (XVII) with an appropriate hydrazine.

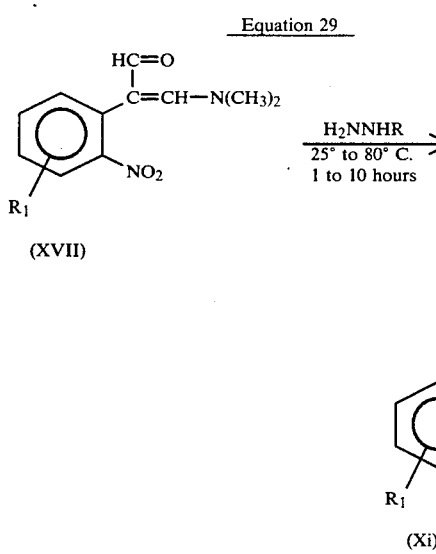

wherein
R and $R_1$ are as originally defined.

The reaction of Equation 29 above is run in ethanol at 25° to 80° C. for 1 to 10 hours. The product is isolated by evaporation of the solvent and purified by recrystallization procedures.

As shown in Equation 30 below, a 3,5-dimethyl-4-(2-nitrophenyl)-1H-pyrazole of Formula (Xi') is prepared by reacting a 3-(2-nitrophenyl)pentan-2,4-dione of Formula (XX) with an appropriate hydrazine. The reaction can be run by procedures described above in Equation 29.

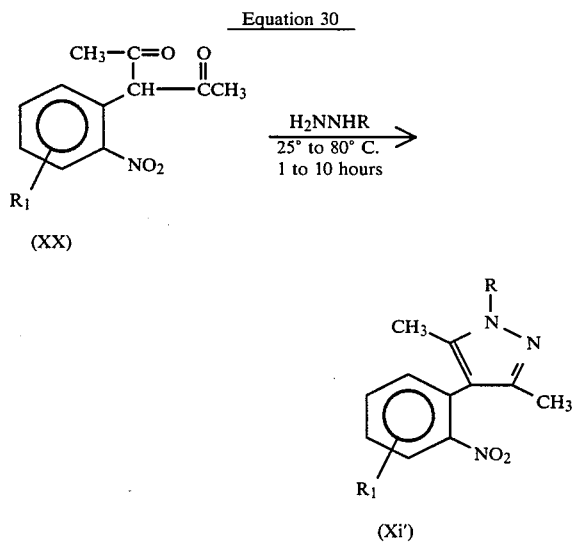

wherein
R and $R_1$ are as originally defined.

A mixture containing 4-(2-nitrophenyl)-1H-pyrazoles of Formula (Xi'') and (Xi''') can be prepared by reacting a 3-oxo-2-(2-nitrophenyl)butyraldehyde of Formula (XIX) with an appropriate hydrazine, as shown in Equation 31 below.

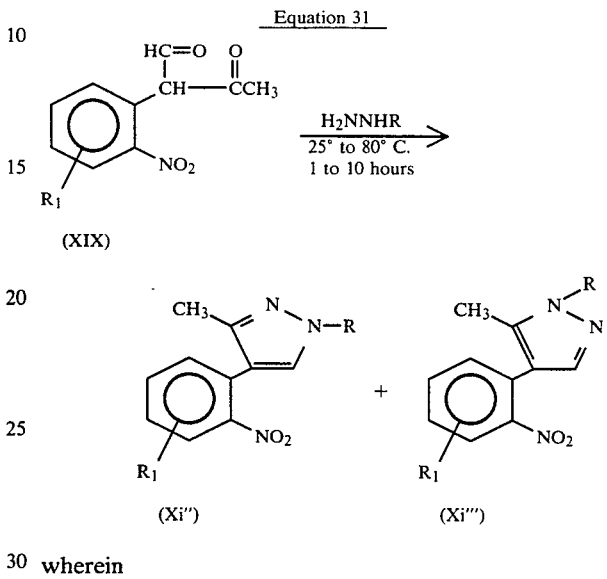

wherein
R and $R_1$ are as originally defined.

The reaction of Equation 31 above can be run by procedures described in Equation 29 above. The product mixture can be transformed to a mixture of corresponding compounds I of the invention by a sequence of reactions described above in Equations 5, 4 and 1 or 2, respectively.

As shown in Equation 32 below, a 1-(2-nitrophenyl)-1H-pyrazole of Formula (Xj) can be prepared by reacting a 2-nitrophenylhydrazine of Formula (XLIV) with a 1,3-diketone of Formula (XLV).

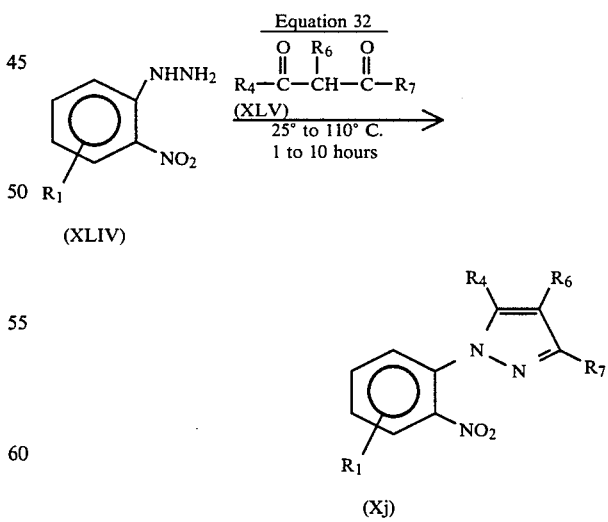

wherein
$R_1$ and $R_6$ are as originally defined; and
$R_4$ and $R_7$ are $C_1$-$C_3$ alkyl.

The reaction of Equation 32 is run in a solvent such as tetrahydrofuran or toluene at 25° to 110° C. for 1 to 10 hours. The product is isolated by evaporation of the solvent and purified by recrystallization or chromatography procedures in the usual manner. 1-(2-Nitrophenyl)-1H-pyrazoles of Formula Xj above can also be prepared, where $R_4$ to $R_7$ are H, by reacting an appropriate 2-nitrophenylhydrazine with 1,1,3,3-tetraethoxypropane in ethanol at reflux for about 0.5 to 3 hours, according to the teachings of I. Finar and R. Hurlock, *J. Chem. Soc.*, 3024 (1957).

Another method for preparing 1-(2-nitrophenyl)-1H-pyrazoles is illustrated in Equation 33 below, where $R_4$ and $R_7$ can be H as well as $C_1$-$C_3$ alkyl.

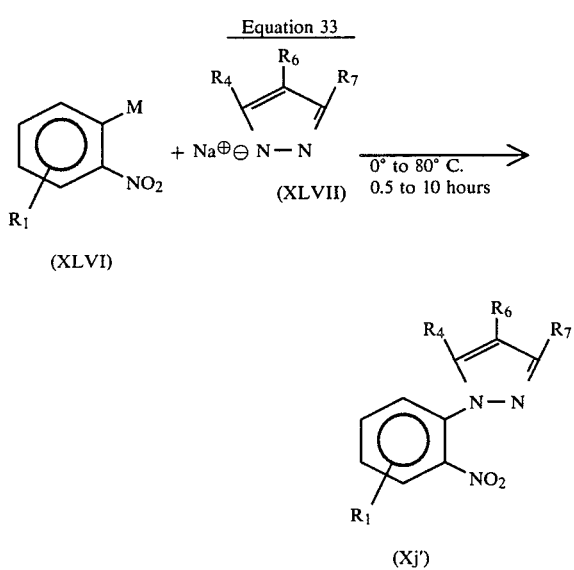

wherein
M is Cl, Br or F; and
$R_1$ to $R_7$ are as originally defined.

According to Equation 33, a pyrazole sodium salt of Formula (XLVII) is reacted with a 2-halo-1-nitrobenzene of Formula (XLVI) to form Xj'. The reaction can be run in an aprotic solvent such as tetrahydrofuran or dimethylformamide at about 0° to 80° C. for 0.5 to 10 hours. The product is isolated in the usual manner by addition of water and extraction with methylene chloride. The product is purified by recrystallization or chromatography procedures. The sodium salt XLVII is formed by reacting an appropriate pyrazole with sodium hydride in situ by methods known in the art.

Many 1-(2-nitrophenyl)-1H-pyrazoles of Formula (Xj') above can also be prepared by the Ullmann reaction, according to the teachings of M. Khan and J. Polya, *J. Chem. Soc. C.*, 85 (1970). This requires the reaction of a 2-halonitrobenzene, such as XLVI above, with an appropriately substituted pyrazole, copper (II) oxide catalyst and potassium carbonate in pyridine at reflux for 0.5 to several hours. The product is purified by column chromatography.

The 2-(2-nitrophenyl)-1,3,4-oxadiazoles of Formula (Xk) in Equation 34 below can be prepared by reacting a 2-nitrobenzhydrazide of Formula (XLVIII) with excess triethylorthoformate at 100° to 150° C. for 5 to 24 hours, according to procedures described in U.S. Pat. No. 3,808,223.

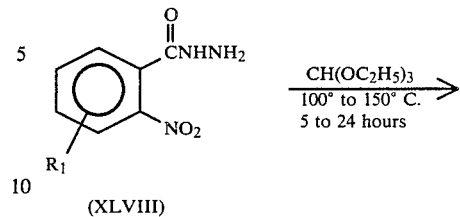

wherein
$R_1$ is as originally defined.

The 2-alkyl-5-(2-nitrophenyl)-1,3,4-oxadiazoles of Formula (Xk') in Equation 35 below can be prepared by heating a 2-nitrobenzhydrazide of Formula (XLIX) in excess phosphorus oxychloride at 70° to 100° C. for 0.5 to 2 hours, according to procedures described in ibid.

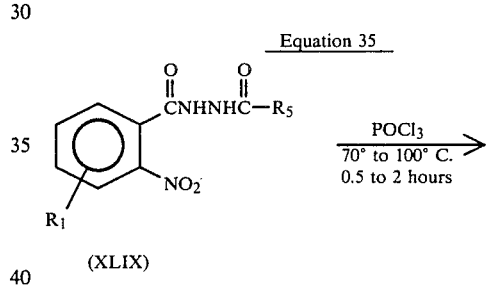

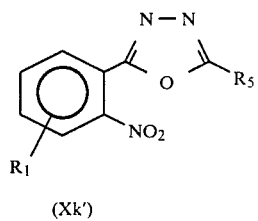

wherein
$R_1$ is as originally defined; and
$R_5$ is $CH_3$ or $C_2H_5$.

Equation 36 below illustrates a method for preparing 2-methylthio-5-(2-nitrophenyl)-1,3,4-oxadiazoles of Formula (Xk'').

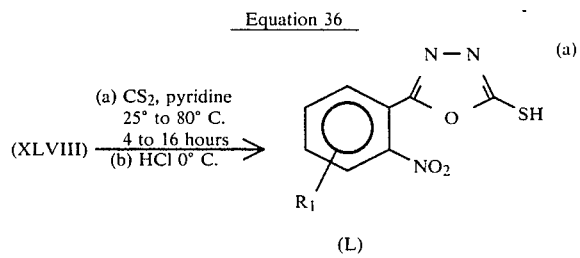

-continued
Equation 36

(b) 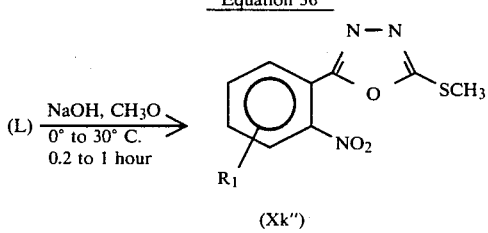

(Xk'')

wherein
R₁ is as originally defined.

The reactions of Equation 36 above can be run according to similar procedures described in E. Hogarth, *J. Chem. Soc.*, 4811 (1952). Thus, in reaction 36a, 2-nitrobenzhydrazide XLVIII is reacted with carbon disulfide in pyridine solvent at 25° to 80° C. for about 4 to 16 hours, followed by addition of water and acidification with hydrochloric acid to form a 2-mercapto-5-(2-nitrophenyl)-1,3,4-oxadiazole of Formula (L). In reaction 36b, L is reacted with sodium hydroxide and methyl iodide in water at 0° to 30° C. for 0.2 to 1 hour to form Xk''.

Equation 37 below illustrates a method for preparing 2-halo-5-(2-nitrophenyl)-1,3,4-oxadiazoles of Formula (Xk''') and 2-alkoxy-5-(2-nitrophenyl)-1,3,4-oxadiazoles of Formula (Xk'''').

Equation 36

(a) 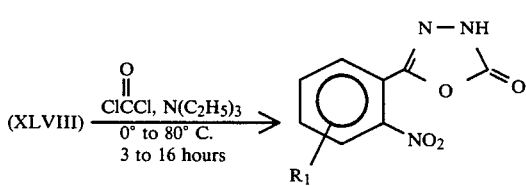

(LI)

(b) 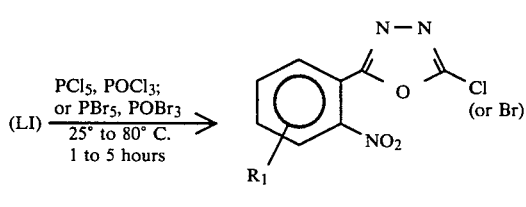

(Xk''')

(c) 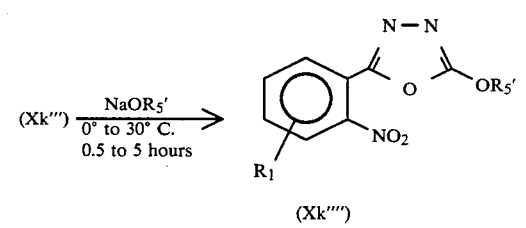

(Xk'''')

wherein
R₁ is as originally defined; and
R₅' is CH₃ or C₂H₅.

The reactions of Equation 37 above can be run according to similar procedures described in U.S. 4,259,104; Golfier and Milcent, *J. Heterocycl. Chem.*, 10, 989 (1973); and R. Madhavan and V. Srinivasan, *Indian J. Chem.* 7, 760 (1969). Thus, in reaction 37a, a 2-nitrobenzhydrazide XLVIII is reacted with phosgene in an aprotic solvent such as benzene at ambient temperature for about 10 hours, followed by addition of two mole equivalents of triethylamine and heating at reflux for about 2 hours to form 2-(2-nitrophenyl)-1,3,4-oxadiazolin-5-one of Formula (LI). In reaction 37b, LI is reacted with phosphorus pentachloride in phosphorus oxychloride or with phosphorus pentabromide in phosphorus oxybromide at 25° to 80° C. for about 5 hours to form (Xk'''). And in reaction 37c, Xk''' is reacted with sodium methoxide or sodium ethoxide in a solvent such as methanol or tetrahydrofuran at 0° to 30° C. for about 0.5 to 5 hours to form Xk''''.

The 3-(2-nitrophenyl)-1,2,4-oxadiazoles of Formula (Xl) in Equation 38 below can be prepared by reacting a 2-nitrobenzamidoxime of Formula (LII) with excess triethylorthoformate at 100° to 150° C. for about 1 to 24 hours, according to the teachings of U.S. Pat. No. 3,910,942.

Equation 38

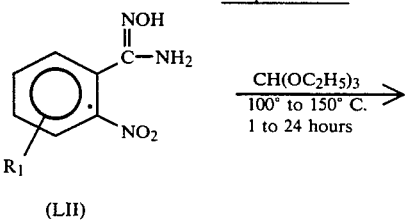

(LII)

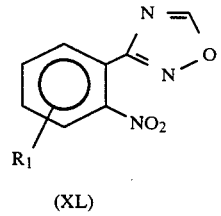

(XL)

wherein
R₁ is as originally defined.

The 5-alkyl-3-(2-nitrophenyl)-1,2,4-oxadiazoles of Formula (Xl') in Equation 39 below can be prepared by reacting 2-nitrobenzamidoxime LII with an appropriate acid chloride in dioxane, with BF₃.(C₂H₅)₂O catalyst, at 25° to 100° C. for about 1 to 18 hours, according to the teachings of ibid., or by reacting LII with acid chloride and pyridine in xylene at 25° to 130° C. for 0.5 to 5 hours, according to the teachings of U.S. Pat. No. 3,270,029. Also, Xl' can be prepared by reacting LII with excess anhydride at 100° to 150° C. for 0.5 to 5 hours, according to the teachings of ibid.

Equation 39

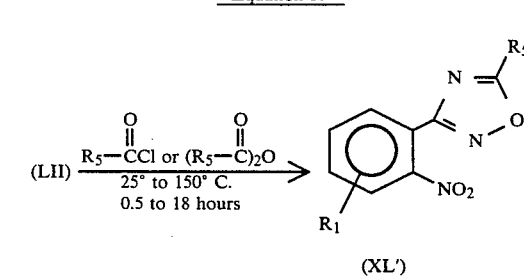

(XL')

wherein
R₁ is as originally defined; and
R₅ is CH₃ or C₂H₅.

The 5-methylthio-3-(2-nitrophenyl)-1,2,4-oxadiazoles of Formula (Xl″) in Equation 40 below can be prepared by reacting 2-nitrobenzamidoxime LII with a N,N-pentamethylen-methylmercapto-formamide chloride of Formula (LIII) in N-methylpyrrolidinone at 50° to 80° C. for about 1 to 10 hours, according to the teachings of H. Eilingsfeld and L. Moebius, *Chem. Ber.*, 98, 1293 (1965).

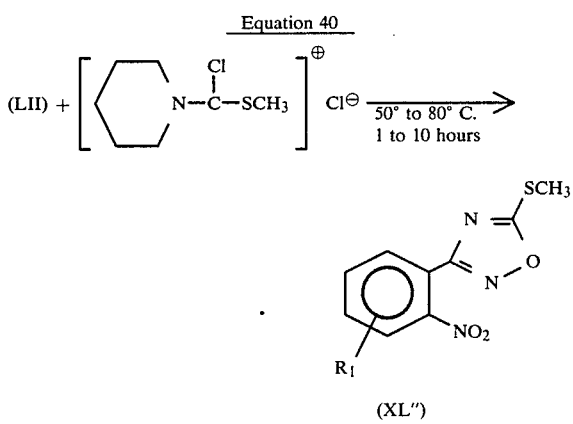

wherein

R₁ is as originally defined.

Equation 41 below illustrates a method for preparing 5-halo-3-(2-nitrophenyl)-1,2,4-oxadiazoles of Formula (Xl‴) and 5-alkoxy-3-(2-nitrophenyl)-1,2,4-oxadiazoles of Formula (Xl″″).

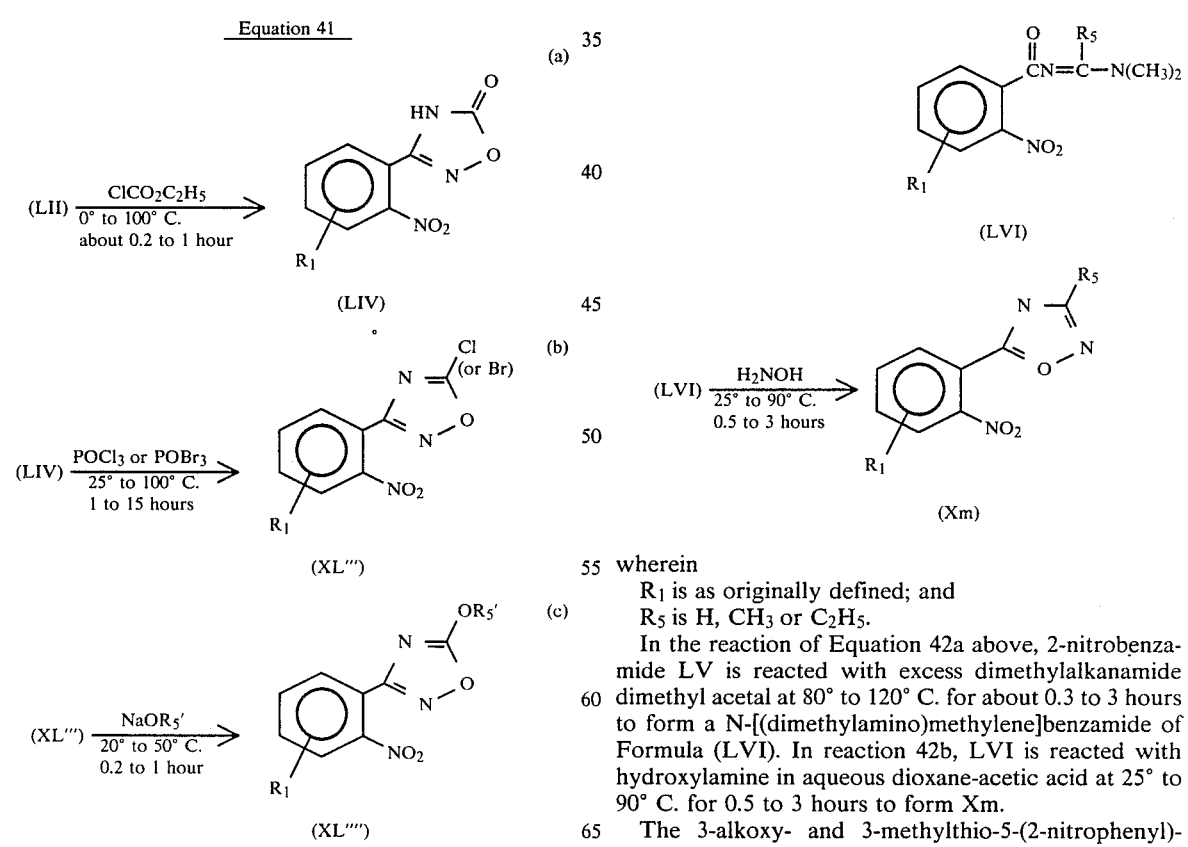

wherein

R₁ is as originally defined; and

R₅′ is CH₃ or C₂H₅.

The reactions of Equation 41 above can be run by methods known in the art. Thus, in reaction 41a, 2-nitrobenzamidoxime LII is reacted with ethyl chloroformate in excess pyridine at 0° to 100° C. for about 1 hour to form a 3-(2-nitrophenyl)-1,2,4-oxadiazolin-5-one of Formula (LIV), according to the teachings of A. R. Katritzky et al., *Tetrahedron*, 21, 1681 (1965). In reaction 41b, LIV is reacted with excess phosphorus oxychloride or phosphorus oxybromide with pyridine catalyst at 25° to 100° C. for 1 to 15 hours to form Xl‴, according to the teachings of T. Fujita et al., *Yakugaku Zasshi*, 84, 1061 (1964). And in reaction 41c, Xl‴ is reacted with sodium methoxide or sodium ethoxide in a solvent such as methanol, ethanol or tetrahydrofuran at 20° to 50° C. for about 0.2 to 1 hour to form Xl″″, according to the teachings of F. Eloy et al., *Bull. Soc. Chim. Belg.*, 78, 47 (1969).

The 5-(2-nitrophenyl)-1,2,4-oxadiazoles of Formula (Xm) in Equation 42 below are prepared according to the teachings of Y. Lin et al., *J. Org. Chem.*, 44, 4160 (1979).

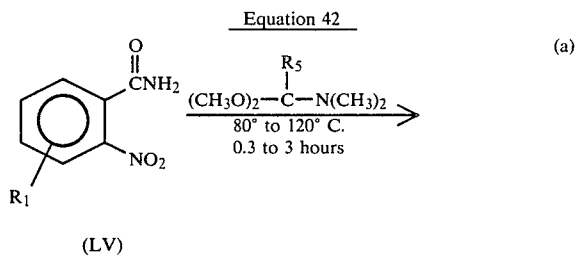

wherein

R₁ is as originally defined; and

R₅ is H, CH₃ or C₂H₅.

In the reaction of Equation 42a above, 2-nitrobenzamide LV is reacted with excess dimethylalkanamide dimethyl acetal at 80° to 120° C. for about 0.3 to 3 hours to form a N-[(dimethylamino)methylene]benzamide of Formula (LVI). In reaction 42b, LVI is reacted with hydroxylamine in aqueous dioxane-acetic acid at 25° to 90° C. for 0.5 to 3 hours to form Xm.

The 3-alkoxy- and 3-methylthio-5-(2-nitrophenyl)-1,2,4-oxadiazoles of Formula (Xm′) in Equation 43 below are prepared according to the teachings of B. Nash et al., *J. Chem. Soc.*, 2794 (1969).

Equation 43

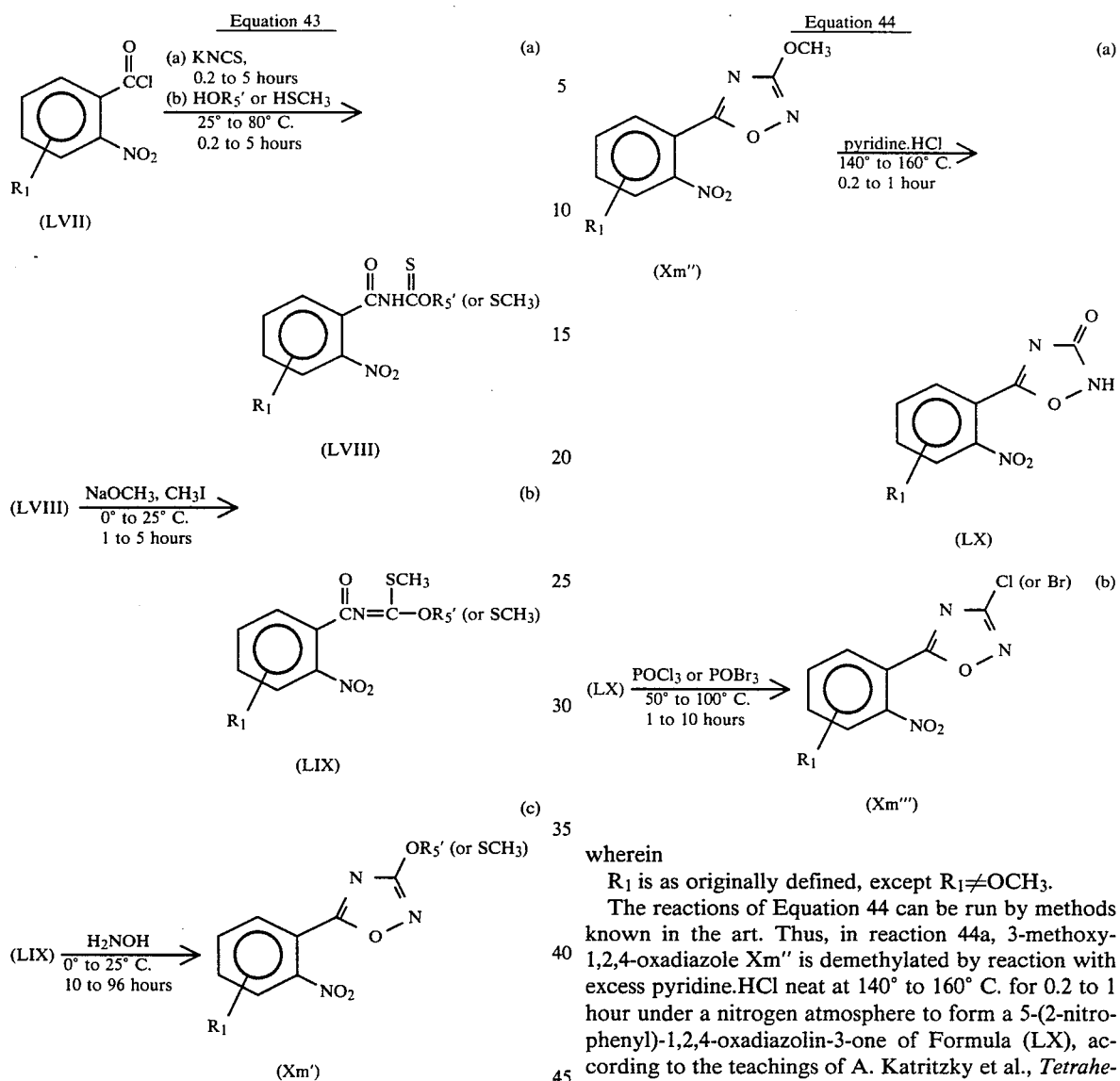

wherein

R$_1$ is as originally defined; and

R$_5'$ is CH$_3$ or C$_2$H$_5$.

Thus, in the reaction of Equation 43a, 2-nitrobenzoyl chloride LVII is reacted with potassium thiocyanate in a solvent such as toluene or acetonitrile at reflux for 0.2 to 5 hours; the resultant benzoyl thiocyanate is then reacted with excess methanol, ethanol or methyl mercaptan at 25° to 80° C. for 0.2 to 5 hours to form an O-alkyl benzoylthiocarbamate or methyl benzoyldithiocarbamate of Formula (LVIII). In reaction 43b, LVIII is reacted with sodium methoxide and methyl iodide in methanol at 0° to 25° C. for 1 to 5 hours to form a dialkyl benzoyliminothiocarbonate or dimethyl benzoyliminodithiocarbonate of Formula (LIX). And in reaction 43c, LIX is reacted with hydroxylamine in methanol or ethanol at 0° to 25° C. for about 10 to 96 hours to form Xm'.

Equation 44 below illustrates a method for preparing 3-halo-5-(2-nitrophenyl)-1,2,4-oxadiazoles of Formula Xm'''.

wherein

R$_1$ is as originally defined, except R$_1 \neq$ OCH$_3$.

The reactions of Equation 44 can be run by methods known in the art. Thus, in reaction 44a, 3-methoxy-1,2,4-oxadiazole Xm" is demethylated by reaction with excess pyridine.HCl neat at 140° to 160° C. for 0.2 to 1 hour under a nitrogen atmosphere to form a 5-(2-nitrophenyl)-1,2,4-oxadiazolin-3-one of Formula (LX), according to the teachings of A. Katritzky et al., *Tetrahedron*, 21, 1681 (1965). In reaction 44b, LX is reacted with phosphorus oxychloride or phosphorus oxybromide, with pyridine catalyst, at 50° to 100° C. for 1 to 10 hours to form Xm''', according to the teachings of Eloy and Deryckere, *Bull. Soc. Chem. Belg.*, 78, 41 (1969).

The 3-(2-nitrophenyl)-1,2,5-oxadiazoles of Formula (Xn) in Equation 45 below can be prepared by heating a 2-nitrophenylglyoxime of Formula (LXI) with 6N NH$_4$OH in an autoclave at 150°–180° C. for 1 to 8 hours, according to the teachings of M. Milone, *Gazz. Chim. Ital.*, 63, 456 (1933).

Equation 45

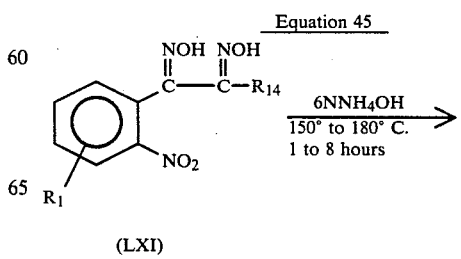

-continued
Equation 45

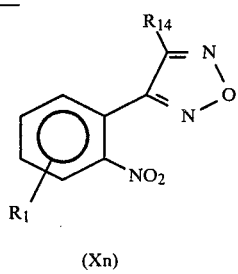

(Xn)

wherein
R₁ is as originally defined; and
R₁₄ is H, CH₃ or C₂H₅.

Equation 46 below illustrates a method for preparing 3-halo-4-(2-nitrophenyl)-1,2,5-oxadiazoles of Formula (Xn′) and 3-alkoxy- and 3-methylthio-4-(2-nitrophenyl)-1,2,5-oxadiazoles of Formula (Xn″).

Equation 46

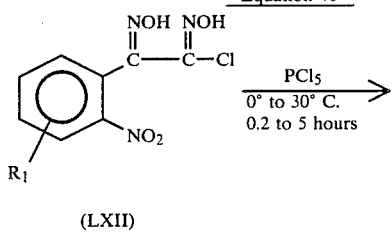

(LXII)

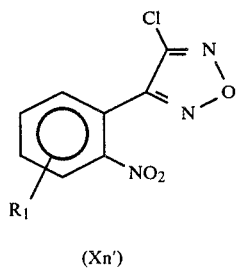

(Xn′)

$(Xn') \xrightarrow[\substack{25° \text{ to } 70° \text{ C.} \\ 0.5 \text{ to } 5 \text{ hours}}]{\text{NaOR}_{14}' \text{ or NaSCH}_3}$ (b)

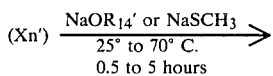

(Xn″)

wherein
R₁ is as originally defined; and
R₁₄′ is CH₃ or C₂H₅.

The reactions of Equation 46 above can be run according to similar procedures described in B. Nash et al., *J. Chem. Soc.*, 2794 (1969). Thus, in reaction 46a, a ω-chloro-(2-nitrophenyl)glyoxime of Formula (LXII) is reacted wih phosphorus pentachloride in a solvent such as ether or toluene at about 0° to 30° C. for 0.2 to 5 hours to form Xn′. In reaction 46b, Xn′ is reacted with sodium methoxide, sodium ethoxide or sodium methylmercaptide in a solvent such as methanol, ethanol or tetrahydrofuran at 25° to 70° C. for 0.5 to 5 hours to form Xn″.

The 2-(2-nitrophenyl)-1,3,4-thiadiazoles of Formula (Xo) in Equation 47 below can be prepared by reacting 2-nitrothiobenzhydrazide LXIII with excess triethylorthoformate at reflux for 1 to 16 hours, according to the teachings of C. Ainsworth, *J. Am. Chem. Soc.*, 77, 1150 (1955).

Equation 47

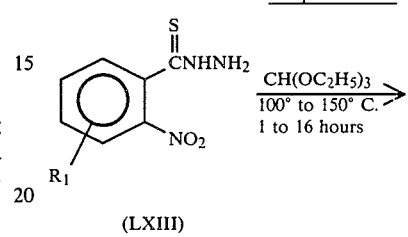

(LXIII)

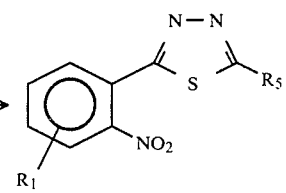

(Xo)

wherein
R₁ is as originally defined.

The 2-alkyl-5-(2-nitrophenyl)-1,3,4-thiadiazoles of Formula (Xo′) in Equation 48 below can be prepared by reacting 2-nitrothiobenzhydrazide LXIII with an appropriate alkylimidate ester HCl in a solvent such as ethanol at 25° to 80° C. for 0.5 to 5 hours, according to the teachings of H. Weidinger and J. Kranz, *Ber.*, 96, 1059 (1963).

Equation 48

$(LXIII) \xrightarrow[\substack{25° \text{ to } 80° \text{ C.} \\ 0.5 \text{ to } 5 \text{ hours}}]{\underset{\|}{R_5-C-OC_2H_5.HCl}}$ 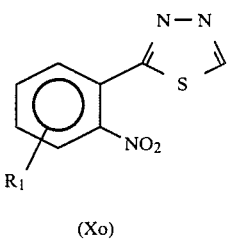

(Xo′)

wherein
R₁ is as originally defined; and
R₅ is CH₃ or C₂H₅.

The 2-methylthio-5-(2-nitrophenyl)-1,3,4-thiadiazoles of Formula (Xo″) in Equation 49 below can be prepared by cyclizing a methyl 3-(2-nitrobenzoyl)dithiocarbazate of Formula (LXIV) in sulfuric acid, polyphosphoric acid, or in benzene with p-toluenesulfonic acid catalyst (p-TsOH), according to the teachings of R. Young and K. Wood, *J. Am. Chem. Soc.*, 77, 400 (1955).

Equation 49

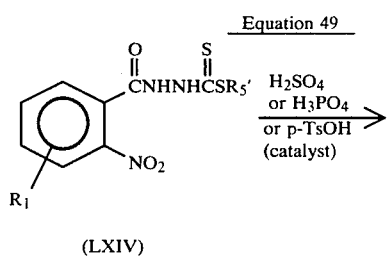

(LXIV)

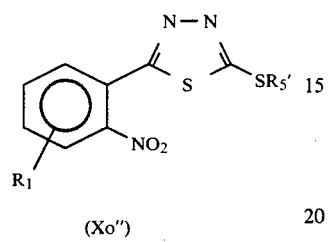

(Xo'')

wherein
$R_1$ is an originally defined; and
$R_5'$ is $CH_3$.

Thus, the reaction of Equation 49 above is run in concentrated sulfuric acid at 0° to 30° C. for 0.1 to 0.5 hour. In polyphosphoric acid, the reaction is run at 50° to 90° C. for 1 to 24 hours. And in benzene with p-TsOH catalyst, the reaction is run at reflux for 1 to 24 hours. The starting compound LXIV is prepared by alkylation with alkyl iodide of the salt formed from an appropriate 2-nitrobenzhydrazide and carbon disulfide in alcoholic potassium hydroxide, according to the method of M. Busch and M. Starke, *J. Prakt. Chem.*, 93, 49 (1916).

Equation 50 below illustrates a method for preparing 2-halo-5-(2-nitrophenyl)-1,3,4-thiadiazoles of Formula (Xo''').

Equation 50

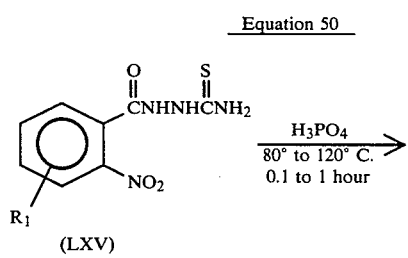

(LXV)

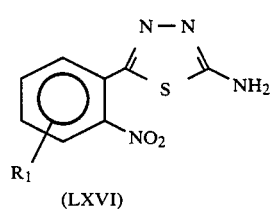

(LXVI)

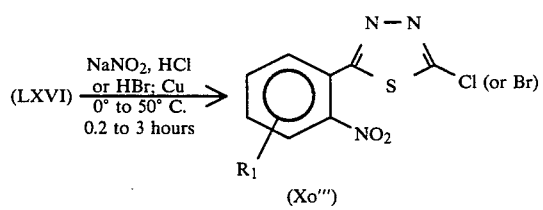

(Xo''')

wherein
$R_1$ is as originally defined.

The reactions of Equation 50 are run by methods known in the art. Thus, in reaction 50a, LXV is cyclized in polyphosphoric acid at 80° to 120° C. for about 0.1 to 1 hour to form a 2-amino-5-(2-nitrophenyl)-1,3,4-thiadiazole of Formula (LXVI), according to the teachings of E. Hoggarth, *J. Chem. Soc.*, 1163 (1949). In reaction 50b, LXVI is transformed to Xo''' by Sandmeyer reactions according to methods described in J. Goerdeler et al., *Chem. Ber.*, 89, 1534 (1956) and A. Alemagna and T. Bacchetta, *Tetrahedron*, 24, 3209 (1968). This requires reacting LXVI with sodium nitrite in hydrochloric or hydrobromic acid in the presence of copper powder at 0° to 50° C. for 0.2 to 3 hours.

Equation 51 below illustrates a method for preparing 2-alkoxy-5-(2-nitrophenyl)-1,3,4-thiadiazoles of Formula (Xo'''').

Equation 51

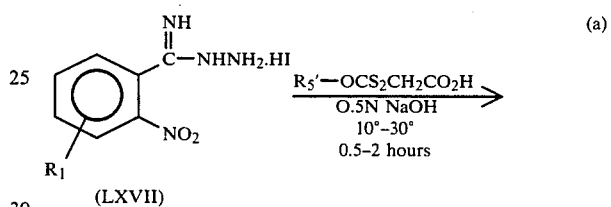

(LXVII)

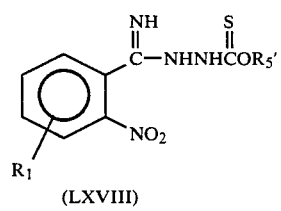

(LXVIII)

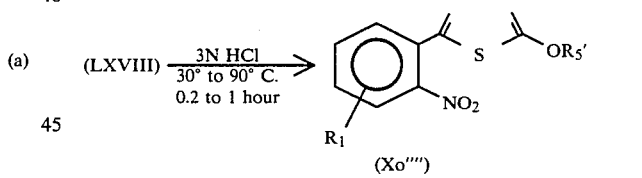

(Xo'''')

wherein
$R_1$ is as originally defined; and
$R_5'$ is $CH_3$ or $C_2H_5$.

The reactions of Equation 51 above can be run according to similar procedures described in K. Doyle and F. Kurzer, *Tetrahedron*, 32, 1031 (1976). Thus, in reaction 51a, a 2-nitrobenzamidrazone.HI of Formula (LXVII) is reacted with an appropriate alkoxythiocarbonylthioacetic acid in 0.5N NaOH at 10° to 30° C. for 0.5 to 2 hours to form a N-(2-nitrobenzimidoyl)-N'-alkoxythiocarbonylhydrazine of Formula (LXVIII). In reaction 51b, LXVIII is cyclized by stirring in 3N HCl at 30° to 90° C. for 0.2 to 2 hours to form Xo''''. The alkoxythiocarbonylthioacetic acids are prepared by known methods, e.g., K. Jensen et al., *Acta Chemica. Scand.*, 23, 1916 (1969).

Equation 52 below illustrates a method for preparing 3-(2-nitrophenyl)-1,2,4-thiadiazoles and 5-chloro-3-(2-nitrophenyl)-1,2,4-thiadiazoles of Formula (Xp).

Equation 52

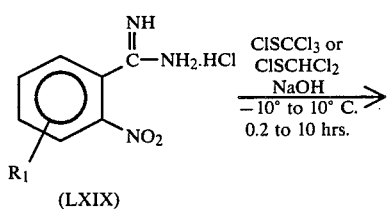

wherein
R₁ is as originally defined; and
R₅ is H or Cl.

The reactions of Equation 52 can be run according to similar procedures described in J. Goerdeler et al., Chem. Ber., 53, 8166 (1959); and J. Goerdeler and M. Budnowski, Chem. Ber., 94, 1682 (1961). Thus, a 2-nitrobenzamidine.HCl of Formula (LXIX) is reacted with perchloromethylmercaptan or dichloromethanesulfenyl chloride and sodium hydroxide in a solvent such as water-methylene chloride or aqueous dioxane at about −10° to 10° C. for 0.2 to 10 hours to form Xp.

The 5-bromo-3-(2-nitrophenyl)-1,2,4-thiadiazoles of Formula (Xp') in Equation 53 below can be prepared from 5-amino-3-(2-nitrophenyl)-1,2,4-thiadiazoles of Formula (LXX) by Sandmeyer reactions, according to the teachings of J. Goerdeler et al., Chem. Ber., 1534 (1956).

Equation 53

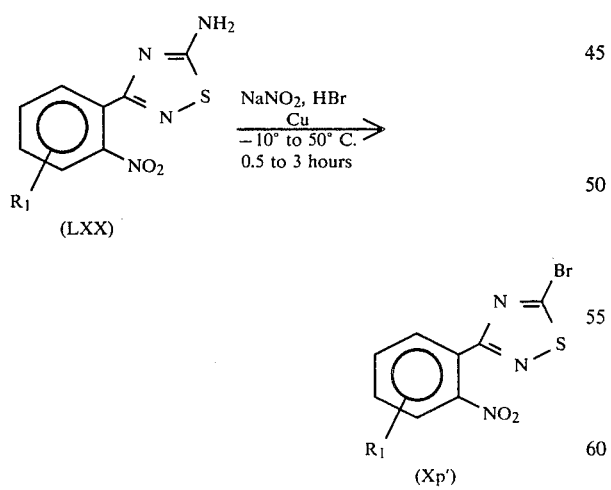

wherein
R₁ is as originally defined.

Thus, according to Equation 53, LXX is reacted with sodium nitrite in hydrobromic acid in the presence of copper powder at −10° to 50° C. for 0.5 to 3 hours to form Xp'. The starting amine LXX can be prepared by reaction of 5-chloro-3-(2-nitrophenyl)-1,2,4-thiadiazoles Xp, described above in Equation 52, with ammonia by standard methods, e.g., F. Kurzer, Adv. in Heterocycl. Chem., 5, 159 (1965).

The 5-alkoxy- and 5-methylthio-3-(2-nitrophenyl)-1,2,4-thiadiazoles of Formula (Xp") in Equation 54 below can be prepared by reacting 5-chloro-3-(2-nitrophenyl)-1,2,4-thiadiazole Xp with sodium methoxide, sodium ethoxide or sodium methylmercaptide in a solvent such as methanol, ethanol or tetrahydrofuran at 10° to 50° C. for 0.5 to 5 hours, according to the teachings of J. Goerdeler et al., Chem. Ber., 90, 182 (1957).

Equation 54

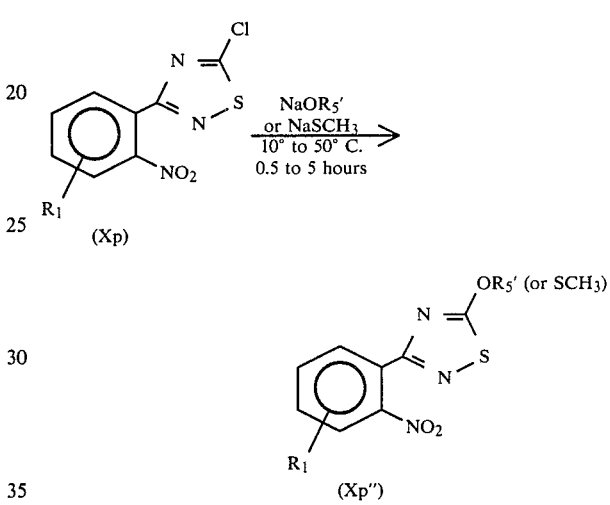

wherein
R₁ is as originally defined; and
R₅' is CH₃ or C₂H₅.

Equation 55 below illustrates a method for preparing 5-alkyl-3-(2-nitrophenyl)-1,2,4-thiadiazoles of Formula (Xp''').

Equation 55

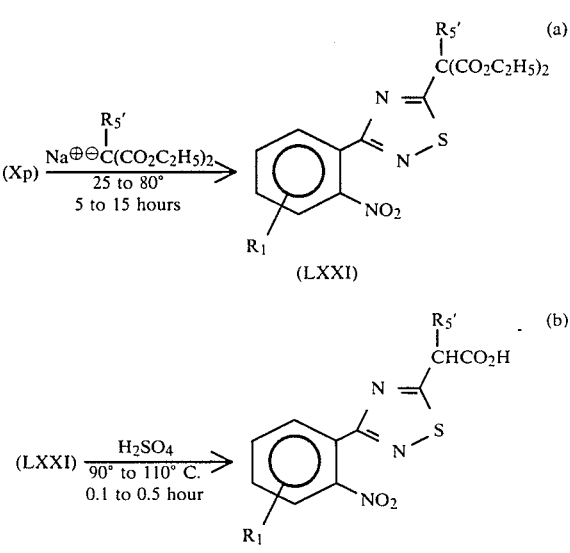

-continued
Equation 55

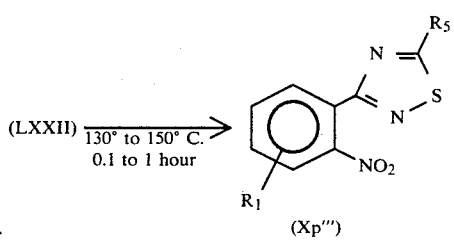

wherein
R$_1$ is as originally defined;
R$_5'$ is H or CH$_3$; and
R$_5$ is CH$_3$ or C$_2$H$_5$.

The reactions of Equation 55 above can be run according to similar procedures described in G. Goerdeler and H. Hammer, *Ber.*, 97, 1134 (1964). Thus, in reaction 55a, 5-chloro-3-(2-nitrophenyl)-1,2,4-thiadiazole Xp is reacted with an appropriate diethyl sodiomalonate in a solvent such as benzene or tetrahydrofuran at reflux for about 5 to 15 hours to form a 5-(substituted)-3-(2-nitrophenyl)-1,2,4-thiadiazole of Formula (LXXI). In reaction 55b, LXXI is deesterified by heating it in aqueous sulfuric acid at 90° to 110° C. for about 0.1 to 0.5 hour to form a 5-carboxymethylene-3-(2-nitrophenyl)-1,2,4-thiadiazole of Formula (LXXII). And in reaction 55c, LXXII is decarboxylated by heating under nitrogen at about 130° to 150° C. for 0.1 to 1 hour to form Xp'''.

Equation 56 below illustrates a method for preparing 5-(2-nitrophenyl)-1,2,4-thiadiazoles of Formula (Xq).

Equation 56

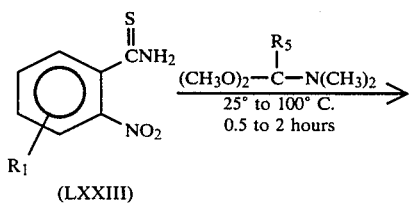

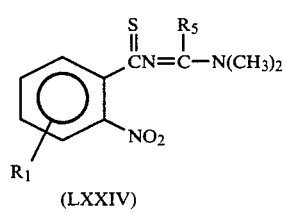

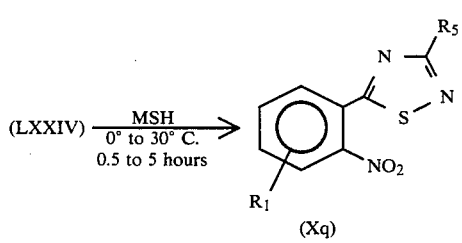

wherein
R$_1$ is as originally defined; and
R$_5$ is H, CH$_3$ or C$_2$H$_5$.

The reactions of Equation 56 above can be run according to similar procedures described in Yang-i Lin et al., *J. Org. Chem.*, 45, 3750 (1980). Thus, in reaction 56a, a 2-nitrobenzothioamide of Formula (LXXIII) is reacted with an appropriate N,N-dimethylalkanamide dimethyl acetal at 25° to 100° C. for 0.5 to 2 hours to form N-[(dimethylamino)methylene]-2-nitrobenzothioamide of Formula (LXXIV). In the second reaction, LXXIV is reacted with O-(mesitylenesulfonyl)hydroxylamine (MSH) in a solvent such as methylene chloride at 0° to 30° C. for 0.5 to 5 hours to form Xq.

Equation 57 below illustrates a method for preparing 3-halo-5-(2-nitrophenyl)-1,2,4-thiadiazoles of Formula (Xq') and 3-alkoxy- and 3-methylthio-5-(2-nitrophenyl)-1,2,4-thiadiazoles of Formula (Xq'').

Equation 57

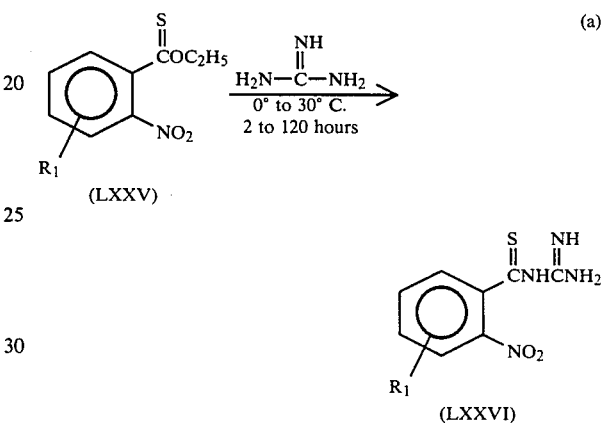

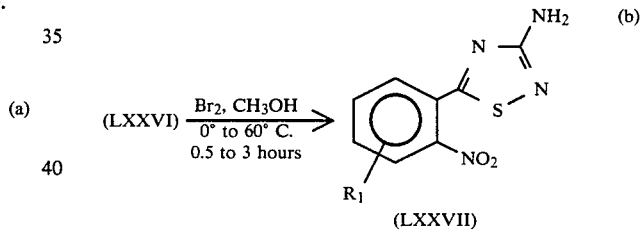

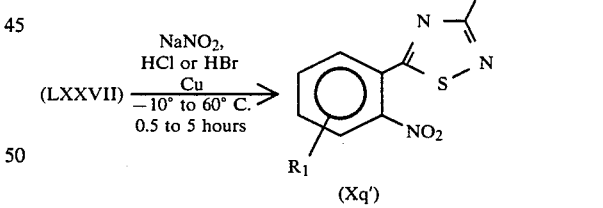

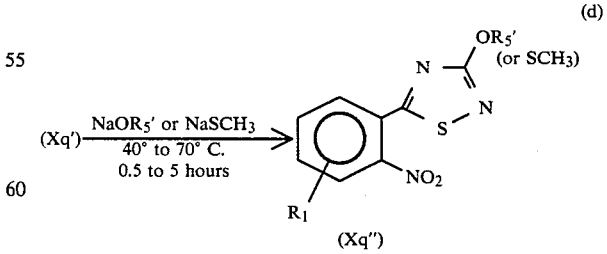

wherein
R$_1$ is as originally defined; and
R$_5'$ is CH$_3$ or C$_2$H$_5$.

The reactions of Equation 57 above can be run by methods known in the art. Thus, in reaction 57a, a 2- nitrothiobenzoate of Formula (LXXV) is reacted with guanidine in a solvent such as ethanol or tetrahydrofuran at 0° to about 30° C. for 2 to 120 hours to form a 2-nitrothiobenzoylguanidine of Formula (LXXVI), according to the teachings of J. Goerdeler and A. Fincke, *Chem. Ber.*, 89, 1033 (1956). In reaction 57b, LXXVI is cyclized by reaction with bromine in methanol at 0° to 60° C. for 0.5 to 3 hours to form a 3-amino-5-(2-nitrophenyl)-1,2,4-thiadiazole of Formula (LXXVII), according to the teachings of ibid. In reaction 57c, LXXVII is reacted with sodium nitrite in hydrochloric acid or hydrobromic acid, in the presence of copper powder, at −10° to 60° C. for 0.5 to 5 hours to form Xq' via Sandmeyer reaction, according to the teachings of F. Kurzer and S. Taylor, *J. Chem. Soc.*, 3234 (1960). And in the last reaction, Xq' is reacted with sodium methoxide, sodium ethoxide or sodium methylmercaptide in a solvent such as methanol, ethanol or tetrahydrofuran at reflux for 0.5 to 5 hours to form Xq'', according to the teachings of ibid.

The 3-(2-nitrophenyl)-1,2,5-thiadiazoles of Formula (Xr) in Equation 58 below can be prepared by nitrating 3-phenyl-1,2,5-thiadiazoles of Formula (LXXVIII) with nitric acid at 0° to 30° C. for 0.2 to 2 hours, according to the teachings of A. de Munno et al., *Int. J. Sulfur Chem.*, Part A, 2, 25 (1972).

Equation 58

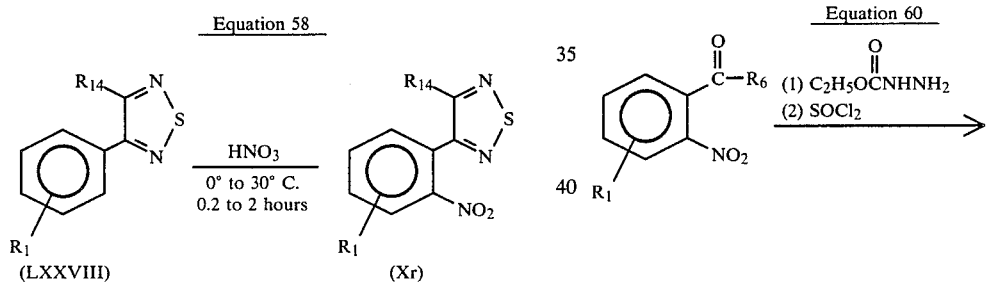

wherein
$R_1$ is as originally defined; and
$R_{14}$ is H, Cl or $CH_3$.

The starting compounds LXXVIII in Equation 58 above can be prepared by known methods. Several such methods are described in L. Weinstock et al., *J. Org. Chem.*, 32, 2823 (1967); S. Mataka et al., *Synthesis*, 7, 524 (1979); V. Bertini and P. Pino, *Angew. Chem. Internat. Edit.*, 5, 514 (1966); and V. Bertini and P. Pino, *Corsi. Semin. Chim.*, 10, 82 (1968).

The 3-alkoxy- and 3-methylthio-4-(2-nitrophenyl)-1,2,5-thiadiazoles of Formula (Xr') in Equation 59 below can be prepared by reacting 3-chloro-4-(2-nitrophenyl)-1,2,5-thiazoles of Formula (Xr) with sodium methoxide, sodium ethoxide or sodium methylmercaptide in a solvent such as methanol, ethanol or tetrahydrofuran at about 0° to 60° C. for 0.5 to 5 hours, according to the teachings of German No. 1,175,683 and L. Weinstock and P. Pollak, *Adv. in Het. Chem.*, 9, 107 (1968).

Equation 59

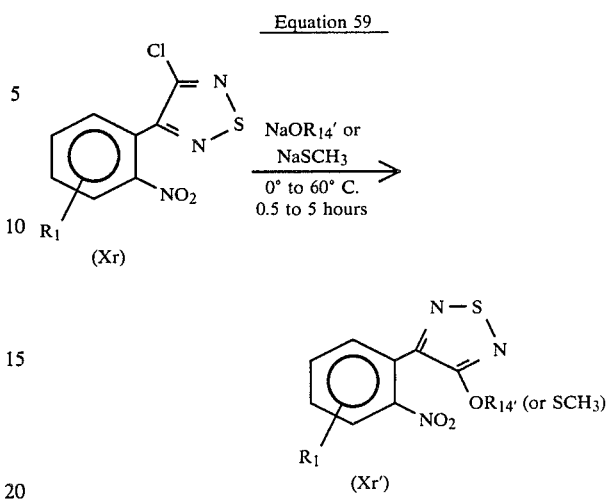

wherein
$R_1$ is as originally defined; and
$R_{14}'$ is $CH_3$ or $C_2H_5$.

The 4-(2-nitrophenyl)-1,2,3-thiadiazoles of Formula (Xs) in Equation 60 below can be prepared according to teachings in U.S. Pat. No. 3,940,407. The method requires reacting an appropriate 2-nitrophenyl alkyl ketone with ethyl carbazate to form the corresponding hydrazide. Subsequent reaction of the hydrazide with thionyl chloride yields Xs.

Equation 60

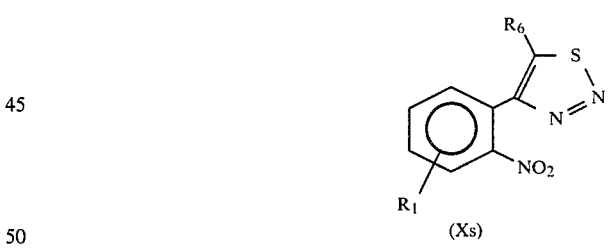

wherein $R_1$ and $R_6$ are as originally defined.

Also, the 5-(2-nitrophenyl)-1,2,3-thiadiazoles f Formula (Xs') in Equation 60a below can be prepared by reacting an appropriate 2-nitrophenylacetaldehyde with ethyl carbazate, followed by cyclizing the hydrazone thus obtained with thionyl chloride according to teachings in U.S. Pat. No. 3,940,407.

Equation 60a

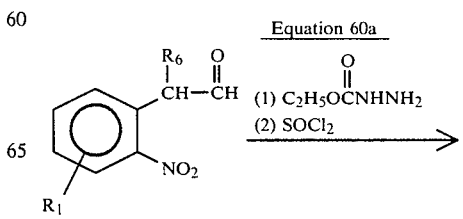

-continued
Equation 60a

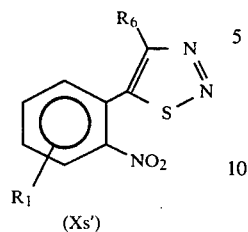

(Xs')

wherein $R_1$ and $R_6$ are as originally defined.

The 1-methyl-5-(2-nitrophenyl)-1H-1,2,4-triazoles of Formula (Xt) in Equation 61 below can be prepared by reacting a N-[(dimethylamino)methylene]-2-nitrobenzamide of Formula (LXXIX) with methylhydrazine in acetic acid at 50° to 90° C. for 0.5 to 2 hours, according to the teachings of Lin et al., *J. Org. Chem.*, 44, 4160 (1979). The starting material LXXIX can be prepared by procedures described above in the first step of Equation 42.

Equation 61

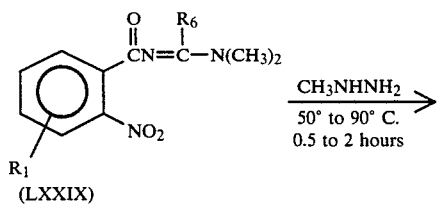

wherein $R_1$ and $R_6$ are as originally defined.

Equation 62 below illustrates a method for preparing 1-methyl-3-(2-nitrophenyl)-1H-1,2,4-triazoles of Formula (Xu).

Equation 62

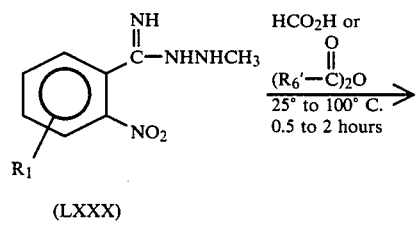

(LXXX)

-continued
Equation 62

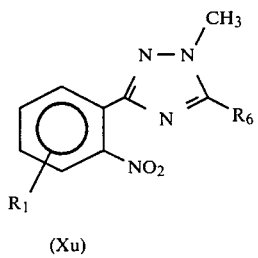

(Xu)

wherein $R_1$ is as originally defined;

$R_6'$ is $CH_3$ or $C_2H_5$; and $R_6$ is H, $CH_3$ or $C_2H_5$.

The reaction of Equation 62 above can be run according to similar procedures described in M. Atkinson and J. Polya, *J. Chem. Soc.*, 3319 (1954). Thus, Xu is prepared by reacting a N-2-nitrobenzimidoyl-N'-methylhydrazine of Formula (LXXX) with formic acid, acetic anhydride or propionic anhydride at about 25° to 100° C. for 0.5 to 1 hour. The starting material LXXX is prepared by reacting an appropriate 2-nitrobenzimidoate HCl with methylhydrazine in pyridine at ambient temperature according to the teachings of ibid.

The 1-(2-nitrophenyl)-1H-1,2,4-pyrazoles of Formula Xv in Equation 63 below can be prepared by reacting a 1-formyl-2-(2-nitrophenyl)hydrazine of Formula (LXXXI) with excess formamide at reflux for about 1 to 6 hours, according to the procedures described in C. Ainsworth et al., *J. Med. Pharm. Chem.*, 5, 383 (1962).

Equation 63

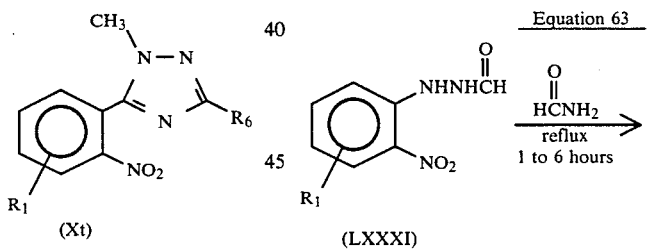

(LXXXI)

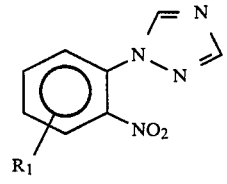

(Xv)

wherein $R_1$ is as originally defined.

The 1-(2-nitrophenyl)-1H-1,2,4-triazoles of Formula (Xv') in Equation 64 below can be prepared by reacting a 2-halo-1-nitrobenzene of Formula (XLVI) with a sodium 1,2,4-triazole salt of Formula (LXXXII). The reaction can be run by procedures described above in Equation 33 by one skilled in the art.

Equation 64

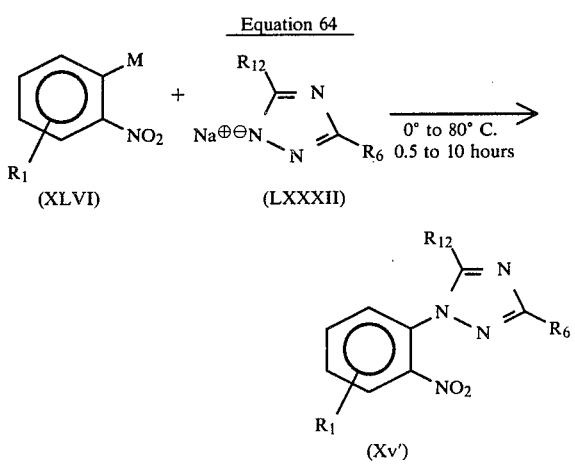

wherein
M is Cl, Br or F; and
$R_1$–$R_{12}$ are as originally defined.

Many 1-(2-nitrophenyl)-1H-1,2,4-triazoles of Formula (Xv') above can also be prepared by the Ullman reaction, according to the teachings of M. Khan and J. Polya, *J. Chem. Soc. C.*, 85 (1970). This requires reacting a 2-halonitrobenzene, such as XLVI above, with an appropriately substituted 1,2,4-triazole, copper (II) oxide catalyst and potassium carbonate in pyridine at reflux for 0.5 to several hours. The product is purified by column chromatography.

Equation 65 below illustrates a method for preparing 4-alkyl-3-(2-nitrophenyl)-4H-1,2,4-triazoles of Formula (Xw).

Equation 65

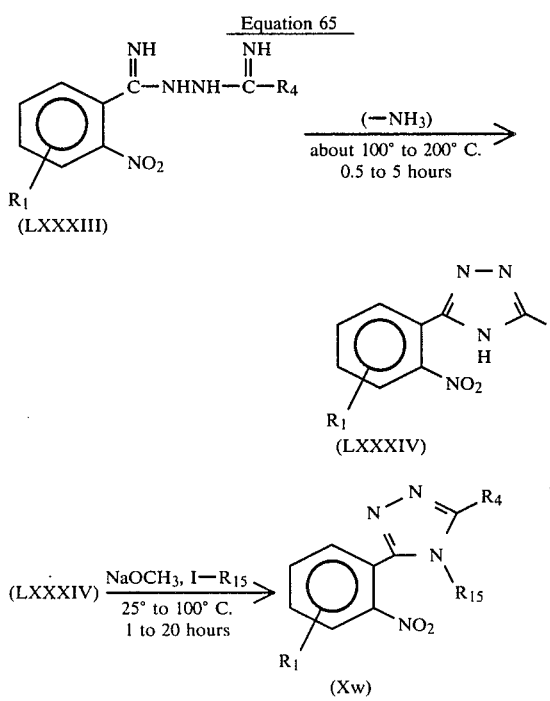

wherein
$R_1$, $R_4$ and $R_{15}$ are as originally defined.

In the reaction of Equation 65a above, a 2-nitrophenyldihydrazidine of Formula (LXXXIII) can be heated at elevated temperatures, i.e. 100° to 200° C., in a solvent such as N-methyl-2-pyrrolidinone to cause cyclization to form a 3-(2-nitrophenyl)-4H-1,2,4-triazole of Formula (LXXXIV), according to methods known in the art, e.g., A. Rusanov, *Russ. Chem. Rev.*, 43, 795 (1974). In reaction 65b, LXXXIV can be alkylated to form Xw. This requires reacting LXXXIV with sodium methoxide followed by an appropriate alkyl iodide in methanol at 25° to 100° C. in a sealed tube for 1 to 20 hours. The product is purified by chromatography procedures.

The 4-(2-nitrophenyl)-4H-1,2,4-triazoles of Formula (Xx) in Equation 66 below can be prepared by reacting a 2-nitroaniline of Formula (LXXXV) with N,N'-diformylhydrazine at 150° to 200° C. for about 0.5 to 2 hours, according to methods known in the art, e.g., C. Ainsworth et al., *J. Med. Pharm. Chem.*, 5, 383 (1962).

Equation 66

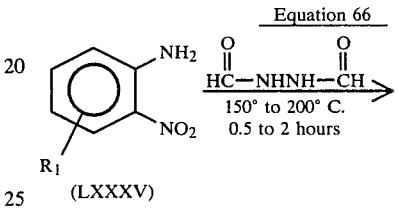

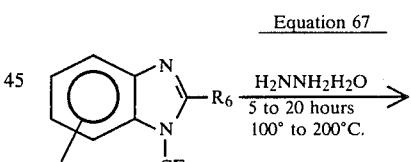

wherein
$R_1$ is as originally defined.

Equation 67 below illustrates a method for preparing 4-(2-aminophenyl)-4H-1,2,4-triazoles of Formula (VIIIc).

Equation 67

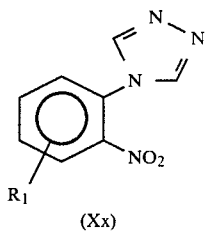

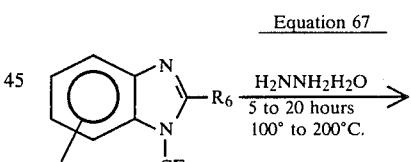

wherein
$R_1$ and $R_6$ are as originally defined.

The reaction of Equation 67 above is run according to similar procedures described in W. Ried and H. Lohwasser, *Justus Liebigs Ann. Chem.*, 699, 88 (1966) and *Angew Chem. Int. Ed. Engl.*, 5, 835 (1966). Thus, N-

(1,1,2-trifluoro-2-chloroethyl)benzimidazole of Formula (LXXXVI) is reacted with excess hydrazine hydrate in ethylene glycol at reflux for 5 to 20 hours to form VIIIc.

The heterocyclic amines of Formula (VII) in Equations 1a and 3 are also important intermediates for the preparation of the compounds of this invention, which can be prepared by the following methods.

The pyrimidines and triazines of Formula (VIIa) to (VIId) below are either known or can be prepared by obvious methods by one skilled in the art. For instance, the synthesis of pyrimidines and triazines of the general formula VIIa has been reviewed in "The Chemistry of Heterocyclic Compounds", a series published by Interscience Publishers, Inc., New York and London. 2-Aminopyrimidines are described by D. J. Brown in "The Pyrimidines", Vol. 16 of this series. 2-Amino-1,3,5-triazines are reviewed by E. M. Smolin and L. Rapaport in "s-Triazines and Derivatives", Vol. 13 of the same series. The synthesis of triazines is also described by F. C. Schaefer, U.S. Pat. No. 3,154,547 and by K. R. Huffman and F. C. Schaefer, *J. Org. Chem.*, 28, 1812 (1963). The synthesis of the bicyclic amines VIIc and VIId are described in EPO Publication No. 15,683, and that of VIIb in European Patent Publication No. 46,677.

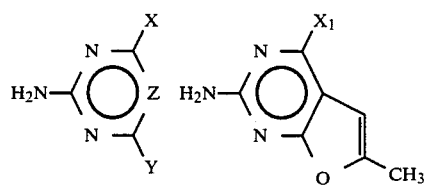

(VIIa)     (VIIb)

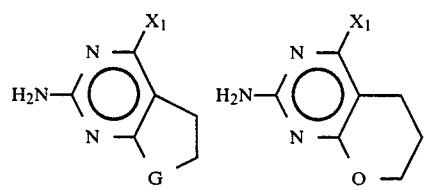

(VIIc)     (VIId)

wherein
G, X, X$_1$, Y and Z are as originally defined

except Y ≠ CH(OCH$_3$)$_2$ or 

Pyrimidines below of Formula (VIIe), where Y is CH(OC$_2$H$_5$)$_2$, are described by W. Braker et al., *J. Am. Chem. Soc.*, 69, 3072 (1947), the disclosure of which is herein incorporated by reference. Using techniques taught by Braker, or suitable modifications that would be obvious to one skilled in the art, the pyrimidines VIIe can be prepared.

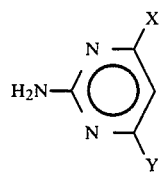

(VIIe)

wherein
X is CH$_3$, OCH$_3$ or Cl; and

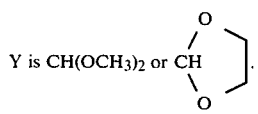

Y is CH(OCH$_3$)$_2$ or

Triazines of Formula (VIIf) may be prepared according to the methods outlined in Equations 68 and 69.

Equation 68

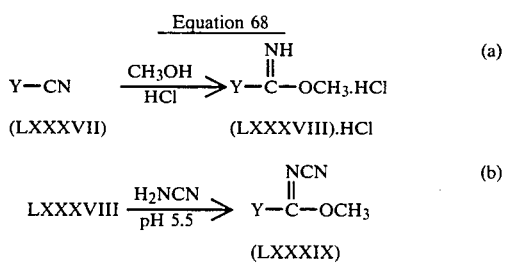

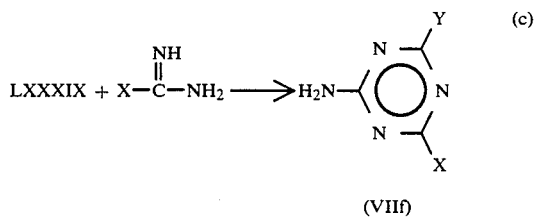

wherein
X is CH$_3$ or OCH$_3$; and
Y is CH(OCH$_3$)$_2$ or

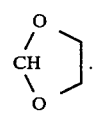

Equation 69

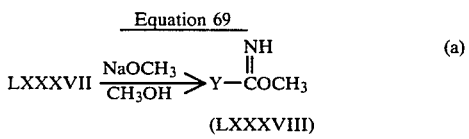

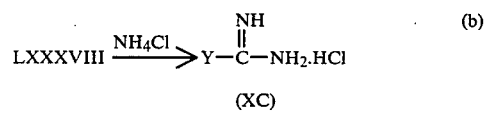

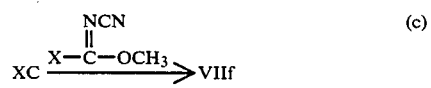

wherein

X and Y are as defined in Equation 68.

The reaction of Equation 68a is carried out according to the teachings of J. M. McElvain and R. L. Clarke, *J. Amer. Chem. Soc.*, 69, 2657 (1947), in which the preparation of ethyl diethoxyiminoacetate is described. The intermediate N-cyanoimidate of Formula (LXXXIX) may be prepared according to the teaching of D. Lwowski in *Synthesis*, 1971, 263, by reacting LXXXVIII with cyanamide at pH 5.5, and this may be condensed according to reaction 68c with either acetamidine or O-methyl isourea in an alcoholic solvent at 25° to 80° C. to provide the appropriate triazines. Alternatively, the reaction of Equation 69a, described for substituted acetonitriles by F. C. Schaefer and G. A. Peters in *J. Org. Chem.*, 26, 412 (1961), may be used to convert nitrile of Formula (LXXXVII) to the corresponding iminoester. The free base may be carried on through reactions 69b and 69c, or, alternatively, converted to the amidinium hydrochloride salt (XC) as described in the aforementioned reference, and condensed with either methyl N-cyanoacetimidate or with dimethyl N-cyano imidocarbonate in the presence of one equivalent of sodium methoxide to provide the triazines of Formula (VIIf).

Cyclic acetals of Formula (VIIh) may also be prepared from compounds of Formula (VIIg) according to Equation 70 by acetal exchange.

Equation 70

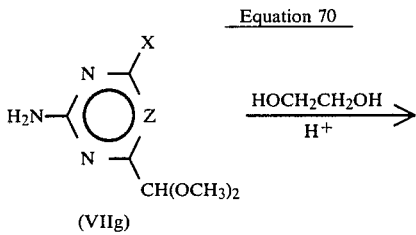

(VIIg)

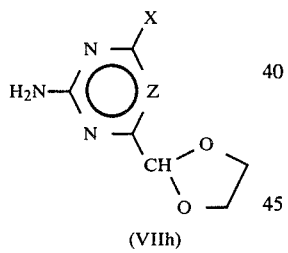

(VIIh)

wherein
X is CH₃ or OCH₃; and
Z is CH or N.

The reaction of Equation 70 is carried out by heating the acyclic acetal in an inert solvent in the presence of one equivalent ethylene glycol and slightly more than one equivalent of a strong acid, such as p-toluenesulfonic acid with removal of the methanol or ethanol formed in the reaction by distillation. The product is isolated by treatment with aqueous base, and extraction with an organic solvent, and purified by crystallization or column chromatography.

Preparations of 3-amino-1,2,4-triazoles of Formula (VII) in Equations 1a and 3 are known in the art and 1,2,4-triazoles are reviewed in *The Chemistry of Heterocyclic Compounds* "Triazoles 1,2,4" (John Wiley and Sons, New York, 1981). Commonly used starting materials containing nitrogen are N-aminoguanidine, hydrazine, alkylhydrazines, cyanamide, ethyl cyanoacetimidate, dimethyl cyanodithioimidocarbonate, dimethyl cyanoimidocarbonate, ethoxymethylenecyanamide, and acylhydrazines. Some literature synthesis are illustrated below. Using these techniques or suitable modifications that would be apparent to one skilled in the art, the 3-amino-1,2,4-triazole intermediates can be readily prepared.

Heating equimolar amounts of ethyl propionimidate hydrochloride and N-aminoguanidine nitrate in pyridine gives 3-amino-5-ethyltriazole; German Pat. No. 1,073,499 (1960); Berichte, 96, 1064 (1963).

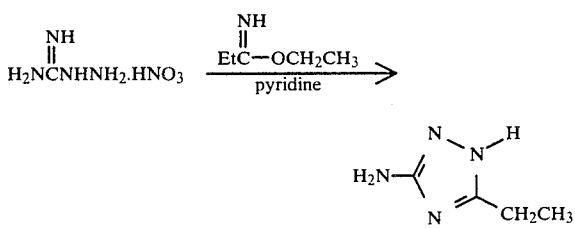

Condensation of hydrazine with ethyl N-cyanoacetimidate yields 3-amino-5-methyltriazole; *Journal of Organic Chemistry*, 28, 1816 (1963).

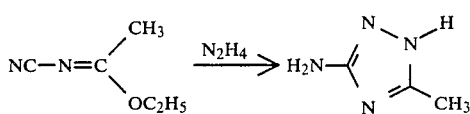

U.S. Pat. No. 2,835,581 (1958) teaches the preparation of 3-amino-5-(hydroxymethyl)triazole from N-aminoguanidine and glycolic acid and British Pat. No. 736,568 (1955) describes the synthesis of 3-amino-5-mercaptotriazole.

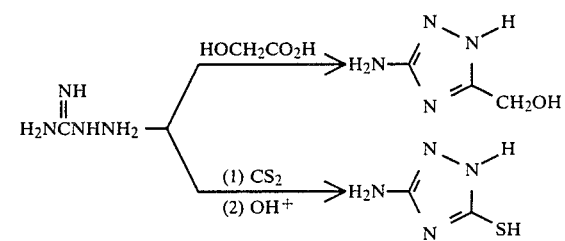

Condensing hydrazine with dimethyl cyanodithioimidocarbonate in acetonitrile gives 3-amino-5-methylthio-1,2,4-triazole while reaction of hydrazine with dimethyl N-cyanoimidocarbonate produces 3-amino-5-methoxy-1,2,4-triazole; *Journal of Organic Chemistry*, 39, 1522 (1974).

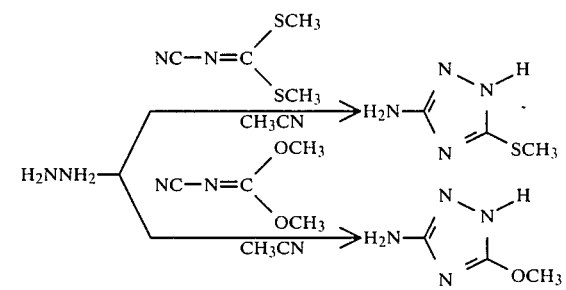

Reaction of substituted hydrazines with N-cyanothioimidocarbonates (prepared according to the procedure given in D. M. Wieland, Ph.D. Thesis, 1971, pp. 123-124) yields disubstituted aminotriazoles as shown below.

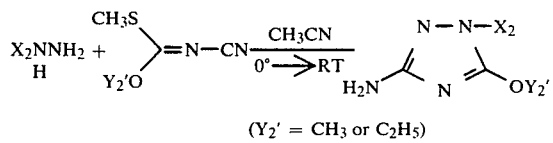

(Y$_2'$ = CH$_3$ or C$_2$H$_5$)

Many of the aminoheterocyclic intermediates of Formula (VII) where R$_{13}$ is methyl may be prepared by a two-step procedure as described for VIIi in Equation 71.

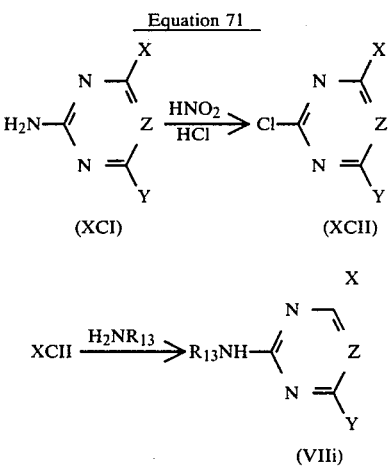

wherein
X, Y and Z are as originally defined and
R$_{13}$ is CH$_3$.

A solution of the amine (XCI) in concentrated hydrochloric acid is treated with sodium nitrite solution and the chloro compound (XCII) is isolated in the usual manner by filtration of the acidic solution. A representative procedure is described by Bee and Rose in *J. Chem. Soc. C*, 2031 (1966), for the case in which Z=CH, and Z=Y=OCH$_3$. Displacement of the chlorine of (XCII) may be accomplished by heating with an excess of methylamine in water to obtain the methylamino heterocycle (VIIi).

Equation 72 below illustrates the preparation of the required methyl pyrimidinyl carbamates and methyl triazinyl carbamates of Formula (III) in Equation 1. By obvious modifications, other methyl carbamates of Formula (III) may be prepared by this method by one skilled in the art.

Equation 72

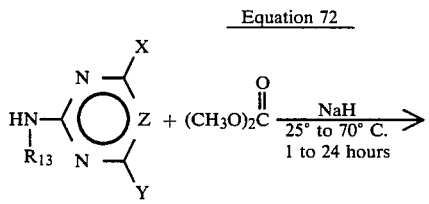

-continued
Equation 72

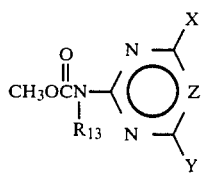

(IIIa)

wherein
X, Y, Z and R$_{13}$ are as originally defined.

According to Equation 72, a heterocyclic amine is reacted with two equivalents of sodium hydride and excess dimethyl carbonate to form IIIa. The reaction is run in an inert solvent such as tetrahydrofuran at 25° C. to reflux for 1 to 24 hours. The product is isolated by (a) adding about two equivalents of concentrated hydrochloric acid under nitrogen at 0° to 30° C.; (b) filtering; and (c) separating out the organic phase, then drying (sodium sulfate and/or magnesium sulfate) and concentrating to dryness in vacuo. The product IIIa may be purified further by recrystallization or chromatography procedures.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation to another. Cationic exchange can be effected by direct treatment of an aqueous solution of a salt of a compound of Formula I (e.g., alkali metal or quaternary amine salt) with a solution containing the cation to be exchanged. This method is most effective with the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and all parts are by weight unless otherwise indicated.

EXAMPLE 1

3-(Dimethylamino)-1-(2-nitrophenyl)-2-propen-1-one

To a solution of 126 g of 2-nitroacetophenone in 125 ml of toluene was slowly added 119 g of N,N-dimethylformamide dimethyl acetal. The solution was refluxed for 16 hours, then concentrated to dryness in vacuo. The solid residue was washed 1×200 ml of 2-propanol and 2×200 ml of hexane to yield 147 g of the title compound; m.p. 118°–121° C.

Anal. Calcd. for $C_{11}H_{12}N_2O_3$: C, 59.9; H, 5.5; N, 12.7. Found: C, 59.4; H, 5.5; N, 12.6.

EXAMPLE 2

5-(2-Nitrophenyl)isoxazole

A suspension containing 99 g of 3-(dimethylamino)-1-(2-nitrophenyl)-2-propen-1-one, prepared in Example 1, and 63 g of hydroxylamine hydrochloride in 250 ml of ethanol was refluxed for 16 hours, then concentrated to dryness in vacuo. Water (400 ml) was added to the residue, and the resulting suspension was filtered. The solid was recrystallized from 2-propanol to give 60 g of the title compound; m.p. 66°–69° C.

Anal. Calcd. for $C_9H_6N_2O_3$: C, 56.8; H, 3.2; N, 14.7. Found: C, 56.3; H, 3.3; N, 14.6.

EXAMPLE 3

5-(2-Aminophenyl)isoxazole

To a suspension containing 206 g of stannous chloride dihydrate in 520 ml of concentrated hydrochloric acid was cautiously added 56 g of 5-(2-nitrophenyl)isoxazole, prepared in Example 2. The resulting suspension was refluxed on a steam bath for about 1 hour, then cooled to 10° C. and filtered. The solid was added to about 600 ml of ice-water, and the suspension was made basic to a pH of about 10 with addition of 50% NaOH. The aqueous mixture was extracted with methylene chloride. After drying the methylene chloride extract over sodium sulfate, the solvent was evaporated under reduced pressure to give 32 g of the title compound as an oil.

Anal. Calcd. for $C_9H_8N_2O$: C, 67.5; H, 5.1; N, 17.5. Found: C, 67.1; H, 5.1; N, 17.3.

EXAMPLE 4

2-(Isoxazol-5-yl)benzenesulfonyl chloride

A diazionium salt was prepared by adding a solution of 14.5 g of sodium nitrite in 30 ml of water to a suspension of 32 g of 5-(2-aminophenyl)isoxazole, prepared in Example 3, and 72 ml of concentrated hydrochloric acid in 210 ml of glacial acetic acid cooled at 0° to 5° C. After stirring about 0.4 hour, the diazonium salt suspension was poured in one portion into a mixture consisting of 150 ml of acetic acid, 8.4 g of cupric chloride dihydrate and 60 ml of sulfur dioxide and cooled at 10° C. by an ice-water bath. The mixture was stirred at 10° to 15° C. for 0.2 hour then at about 20° to 30° C. for 3 hours. The suspension was poured into ice-water (about 700 ml) and stirred to form a solid. The mixture was filtered and the solid was washed 3×100 ml of water and suction dried to give 37 g of crude 2-(isoxazol-5-yl)benzenesulfonyl chloride; m.p. 63°–65° C.

EXAMPLE 5

2-(Isoxazol-5-yl)benzenesulfonamide

A solution of 37 g of 2-(isoxazol-5-yl)benzenesulfonyl chloride, prepared in Example 4, in 200 ml of tetrahydrofuran, was cooled in an ice-water bath while about 40 ml of concentrated aqueous ammonium hydroxide was added slowly at 10° to 30° C. The resulting suspension was stirred at room temperature for 4 hours, then the solvent was evaporated under reduced pressure. The residue was stirred in 150 ml of water for 0.5 hour, then filtered. The crude, wet solid was dissolved in tetrahydrofuran and dried over sodium sulfate. The solid was recrystallized from 2-propanol to give 20 g of the title compound; m.p. 132°–135° C.

Anal. Calcd. for $C_9H_8N_2O_3S$: C, 48.1; H, 3.6; N, 12.5. Found: C, 47.9; H, 3.6; N, 12.5.

EXAMPLE 6

N-(Butylaminocarbonyl)-2-(isoxazol-5-yl)benzenesulfonamide

A solution of 8.7 g of 2-(isoxazol-5-yl)benzenesulfonamide prepared in Example 5, 4.7 g of n-butyl isocyanate and 5.4 g of potassium carbonate in 125 ml of 2-butanone was refluxed for 7 hours. The resulting suspension was concentrated to dryness in vacuo. The residue was taken up in 200 ml of water and extracted once with 100 ml of ethyl ether. The aqueous layer was acidified with 2N HCl and the resulting suspension was extracted with methylene chloride. After drying the methylene chloride extract over sodium sulfate, the solvent was evaporated off under reduced pressure. The solid residue was recrystallized from acetonitrile to give 10 g of the title compound; m.p. 110°–113° C.

Anal. Calcd. for $C_{14}H_{17}N_3O_4S$: C, 51.9; H, 5.3; N, 12.9. Found: C, 51.2; H, 5.3; N, 12.6.

EXAMPLE 7

2-(Isoxazol-5-yl)benzenesulfonyl isocyanate

A suspension of 6 g of N-(butylaminocarbonyl)-2-(isoxazol-5-yl)benzenesulfonamide, prepared in Example 6, in 50 ml of xylene containing 0.2 g of DABCO was heated at 130°–135° C. while 1.6 ml of phosgene was added portionwise at a rate to maintain a reflux temperature of 130°–135° C. The mixture was refluxed for an additional 2 hours, cooled under nitrogen to room temperature, filtered, and the filtrate was concentrated to dryness in vacuo. A sample of the crude oily product displayed a characteristic sulfonyl isocyanate band in the IR at 2200 cm$^{-1}$.

EXAMPLE 8

N-[(4,6-Dimethoxypyrimidin-2-yl)aminocarbonyl]-2-(isoxazol-5-yl)benzenesulfonamide To a suspension of 2.5 g of 2-amino-4,6-dimethoxypyrimidine in 25 ml of acetonitrile was added 4 g of crude 2-(isoxazol-5-yl)benzenesulfonyl isocyanate prepared in Example 7. The resulting suspension was warmed at 40° C. for about 3 minutes to form a solution. The solution was stirred at room temperature for 10 hours, then concentrated in vacuo to give a viscous oil. The oil was chromatographed in a dry column of silica gel with ethyl acetate as eluant. The first fraction from the column was concentrated in vacuo to yield a solid. The solid was washed 1×10 ml of acetonitrile and suction dried to yield 0.5 g of the title compound; m.p. 183°–187° C. The IR spectrum showed a carbonyl absorption at 1710 cm$^{-1}$ indicative of a sulfonylurea.

Anal. Calcd. for $C_{16}H_{15}N_5O_6S$: C, 47.4; H, 3.7. Found: C, 47.1; H, 3.9.

EXAMPLE 9

Methyl (4,6-dimethoxypyrimidin-2-yl)carbamate

2-Amino-4,6-dimethoxypyrimidine (56 g) was added portionwise to 50% sodium hydride (42.8 g) in 1000 ml of dry tetrahydrofuran. After stirring for 0.5 hour, dimethylcarbonate (58.5 g) was added dropwise with cooling. The mixture was stirred under nitrogen for about 16 hours at ambient temperature. Concentrated HCl (80 ml) was added slowly as external cooling was used to maintain a pot temperature of about 25° C. Saturated aqueous sodium chloride (80 ml) was then added. The solvents were decanted from the precipitated solids and dried over sodium sulfate. Filtering and evaporating the solvents afforded the crude material which was recrystallized from hexane to yield 54 g of the title compound, m.p. 81°-83° C. The IR spectrum showed characteristic absorption bands at 3400 and 1760 cm$^{-1}$.

EXAMPLE 10

4-(2-Nitrophenyl)isoxazole

A suspension of 75 g of 3-(dimethylamino)-2-(2-nitrophenyl)acrolein [prepared by the procedure of U. Hengartner et al., *J. Org. Chem.*, 44, 3748 (1979)] and 47.3 g of hydroxylamine hydrochloride in 300 ml of ethanol was refluxed for 10 hours, then concentrated to dryness in vacuo. Water (400 ml) was added to the residue and the suspension filtered. The isolated solid was recrystallized from 2-propanol to yield 56 g of the title compound; m.p. 51°-54° C.

Anal. Calcd. for $C_9H_6N_2O_3$: C, 56.8; H, 3.2; N, 14.7. Found: C, 56.6; H, 3.1; N, 14.4.

EXAMPLE 11

4-(2-Aminophenyl)isoxazole

To a suspension of 108 g of stannous chloride dihydrate in 270 ml of concentrated hydrochloric acid was added portionwise 30 g of 4-(2-nitrophenyl)isoxazole prepared in Example 10 at less than 30° C. The suspension was stirred at about 20°-35° C. for 10 hours, then cooled to 10° C. and filtered. The solid was added to ice-water (400 ml), 50% NaOH was added to make the suspension basic to a pH of about 10, and the resultant suspension filtered. The solid was washed 3×100 ml of water and suction dried to give 18 g of the title compound; m.p. 48°-51° C.

Anal. Calcd. for $C_9H_8N_2O$: C, 67.5; H, 5.1; N, 17.5. Found: C, 67.1; H, 5.1; N, 17.2.

EXAMPLE 12

2-(Isoxazol-4-yl)benzenesulfonyl chloride

By the procedure of Example 4, a diazonium salt was prepared by reacting 12 g of 4-(2-aminophenyl)isoxazole prepared in Example 11 with 5.5 g of sodium nitrite and 27 ml of concentrated hydrochloric acid in 80 ml of glacial acetic acid. The diazonium salt suspension was added to a suspension of 3.2 g cupric chloride dihydrate and 23 ml of sulfur dioxide in 57 ml of glacial acetic acid to give, after addition of excess water and filtration and suction drying, 15 g of the title compound as a crude solid; m.p. 100°-104° C.

EXAMPLE 13

2-(Isoxazol-4-yl)benzenesulfonamide

By the procedure of Example 5, 15 g of 2-(isoxazol-4-yl)benzensulfonyl chloride prepared in Example 12 was reacted with 30 ml of concentrated ammonium hydroxide in 150 ml of tetrahydrofuran to give, after recrystallization from 2-propanol, 11 g of the title compound; m.p. 165°-167° C.

Anal. Calcd. for $C_9H_8N_2O_3S$: C, 48.2; H, 3.6; N, 12.5. Found: C, 47.8; H, 3.7; N, 12.7.

EXAMPLE 14

N-[(4,6-Dimethoxypyrimidin-2-yl)aminocarbonyl]-2-(isoxazol-4-yl)benzenesulfonamide A solution of 2 g of 2-(isoxazol-4-yl)benzenesulfonamide, prepared in Example 13, in 100 ml of methylene chloride was purged with nitrogen. To the solution was added carefully 0.8 g of trimethylaluminum (5.5 ml of 2M solution in toluene) while cooling the flask at 15° to 30° C. After stirring about 0.2 hour, 1.9 g of methyl (4,6-dimethoxypyrimidin-2-yl)carbamate, prepared in Example 9, was added and the suspension was refluxed for 20 hours under a nitrogen atmosphere. The suspension was cooled in an ice-water bath while 50 ml of 25% aqueous acetic acid was carefully added. Excess water was added and the organic phase was separated and dried over sodium sulfate. After evaporation of the solvent in vacuo, the residue was triturated with 25 ml of ethyl acetate to give 0.5 g of the title compound; m.p. 175°-178° C.

Anal. Calcd. for $C_{16}H_{15}N_5O_6S$: C, 47.4; H, 3.7; N, 17.3. Found: C, 46.8; H, 3.7; N, 17.2.

EXAMPLE 15

N-[(4,6-Dichloro-1,3,5-triazin-2-yl)aminocarbonyl]-2-(isoxazol-4-yl)benzenesulfonamide To 4.5 g of 2-(isoxazol-4-yl)benzenesulfonamide prepared in Example 13 in 20 ml of acetonitrile is added 4 g of dichloro-5-triazinyl isocyanate. The mixture is refluxed for 2 hours, then is cooled to room temperature and filtered. The resulting solid is washed with diethyl ether to give N-[(4,6-dichloro-1,3,5-triazin-2-yl)aminocarbonyl]-2-(isoxazol-4-yl)benzenesulfonamide.

EXAMPLE 16

N-[(4,6-Dimethoxy-1,3,5-triazin-2-yl)aminocarbonyl]-2-(isoxazol-4-yl)benzenesulfonamide To 1 g of sulfonamide prepared in Example 15 in 10 ml of methanol is added portionwise 0.41 g of sodium methoxide. After an initial exotherm, the suspension is stirred at 25° to 50° C. for about 1 hour, then cooled to room temperature and diluted with excess water (about 30 ml). The solution is acidified to a pH of about 1 with concentrated HCl. The resulting mixture is filtered and suction dried to give the title compound.

EXAMPLE 17

1-Methyl-4-(2-nitrophenyl)-1H-pyrazole

A solution of 60 g of 3-(dimethylamino)-2-(2-nitrophenyl)acrolein (see Example 10) and 16.1 g of methylhydrazine in 200 ml of toluene was refluxed for 10 hours, then concentrated to dryness in vacuo. The residue was recrystallized from 1-chlorobutane/hexane (about 1:1) to yield 51 g of the title compound; m.p. 41°-44° C.

EXAMPLE 18

1-Methyl-4-(2-aminophenyl)-1H-pyrazole

By the procedure of Example 3, 25 g of 1-methyl-4-(2-nitrophenyl)-1H-pyrazole prepared in Example 17 was reacted with 81.2 g of stannous chloride dihydrate in 200 ml concentrated HCl at reflux for 1 hour to yield, after similar work up, 18 g of the title compound as an oil.

Anal. Calcd. for: $C_{10}H_{11}N_3$: C, 69.3; H, 6.4; N, 24.2. Found: C, 68.8; H, 6.2; N, 23.9.

EXAMPLE 19

2-(1-Methyl-1H-pyrazol-4-yl)benzenesulfonamide

By the procedure of Example 4, 17.3 g of 1-methyl-4-(2-aminophenyl)-1H-pyrazole prepared in Example 18 was diazotized with 7.2 g of sodium nitrite and 36 ml of concentrated HCl in 104 ml of glacial acetic acid. The diazonium salt suspension was added to a suspension containing 4.3 g of cupric chloride dihydrate, 30 ml of sulfur dioxide and 76 ml of acetic acid. After completion of the reaction and addition of water, the suspension was extracted with 1-chlorobutane. The extraction was dried over sodium sulfate and concentrated in vacuo at less than 40° C. to yield 22 g of crude 2-(1-methyl-1H-pyrazol-4-yl)benzenesulfonyl chloride as an oil.

By the procedure of Example 5, 21 g of the above oil was reacted with 30 ml of concentrated $NH_4OH$ in 150 ml of tetrahydrofuran to yield a solid. The solid was recrystallized from acetonitrile to yield 17 g of 2-(1-methyl-1H-pyrazol-4-yl)benzenesulfonamide; m.p. 183°–186° C.

Anal. Calcd. for $C_{10}H_{11}N_3O_2S$: C, 50.6; H, 4.7; N, 17.7. Found: C, 50.8; H, 4.7; N, 18.0.

EXAMPLE 20

N-[(4-Methoxy-6-methyl-1,3,5-triazin-2-yl)aminocarbonyl]-2-(1-methyl-1H-pyrazol-4-yl)benzenesulfonamide By the procedure of Example 14, 2 g of 2-(1-methyl-1H-pyrazol-4-yl)benzenesulfonamide, prepared in Example 19, was reacted in 100 ml of methylene chloride with 0.7 g of trimethylaluminum (5 ml of 2M toluene solution) followed by 1.7 g of methyl (4-methoxy-6-methyl-1,3,5-triazin-2-yl)carbamate. After work up and evaporation of the methylene chloride solvent, the residue was triturated with ethyl acetate to yield 0.6 g of the title compound; m.p. 221°–224° C. The IR spectrum showed a carbonyl absorption at 1700 cm$^{-1}$ indicative for a sulfonylurea.

EXAMPLE 21

N-[2-[3-(Dimethylamino)-1-oxo-2-propenyl]phenyl]acetamide

A suspension of 48 g of N-[2-(1-oxo-1-ethanyl)-phenyl]acetamide and 38 g of N,N-dimethylformamide dimethyl acetal in 150 ml of toluene was heated at reflux for about 16 hours, then concentrated in vacuo to a solid. The solid was recrystallized from 1-chlorobutane to yield 40 g of the title compound; m.p. 90°–95° C.

Anal. Calcd. for $C_{13}H_{16}N_2O_2$: C, 67.2; H, 6.9; N, 12.0. Found: C, 66.8; H, 6.8; N, 11.7.

EXAMPLE 22

N-[2-(1- and/or 2-methyl-1H-pyrazol-3-yl)phenyl]acetamide

A suspension of 40 g of N-[2-[3-(dimethylamino)-1-oxo-2-propenyl]phenyl]acetamide prepared in Example 21 and 9.2 g of methylhydrazine in 130 ml of ethanol was heated at reflux for 10 hours, then concentrated in vacuo. The residue was recrystallized from 1-chlorobutane to yield 30 g of the title compound; m.p. 102°–106° C.

Anal. Calcd. for $C_{12}H_{13}N_3O$: C, 66.9; H, 6.1; N, 19.5. Found: C, 66.0; H, 6.0; N, 18.5.

EXAMPLE 23

1- and/or 2-Methyl-1H-3-(2-aminophenyl)pyrazole

A suspension of 30 g of the acetamide prepared in Example 22 in 75 ml of concentrated HCl was stirred and heated at reflux for 1 hour, then cooled to 10° C. and filtered. The solid isolated was added to about 300 ml of ice-water, and the solution was made basic to a pH of about 8 by addition of 50% NaOH to yield an oil. After extracting the aqueous suspension with diethyl ether, the ether extract was concentrated in vacuo to yield an oil that solidified on cooling. The solid was recrystallized from 1-chlorobutane to yield 20 g of the title compound; m.p. 82°–86° C.

Anal. Calcd. for $C_{10}H_{11}N_3$: C, 69.3; H, 6.4; N, 24.2. Found: C, 69.0; H, 6.3; N, 23.9.

EXAMPLE 24

2-(1- and/or 2-Methyl-1H-pyrazol-3-yl)benzenesulfonamide

By the procedure of Example 4, 20 g of amine prepared in Example 23 was diazotized with 8.4 g of sodium nitrite and 42 ml of concentrated HCl in 118 ml of glacial acetic acid. The diazonium salt suspension was added to a suspension containing 4.9 g of cupric chloride dihydrate, 36 ml of sulfur dioxide and 89 ml of acetic acid. After completion of reaction and addition of water, a precipitate formed. The mixture was filtered and the solid obtained was dissolved in methylene chloride and dried over sodium sulfate. Concentration of the methylene chloride solution in vacuo yielded 27 g of crude 2-(1- and/or 2-methyl-1H-pyrazol-3-yl)benzenesulfonyl chloride; m.p. 108°–115° C.

By the procedure of Example 5, 27 g of the above solid was reacted with about 40 ml of concentrated $NH_4OH$ in 200 ml of tetrahydrofuran to yield a solid after work up. The solid was recrystallized from 2-propanol to yield 17 g of the title compound; m.p. 174°–177° C.

Anal. Calcd. for $C_{10}H_{11}N_3O_2S$: C, 50.6; H, 4.7; N, 17.7. Found: C, 50.5; H, 4.6; N, 17.6.

EXAMPLE 25

N-[(4,6-Dimethoxypyrimidin-2-yl)aminocarbonyl]-2-(1- and/or 2-methyl-1H-pyrazol-3-yl)benzenesulfonamide By the procedure of Example 14, 2 g of the sulfonamide prepared in Example 24, was reacted with 0.7 g of trimethylaluminum (4.8 ml of 2M toluene solution) and 1.6 g of methyl (4,6-dimethoxypyrimidin-2-yl)carbamate in 100 ml of methylene chloride under a nitrogen atmosphere. After evaporation of the methylene chloride solvent in vacuo, the residue was recrystallized from acetonitrile to yield 0.8 g of the title compound; m.p. 210°–212° C.

Anal. Calcd. for $C_{17}H_{18}N_6O_5S$: C, 48.8; H, 4.3; N, 20.1. Found: C, 49.4; H, 4.5; N, 21.4.

EXAMPLE 26

2-(1H-Pyrazol-1-yl)benzenesulfonamide

A. To a solution of 52 g of 1-(2-bromophenyl)-pyrazole in 230 ml of diethyl ether under a nitrogen atmosphere and cooled at −70° C. was added dropwise 175 ml of a 1.6M solution of n-butyl lithium in hexane. The suspension was allowed to warm from −70° C. to −25° C. on its own, then a solution of 37 ml of sulfuryl chloride in 69 ml of hexane was added dropwise at −25° to −20° C. After allowing the suspension to warm to room temperature, the suspension was stirred for 5 hours, then filtered to yield 38 g of crude 2-(1H-pyrazol-1-yl)benzenesulfonyl chloride which was contaminated with inorganic salts.

B. To a suspension of the above solid in 200 ml of tetrahydrofuran cooled at 10°-20° C. with an ice bath was added dropwise 50 ml of concentrated aqueous ammonium hydroxide. After adding 25 ml of water to dissolve the salts present, the suspension was stirred at 25° C. for 10 hours, then concentrated in vacuo. After adding water to the residue, the mixture was filtered and the residue was recrystallized from 2-propanol to yield 11.2 g of the title compound; m.p. 167°-170° C.

Anal. Calcd. for $C_9H_9N_3O_2S$: C, 48.4; H, 4.1; N, 18.8. Found: C, 48.1; H, 4.1; N, 18.9.

NMR (CDCl$_3$-DMSO)δ: 6.5 (t, 1H, NC=CHC=N); 7.3 (br, 2H, SO$_2$NH$_2$); and 7.3-8.2 (m, 6H, arom-NCH=C—CHN).

EXAMPLE 27

N-[(4-Methoxy-6-methylpyrimidin-2-yl)aminocarbonyl]-2-(1H-pyrazol-1-yl)benzenesulfonamide By the procedure of Example 14, 1.3 g of the sulfonamide prepared in Example 26 was reacted in 100 ml of methylene chloride with 0.5 g of trimethylaluminum (3.5 ml of 2M toluene solution) followed by 1.3 g of methyl (4-methoxy-6-methylpyrimidin-2-yl)carbamate. After work-up and evaporation of the methylene chloride solvent, the residue was triturated with warm ethyl acetate to yield 1 g of the title compound; m.p. 200°-204° C.

Anal. Calcd. for $C_{16}H_{16}N_6O_4S$: C, 49.5; H, 4.2; N, 21.6. Found: C, 48.8; H, 4.2; N, 21.3.

Using the techniques described in Equations 1 to 72 and Examples 1 to 27, or simple modifications thereof, the following compounds in Tables I–VII can be made by one skilled in the art.

TABLE I

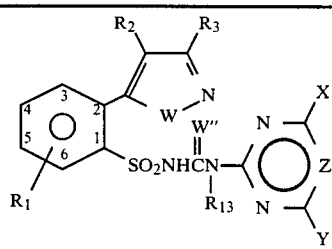

| R$_1$ | R$_2$ | R$_3$ | R$_{13}$ | X | Y | Z | W | W'' | m.p. (°C.) |
|---|---|---|---|---|---|---|---|---|---|
| H | H | H | H | CH$_3$ | CH$_3$ | CH | O | O | 180–185° |
| H | H | H | H | CH$_3$ | OCH$_3$ | CH | O | O | 185–189° |
| H | H | H | H | CH$_3$ | CH$_3$ | N | O | O | 183–185° |
| H | H | H | H | CH$_3$ | OCH$_3$ | N | O | O | 164–172° |
| H | H | H | H | OCH$_3$ | OCH$_3$ | N | O | O | 168–173° |
| H | H | H | H | CH$_3$ | CH$_3$ | CH | S | O | |
| H | H | H | H | OCH$_3$ | CH$_3$ | CH | S | O | |
| H | H | H | H | OCH$_3$ | OCH$_3$ | CH | S | O | |
| H | H | H | H | CH$_3$ | CH$_3$ | N | S | O | |
| H | H | H | H | OCH$_3$ | CH$_3$ | N | S | O | |
| H | H | H | H | OCH$_3$ | OCH$_3$ | N | S | O | |
| 5-F | H | H | H | OCH$_3$ | OCH$_3$ | CH | O | O | |
| 6-Cl | H | H | H | OCH$_3$ | OCH$_3$ | CH | O | O | |
| 4-Br | H | H | H | OCH$_3$ | OCH$_3$ | CH | O | O | |
| 3-CH$_3$ | H | H | H | CH$_3$ | OCH$_3$ | N | O | O | |
| 5-CF$_3$ | H | H | H | OCH$_3$ | OCH$_3$ | N | O | O | |
| 5-OCH$_3$ | H | H | H | OCH$_3$ | OCH$_3$ | CH | O | O | |
| H | H | H | CH$_3$ | OCH$_3$ | OCH$_3$ | CH | O | O | |
| H | H | H | CH$_3$ | OCH$_3$ | CH$_3$ | N | O | O | |
| H | CH$_3$ | H | H | OCH$_3$ | OCH$_3$ | CH | O | O | |
| H | CH$_3$ | H | H | CH$_3$ | OCH$_3$ | CH | O | O | |
| H | CH$_3$ | H | H | CH$_3$ | CH$_3$ | CH | O | O | |
| H | CH$_3$ | H | H | CH$_3$ | OCH$_3$ | N | O | O | |
| H | C$_2$H$_5$ | H | H | OCH$_3$ | OCH$_3$ | CH | O | O | |
| H | C$_2$H$_5$ | H | H | CH$_3$ | OCH$_3$ | CH | O | O | |
| H | C$_2$H$_5$ | H | H | CH$_3$ | CH$_3$ | CH | O | O | |
| H | C$_2$H$_5$ | H | H | OCH$_3$ | CH$_3$ | N | O | O | |
| H | Cl | H | H | OCH$_3$ | OCH$_3$ | CH | O | O | |
| H | Br | H | H | OCH$_3$ | OCH$_3$ | CH | O | O | |
| H | H | CH$_3$ | H | OCH$_3$ | OCH$_3$ | CH | O | O | |
| H | H | CH$_3$ | H | CH$_3$ | OCH$_3$ | CH | O | O | |
| H | H | CH$_3$ | H | CH$_3$ | CH$_3$ | CH | O | O | |
| H | H | CH$_3$ | H | OCH$_3$ | CH$_3$ | N | O | O | |
| H | H | C$_2$H$_5$ | H | OCH$_3$ | OCH$_3$ | CH | O | O | |
| H | H | C$_2$H$_5$ | H | CH$_3$ | OCH$_3$ | CH | O | O | |
| H | H | C$_2$H$_5$ | H | CH$_3$ | CH$_3$ | CH | O | O | |
| H | H | C$_2$H$_5$ | H | CH$_3$ | OCH$_3$ | N | O | O | |
| H | H | Cl | H | OCH$_3$ | OCH$_3$ | CH | S | O | |
| H | H | Br | H | OCH$_3$ | CH$_3$ | CH | S | O | |
| H | H | OCH$_3$ | H | OCH$_3$ | OCH$_3$ | CH | S | O | |
| H | H | OC$_2$H$_5$ | H | CH$_3$ | OCH$_3$ | CH | S | O | |
| H | H | SCH$_3$ | H | CH$_3$ | CH$_3$ | CH | S | O | |

TABLE I-continued

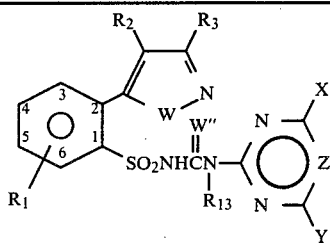

| $R_1$ | $R_2$ | $R_3$ | $R_{13}$ | X | Y | Z | W | W″ | m.p. (°C.) |
|---|---|---|---|---|---|---|---|---|---|
| H | H | H | H | Cl | $NH_2$ | CH | O | O | |
| H | H | H | H | Cl | $OCH_3$ | CH | O | O | |
| H | H | H | H | Cl | $NHCH_3$ | CH | O | O | |
| H | H | H | H | Cl | $N(CH_3)_2$ | CH | O | O | |
| H | H | H | H | $CH_3$ | $CH_2OCH_3$ | CH | O | O | |
| H | H | H | H | $CH_3$ | $C_2H_5$ | CH | O | O | |
| H | H | H | H | $CH_3$ | $OC_2H_5$ | CH | O | O | |
| H | H | H | H | $OCH_3$ | $CH(OCH_3)_2$ | CH | O | O | |
| H | $CH_3$ | $CH_3$ | H | $OCH_3$ | $OCH_3$ | CH | O | O | |
| H | $CH_3$ | $CH_3$ | H | $OCH_3$ | $CH_3$ | N | O | O | |
| H | $CH_3$ | $CH_3$ | H | $OCH_3$ | $CH_3$ | CH | O | O | |
| H | H | $CH_3$ | H | $OCH_3$ | $OCH_3$ | N | O | O | |
| H | H | $CH_3$ | H | $CH_3$ | $CH_3$ | N | O | O | |
| H | $CH_3$ | H | H | $OCH_3$ | $OCH_3$ | N | O | O | |
| H | $CH_3$ | H | H | $CH_3$ | $CH_3$ | N | O | O | |
| H | $CH_3$ | $CH_3$ | H | $CH_3$ | $CH_3$ | CH | O | O | |
| H | $CH_3$ | $CH_3$ | H | $OCH_3$ | $OCH_3$ | N | O | O | |
| H | $CH_3$ | $CH_3$ | H | $CH_3$ | $CH_3$ | N | O | O | |
| H | H | $C_2H_5$ | H | $OCH_3$ | $OCH_3$ | N | O | O | |
| H | H | $C_2H_5$ | H | $CH_3$ | $CH_3$ | N | O | O | |
| H | $C_2H_5$ | H | H | $OCH_3$ | $OCH_3$ | N | O | O | |
| H | $C_2H_5$ | H | H | $CH_3$ | $CH_3$ | N | O | O | |
| H | H | H | $CH_3$ | $CH_3$ | $OCH_3$ | CH | O | O | |
| H | H | H | $CH_3$ | $CH_3$ | $CH_3$ | CH | O | O | |
| H | H | H | $CH_3$ | $OCH_3$ | $OCH_3$ | N | O | O | |
| H | H | H | $CH_3$ | $CH_3$ | $CH_3$ | N | O | O | |
| H | H | H | H | $OCH_3$ | $OCH_3$ | CH | O | O | 183–187° |
| H | H | H | H | $OCH_3$ | $OCH_3$ | CH | O | S | |
| H | H | H | H | $OCH_3$ | $CH_3$ | N | O | S | |
| H | H | H | H | $CH_3$ | $OC_2H_5$ | CH | O | S | |
| H | H | H | H | $CH_3$ | $OCH_2CH_2OCH_3$ | N | O | O | |
| H | H | H | H | $CH_3$ | $OCH_2CF_3$ | N | O | O | |
| H | H | H | H | $OCH_3$ | $SCH_3$ | N | O | O | |
| H | H | H | H | $CH_3$ | $CF_3$ | CH | O | O | |
| H | H | H | H | $CH_3$ | ![dioxolane](O-CH-O with CH₂CH₂) | CH | O | O | |
| H | H | H | H | Cl | $OC_2H_5$ | CH | O | O | |

TABLE Ia

| R | $R_1$ | $R_2$ | $R_3$ | $R_5$ | $R_{13}$ | X | Y | Z | W″ | m.p. (°C.) |
|---|---|---|---|---|---|---|---|---|---|---|
| $CH_3$ | H | H | H | H | H | $CH_3$ | $CH_3$ | CH | O | 212–216° |
| $CH_3$ | H | H | H | H | H | $CH_3$ | $OCH_3$ | CH | O | 207–211° |
| $CH_3$ | H | H | H | H | H | $OCH_3$ | $OCH_3$ | N | O | 190–195° |
| $CH_3$ | H | H | H | H | H | $CH_3$ | $CH_3$ | N | O | 192–197° |
| $CH_3$ | H | H | H | H | H | $CH_3$ | $OCH_3$ | N | O | 202–205° |
| H | H | H | H | H | H | $OCH_3$ | $OCH_3$ | CH | O | |
| $C_2H_5$ | H | H | H | H | H | $CH_3$ | $OCH_3$ | CH | O | |

TABLE Ia-continued

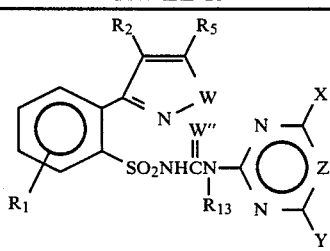

| R | R1 | R2 | R3 | R5 | R13 | X | Y | Z | W" | m.p. (°C.) |
|---|---|---|---|---|---|---|---|---|---|---|
| n-propyl | H | H | H | H | H | OCH3 | OCH3 | CH | O | |
| CH(CH3)2 | H | H | H | H | H | OCH3 | OCH3 | CH | O | |
| CH3 | H | H | H | H | CH3 | OCH3 | OCH3 | CH | O | |
| CH3 | H | CH3 | H | H | H | OCH3 | OCH3 | CH | O | |
| CH3 | H | CH3 | H | H | H | OCH3 | CH3 | CH | O | |
| CH3 | H | CH3 | H | H | H | OCH3 | CH3 | N | O | |
| CH3 | H | H | CH3 | CH3 | H | OCH3 | OCH3 | CH | O | |
| CH3 | H | H | CH3 | CH3 | H | CH3 | OCH3 | CH | O | |
| CH3 | H | H | CH3 | CH3 | H | OCH3 | CH3 | N | O | |
| CH3 | H | CH3 | CH3 | CH3 | H | OCH3 | OCH3 | CH | O | |
| CH3 | H | CH3 | CH3 | CH3 | H | OCH3 | CH3 | N | O | |
| CH3 | H | C2H5 | H | H | H | OCH3 | OCH3 | CH | O | |
| CH3 | H | H | CH3 | CH3 | H | CH3 | CH3 | CH | O | |
| CH3 | H | H | CH3 | CH3 | H | OCH3 | OCH3 | N | O | |
| CH3 | H | H | CH3 | CH3 | H | CH3 | CH3 | N | O | |
| CH3 | H | CH3 | H | H | H | CH3 | CH3 | CH | O | |
| CH3 | H | CH3 | H | H | H | OCH3 | OCH3 | N | O | |
| CH3 | H | CH3 | H | H | H | CH3 | CH3 | N | O | |
| CH3 | H | H | C2H5 | C2H5 | H | OCH3 | OCH3 | CH | O | |
| CH3 | H | H | C2H5 | C2H5 | H | OCH3 | CH3 | CH | O | |
| CH3 | H | H | C2H5 | C2H5 | H | OCH3 | CH3 | N | O | |
| CH3 | H | H | C2H5 | C2H5 | H | CH3 | CH3 | CH | O | |
| CH3 | H | H | C2H5 | C2H5 | H | OCH3 | OCH3 | N | O | |
| CH3 | H | H | H | H | H | OCH3 | OCH3 | CH | O | 210–212° |
| CH3 | H | H | H | H | H | Cl | OCH3 | CH | O | |
| CH2(CH2)2CH3 | H | H | H | H | H | OCH3 | OCH3 | CH | O | |
| CH3 | H | H | H | H | H | OCH3 | CH(OCH3)2 | CH | O | |
| CH3 | H | H | H | H | H | OCH3 | CH2OCH3 | CH | O | |
| CH3 | H | H | H | H | H | CH3 | OC2H5 | CH | O | |
| CH3 | H | H | H | H | H | OCH3 | O–CH(–O–) (dioxolane) | CH | O | |
| CH3 | H | H | H | H | H | OCH3 | OCH3 | CH | S | |

TABLE Ib

| R1 | R2 | R5 | R13 | X | Y | Z | W | W" | m.p. (°C.) |
|---|---|---|---|---|---|---|---|---|---|
| H | H | H | H | CH3 | OCH3 | CH | O | O | |
| H | H | H | H | CH3 | CH3 | CH | O | O | |
| H | H | H | H | OCH3 | OCH3 | CH | O | O | 189–193° |
| H | H | H | H | CH3 | CH3 | N | O | O | |
| H | H | H | H | OCH3 | OCH3 | N | O | O | |
| H | H | H | H | CH3 | OCH3 | N | O | O | |
| H | H | H | H | CH3 | CH3 | CH | S | O | |
| H | H | H | H | OCH3 | OCH3 | CH | S | O | |
| H | H | H | H | OCH3 | CH3 | CH | S | O | |
| H | H | H | H | CH3 | CH3 | N | S | O | |
| H | H | H | H | OCH3 | OCH3 | N | S | O | |
| H | H | H | H | OCH3 | CH3 | N | S | O | |
| H | H | H | CH3 | OCH3 | OCH3 | CH | O | O | |

TABLE Ib-continued

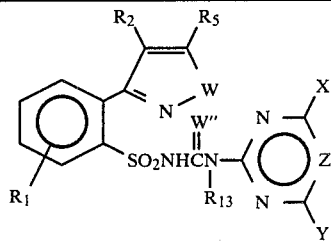

| R₁ | R₂ | R₅ | R₁₃ | X | Y | Z | W | W''' | m.p. (°C.) |
|---|---|---|---|---|---|---|---|---|---|
| H | H | CH₃ | H | OCH₃ | OCH₃ | CH | O | O | |
| H | H | CH₃ | H | OCH₃ | CH₃ | CH | O | O | |
| H | H | CH₃ | H | CH₃ | CH₃ | CH | O | O | |
| H | H | CH₃ | H | OCH₃ | CH₃ | N | O | O | |
| H | H | C₂H₅ | H | OCH₃ | OCH₃ | CH | O | O | |
| H | H | C₂H₅ | H | OCH₃ | CH₃ | CH | O | O | |
| H | H | C₂H₅ | H | CH₃ | CH₃ | CH | O | O | |
| H | H | C₂H₅ | H | OCH₃ | CH₃ | N | O | O | |
| H | H | OCH₃ | H | OCH₃ | OCH₃ | CH | O | O | |
| H | H | OCH₃ | H | CH₃ | OCH₃ | CH | O | O | |
| H | H | OCH₃ | H | CH₃ | CH₃ | CH | O | O | |
| H | H | OCH₃ | H | OCH₃ | CH₃ | N | O | O | |
| H | CH₃ | CH₃ | H | OCH₃ | OCH₃ | CH | O | O | |
| H | CH₃ | CH₃ | H | OCH₃ | CH₃ | CH | O | O | |
| H | H | Cl | H | OCH₃ | OCH₃ | CH | S | O | |
| H | H | Br | H | OCH₃ | CH₃ | CH | S | O | |
| H | H | OCH₃ | H | OCH₃ | OCH₃ | CH | S | O | |
| H | H | O₂H₅ | H | OCH₃ | CH₃ | CH | S | O | |
| H | H | SCH₃ | H | CH₃ | CH₃ | CH | S | O | |
| H | H | CH₃ | H | OCH₃ | OCH₃ | N | O | O | |
| H | H | CH₃ | H | CH₃ | CH₃ | N | O | O | |
| H | H | OCH₃ | H | OCH₃ | OCH₃ | N | O | O | |
| H | H | OCH₃ | H | CH₃ | CH₃ | N | O | O | |
| H | H | C₂H₅ | H | OCH₃ | OCH₃ | N | O | O | |
| H | H | H | H | Cl | OCH₃ | CH | O | O | |
| H | H | H | H | OCH₃ | CH(OCH₃)₂ | CH | O | O | |
| H | H | H | H | OCH₃ | OCH₃ | CH | O | S | |

TABLE Ic

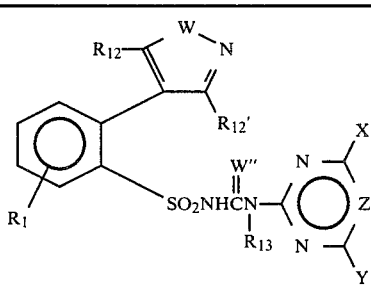

| R₁ | R₁₂ | R₁₂' | R₁₃ | X | Y | Z | W | W''' | m.p. (°C.) |
|---|---|---|---|---|---|---|---|---|---|
| H | H | H | H | CH₃ | CH₃ | CH | O | O | 197–202° |
| H | H | H | H | OCH₃ | CH₃ | CH | O | O | 181–185° |
| H | H | H | H | CH₃ | CH₃ | N | O | O | 187–192° |
| H | H | H | H | OCH₃ | OCH₃ | N | O | O | 180–185° |
| H | H | H | H | CH₃ | OCH₃ | N | O | O | 178–181° |
| H | CH₃ | H | H | OCH₃ | OCH₃ | CH | O | O | |
| H | CH₃ | H | H | OCH₃ | CH₃ | CH | O | O | |
| H | CH₃ | H | H | OCH₃ | CH₃ | N | O | O | |
| H | CH₃ | H | H | CH₃ | CH₃ | CH | O | O | |
| H | CH₃ | CH₃ | H | CH₃ | CH₃ | CH | O | O | |
| H | CH₃ | CH₃ | H | OCH₃ | OCH₃ | CH | O | O | |
| H | CH₃ | CH₃ | H | OCH₃ | CH₃ | CH | O | O | |
| H | CH₃ | CH₃ | H | OCH₃ | CH₃ | N | O | O | |
| H | H | H | CH₃ | OCH₃ | OCH₃ | CH | O | O | |
| H | H | H | CH₃ | CH₃ | OCH₃ | CH | O | O | |
| H | H | H | H | CH₃ | CH₂OCH₃ | CH | O | O | |
| H | H | H | H | CH₃ | OC₂H₅ | CH | O | O | |
| H | H | H | H | OCH₃ | CH(OCH₃)₂ | CH | O | O | |
| H | H | H | H | CH₃ | C₂H₅ | CH | O | O | |
| H | H | H | H | Cl | OCH₃ | CH | O | O | |
| H | H | H | H | Cl | NH₂ | CH | O | O | |
| H | H | H | H | Cl | NHCH₃ | CH | O | O | |

TABLE Ic-continued

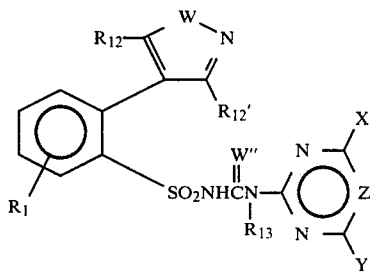

| R₁ | R₁₂ | R₁₂' | R₁₃ | X | Y | Z | W | W" | m.p. (°C.) |
|---|---|---|---|---|---|---|---|---|---|
| H | H | H | H | Cl | N(CH₃)₂ | CH | O | O | |
| H | H | H | H | CH₃ | CH₃ | CH | NCH₃ | O | 218–222° |
| H | H | H | H | OCH₃ | CH₃ | CH | NCH₃ | O | 222–226° |
| H | H | H | H | OCH₃ | OCH₃ | CH | NCH₃ | O | 220–226° |
| H | H | H | H | CH₃ | CH₃ | N | NCH₃ | O | 232–237° |
| H | H | H | H | OCH₃ | OCH₃ | N | NCH₃ | O | 195–200° |
| H | CH₃ | H | H | OCH₃ | OCH₃ | CH | NCH₃ | O | |
| H | CH₃ | H | H | OCH₃ | CH₃ | CH | NCH₃ | O | |
| H | CH₃ | H | H | CH₃ | CH₃ | CH | NCH₃ | O | |
| H | CH₃ | H | H | OCH₃ | CH₃ | N | NCH₃ | O | |
| H | CH₃ | CH₃ | H | CH₃ | CH₃ | CH | NCH₃ | O | |
| H | CH₃ | CH₃ | H | OCH₃ | CH₃ | CH | NCH₃ | O | |
| H | CH₃ | CH₃ | H | OCH₃ | OCH₃ | CH | NCH₃ | O | |
| H | CH₃ | CH₃ | H | CH₃ | OCH₃ | N | NCH₃ | O | |
| H | CH₃ | CH₃ | H | OCH₃ | OCH₃ | N | NCH₃ | O | |
| H | H | H | H | CH₃ | CH₃OCH₃ | CH | NCH₃ | O | |
| H | H | H | H | CH₃ | OC₂H₅ | CH | NCH₃ | O | |
| H | H | H | H | CH₃ | CH(OCH₃)₂ | CH | NCH₃ | O | |
| H | H | H | CH₃ | OCH₃ | OCH₃ | CH | NCH₃ | O | |
| H | H | H | CH₃ | CH₃ | OCH₃ | CH | NCH₃ | O | |
| H | H | H | H | CH₃ | CH₃ | CH | S | O | |
| H | H | H | H | OCH₃ | CH₃ | CH | S | O | |
| H | H | H | H | OCH₃ | OCH₃ | CH | S | O | |
| H | H | H | H | CH₃ | CH₃ | N | S | O | |
| H | H | H | H | CH₃ | OCH₃ | N | S | O | |
| H | H | H | H | OCH₃ | OCH₃ | N | S | O | |
| H | CH₃ | H | H | OCH₃ | OCH₃ | N | O | O | |
| H | CH₃ | H | H | CH₃ | CH₃ | N | O | O | |
| H | CH₃ | CH₃ | H | OCH₃ | OCH₃ | N | O | O | |
| H | CH₃ | CH₃ | H | CH₃ | CH₃ | N | O | O | |
| H | H | H | H | OCH₃ | OCH₃ | CH | O | O | 175–178° |
| H | H | H | H | OCH₃ | CH₃ | N | NCH₃ | O | 221–224° |

TABLE Id

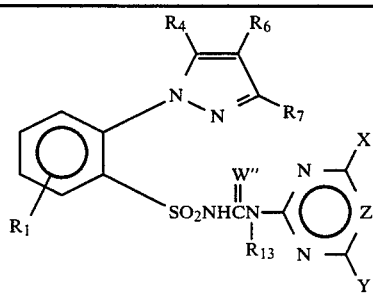

| R₁ | R₄ | R₆ | R₇ | R₁₃ | X | Y | Z | W" | m.p. (°C.) |
|---|---|---|---|---|---|---|---|---|---|
| H | H | H | H | H | CH₃ | CH₃ | CH | O | 198–202° |
| H | H | H | H | H | OCH₃ | OCH₃ | CH | O | 194–198° |
| H | H | H | H | H | OCH₃ | CH₃ | CH | O | 200–204° |
| H | H | H | H | H | OCH₃ | OCH₃ | N | O | 188–192° |
| H | H | H | H | H | OCH₃ | CH₃ | N | O | 184–188° |
| H | CH₃ | H | CH₃ | H | CH₃ | CH₃ | CH | O | |
| H | CH₃ | H | CH₃ | H | OCH₃ | OCH₃ | CH | O | |
| H | CH₃ | H | CH₃ | H | OCH₃ | CH₃ | CH | O | |
| H | CH₃ | H | CH₃ | H | OCH₃ | OCH₃ | N | O | |
| H | CH₃ | H | CH₃ | H | OCH₃ | CH₃ | N | O | |
| H | CH₃ | H | CH₃ | H | CH₃ | CH₃ | N | O | |
| H | H | H | H | CH₃ | OCH₃ | OCH₃ | CH | O | |
| H | CH₃ | C₂H₅ | CH₃ | H | OCH₃ | OCH₃ | CH | O | |
| H | H | C₂H₅ | H | H | OCH₃ | OCH₃ | CH | O | |
| H | CH₃ | CH₃ | CH₃ | H | OCH₃ | OCH₃ | CH | O | |

TABLE Id-continued

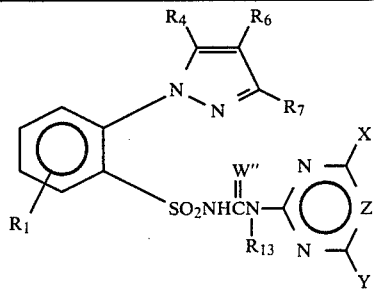

| R$_1$ | R$_4$ | R$_6$ | R$_7$ | R$_{13}$ | X | Y | Z | W" | m.p. (°C.) |
|---|---|---|---|---|---|---|---|---|---|
| H | CH$_3$ | CH$_3$ | CH$_3$ | H | OCH$_3$ | CH$_3$ | CH | O | |
| H | CH$_3$ | CH$_3$ | CH$_3$ | H | OCH$_3$ | CH$_3$ | N | O | |
| H | CH$_2$CH$_2$CH$_3$ | H | H | H | OCH$_3$ | OCH$_3$ | CH | O | |
| H | H | H | CH(CH$_3$)$_2$ | H | OCH$_3$ | CH$_3$ | N | O | |
| H | H | H | H | H | CH$_3$ | CH$_3$ | N | O | 201–205° |
| H | C$_2$H$_5$ | H | C$_2$H$_5$ | H | OCH$_3$ | OCH$_3$ | CH | O | |
| H | CH$_2$(CH$_2$)$_2$CH$_3$ | H | H | H | OCH$_3$ | OCH$_3$ | CH | O | |
| H | H | H | CH$_2$(CH$_2$)$_2$CH$_3$ | H | OCH$_3$ | OCH$_3$ | CH | O | |
| H | H | H | H | H | Cl | OCH$_3$ | CH | O | |
| H | H | H | H | H | OCH$_3$ | C$_2$H$_5$ | CH | O | |
| H | H | H | H | H | CH$_3$ | OC$_2$H$_5$ | CH | H | |
| H | H | H | H | H | OCH$_3$ | CH$_2$OCH$_3$ | CH | O | |
| H | H | H | H | H | OCH$_3$ | CH(OCH$_3$)$_2$ | CH | O | |
| H | H | H | H | H | CH$_3$ | OC$_2$H$_5$ | N | O | |
| H | H | H | H | H | OCH$_3$ | OCH$_3$ | CH | S | |
| H | H | H | H | H | OCH$_3$ | SCH$_3$ | CH | O | |
| H | H | H | H | H | CH$_3$ | CF$_3$ | CH | O | |

TABLE II

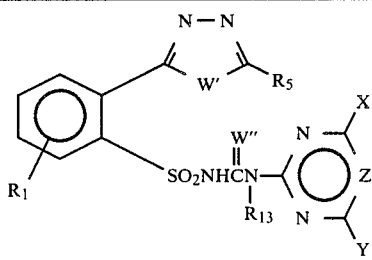

| R$_1$ | R$_5$ | R$_{13}$ | X | Y | Z | W' | W" | m.p. (°C.) |
|---|---|---|---|---|---|---|---|---|
| H | H | H | CH$_3$ | CH$_3$ | CH | O | O | |
| H | H | H | OCH$_3$ | OCH$_3$ | CH | O | O | |
| H | H | H | OCH$_3$ | CH$_3$ | CH | O | O | |
| H | H | H | CH$_3$ | CH$_3$ | N | O | O | |
| H | H | H | OCH$_3$ | OCH$_3$ | N | O | O | |
| H | H | H | OCH$_3$ | CH$_3$ | N | O | O | |
| H | CH$_3$ | H | CH$_3$ | CH$_3$ | CH | O | O | 209–212° |
| H | CH$_3$ | H | OCH$_3$ | OCH$_3$ | CH | O | O | 214–218° |
| H | CH$_3$ | H | CH$_3$ | OCH$_3$ | CH | O | O | 196–200° |
| H | CH$_3$ | H | CH$_3$ | CH$_3$ | N | O | O | 182–192° |
| H | CH$_3$ | H | OCH$_3$ | OCH$_3$ | N | O | O | |
| H | CH$_3$ | H | OCH$_3$ | CH$_3$ | N | O | O | 186–190° |
| H | C$_2$H$_5$ | H | CH$_3$ | CH$_3$ | CH | O | O | |
| H | C$_2$H$_5$ | H | OCH$_3$ | CH | O | O | | |
| H | C$_2$H$_5$ | H | CH$_3$ | OCH$_3$ | CH | O | O | |
| H | C$_2$H$_5$ | H | CH$_3$ | CH$_3$ | N | O | O | |
| H | C$_2$H$_5$ | H | OCH$_3$ | OCH$_3$ | N | O | O | |
| H | C$_2$H$_5$ | H | CH$_3$ | OCH$_3$ | N | O | O | |
| H | CH$_3$ | H | Cl | NH$_2$ | CH | O | O | |
| H | H | H | CH$_3$ | CH$_3$ | CH | S | O | |
| H | H | H | OCH$_3$ | OCH$_3$ | CH | S | O | |
| H | H | H | OCH$_3$ | CH$_3$ | CH | S | O | |
| H | H | H | CH$_3$ | CH$_3$ | N | S | O | |
| H | H | H | OCH$_3$ | OCH$_3$ | N | S | O | |
| H | H | H | OCH$_3$ | CH$_3$ | N | S | O | |
| H | CH$_3$ | H | CH$_3$ | CH$_3$ | CH | S | O | |
| H | CH$_3$ | H | OCH$_3$ | OCH$_3$ | CH | S | O | 227–230° |
| H | CH$_3$ | H | OCH$_3$ | CH$_3$ | CH | S | O | |
| H | CH$_3$ | H | CH$_3$ | CH$_3$ | N | S | O | |
| H | CH$_3$ | H | OCH$_3$ | OCH$_3$ | N | S | O | |
| H | CH$_3$ | H | CH$_3$ | OCH$_3$ | N | S | O | |

TABLE II-continued

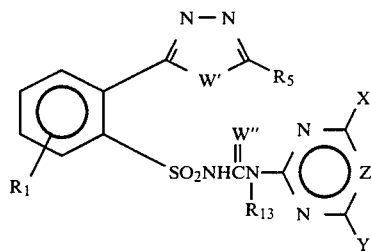

| R₁ | R₅ | R₁₃ | X | Y | Z | W' | W''' | m.p. (°C.) |
|---|---|---|---|---|---|---|---|---|
| H | C₂H₅ | H | OCH₃ | OCH₃ | CH | S | O | |
| H | C₂H₅ | H | OCH₃ | CH₃ | CH | S | O | |
| H | C₂H₅ | H | CH₃ | OCH₃ | N | S | O | |
| H | H | CH₃ | OCH₃ | OCH₃ | CH | O | O | |
| 5-F | CH₃ | H | OCH₃ | OCH₃ | CH | O | O | |
| 6-Cl | CH₃ | H | OCH₃ | OCH₃ | CH | O | O | |
| 4-Br | CH₃ | H | OCH₃ | CHh₃ | CH | O | O | |
| 3-CH₃ | CH₃ | H | OCH₃ | OCH₃ | CH | O | O | |
| 5-CF₃ | CH₃ | H | OCH₃ | OCH₃ | CH | O | O | |
| 5-OCH₃ | CH₃ | H | OCH₃ | OCH₃ | CH | O | O | |
| H | CH₃ | H | Cl | OCH₃ | CH | O | O | |
| H | CH₃ | H | Cl | NHCH₃ | CH | O | O | |
| H | CH₃ | H | Cl | N(CH₃)₂ | CH | O | O | |
| H | CH₃ | H | CH₃ | CH₂OCH₃ | CH | O | O | |
| H | CH₃ | H | CH₃ | C₂H₅ | CH | O | O | |
| H | CH₃ | H | CH₃ | OC₂H₅ | CH | O | O | |
| H | CH₃ | H | OCH₃ | CH(OCH₃)₂ | CH | O | O | |
| H | C₂H₅ | H | CH₃ | CH₃ | CH | S | O | |
| H | C₂H₅ | H | OCH₃ | OCH₃ | N | S | O | |
| H | C₂H₅ | H | CH₃ | CH₃ | N | S | O | |
| H | CH₃ | H | OCH₃ | OCH₃ | CH | O | S | |
| H | CH₃ | H | OCH₃ | CH₃ | N | O | S | |
| H | CH₃ | H | OCH₃ | ⟨OCH-O⟩ (dioxolane) | CH | O | O | |

TABLE IIa

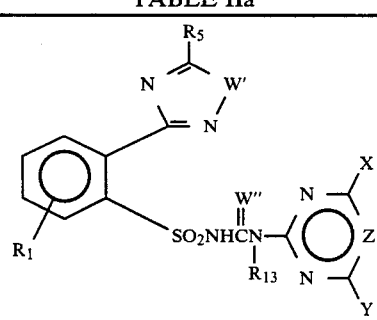

| R₁ | R₅ | R₁₃ | X | Y | Z | W' | W''' | m.p. (°C.) |
|---|---|---|---|---|---|---|---|---|
| H | H | H | CH₃ | CH₃ | CH | O | O | |
| H | H | H | OCH₃ | OCH₃ | CH | O | O | |
| H | H | H | CH₃ | OCH₃ | CH | O | O | |
| H | H | H | CH₃ | CH₃ | N | O | O | |
| H | H | H | OCH₃ | OCH₃ | N | O | O | |
| H | H | H | CH₃ | OCH₃ | N | O | O | |
| H | CH₃ | H | CH₃ | CH₃ | CH | O | O | |
| H | CH₃ | H | OCH₃ | OCH₃ | CH | O | O | |
| H | CH₃ | H | CH₃ | OCH₃ | CH | O | O | |
| H | CH₃ | H | CH₃ | CH₃ | N | O | O | |
| H | CH₃ | H | OCH₃ | OCH₃ | N | O | O | |
| H | CH₃ | H | CH₃ | OCH₃ | N | O | O | |
| H | C₂H₅ | H | CH₃ | CH₃ | CH | O | O | |
| H | C₂H₅ | H | OCH₃ | OCH₃ | CH | O | O | |
| H | C₂H₅ | H | CH₃ | OCH₃ | CH | O | O | |
| H | C₂H₅ | H | CH₃ | CH₃ | N | O | O | |
| H | C₂H₅ | H | OCH₃ | OCH₃ | N | O | O | |
| H | SCH₃ | H | OCH₃ | OCH₃ | CH | S | O | |

TABLE IIa-continued

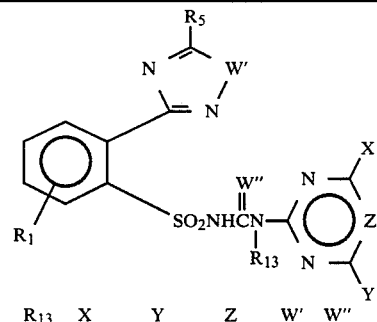

| R₁ | R₅ | R₁₃ | X | Y | Z | W' | W''' | m.p. (°C.) |
|---|---|---|---|---|---|---|---|---|
| H | OCH₃ | H | OCH₃ | OCH₃ | CH | S | O | |
| H | OC₂H₅ | H | OCH₃ | OCH₃ | CH | S | O | |
| H | Cl | H | OCH₃ | OCH₃ | CH | S | O | |
| H | Br | H | OCH₃ | CH₃ | CH | S | O | |
| H | H | CH₃ | OCH₃ | CH₃ | CH | O | O | |
| H | C₂H₅ | H | CH₃ | CH₃ | N | O | O | |
| H | H | H | OCH₃ | OCH₃ | CH | S | O | |
| H | H | H | OCH₃ | OCH₃ | CH | S | O | |
| H | H | H | CH₃ | OCH₃ | CH | S | O | |
| H | H | H | CH₃ | CH₃ | N | S | O | |
| H | H | H | OCH₃ | OCH₃ | N | S | O | |
| H | H | H | CH₃ | OCH₃ | N | S | O | |
| H | Cl | H | CH₃ | CH₃ | CH | S | O | |
| H | Cl | H | CH₃ | OCH₃ | CH | S | O | |
| H | Cl | H | CH₃ | CH₃ | N | S | O | |
| H | Cl | H | OCH₃ | OCH₃ | N | S | O | |
| H | Cl | H | CH₃ | OCH₃ | N | S | O | |

TABLE IIb

| $R_1$ | $R_5$ | $R_{13}$ | X | Y | Z | W' | W'' | m.p. (°C.) |
|---|---|---|---|---|---|---|---|---|
| H | H | H | CH$_3$ | CH$_3$ | CH | O | O | |
| H | H | H | OCH$_3$ | OCH$_3$ | CH | O | O | |
| H | H | H | CH$_3$ | OCH$_3$ | CH | O | O | |
| H | H | H | CH$_3$ | CH$_3$ | N | O | O | |
| H | H | H | OCH$_3$ | OCH$_3$ | N | O | O | |
| H | H | H | OCH$_3$ | CH$_3$ | N | O | O | |
| H | CH$_3$ | H | CH$_3$ | CH$_3$ | CH | O | O | 202–206° |
| H | CH$_3$ | H | OCH$_3$ | OCH$_3$ | CH | O | O | 230–234° |
| H | CH$_3$ | H | CH$_3$ | OCH$_3$ | CH | O | O | 189–193° |
| H | CH$_3$ | H | CH$_3$ | CH$_3$ | N | O | O | 211–214° |
| H | CH$_3$ | H | OCH$_3$ | OCH$_3$ | N | O | O | 194–198° |
| H | CH$_3$ | H | CH$_3$ | OCH$_3$ | N | O | O | 188–192° |
| H | H | H | CH$_3$ | CH$_3$ | CH | S | O | |
| H | H | H | OCH$_3$ | OCH$_3$ | CH | S | O | |
| H | H | H | CH$_3$ | OCH$_3$ | CH | S | O | |
| H | H | H | CH$_3$ | CH$_3$ | N | S | O | |
| H | H | H | OCH$_3$ | OCH$_3$ | N | S | O | |
| H | H | H | OCH$_3$ | CH$_3$ | N | S | O | |
| H | H | CH$_3$ | OCH$_3$ | OCH$_3$ | CH | O | O | |
| H | C$_2$H$_5$ | H | OCH$_3$ | OCH$_3$ | CH | O | O | |
| H | C$_2$H$_5$ | H | OCH$_3$ | CH$_3$ | CH | O | O | |
| H | C$_2$H$_5$ | H | OCH$_3$ | CH$_3$ | N | O | O | |
| H | CH$_3$ | H | OCH$_3$ | OCH$_3$ | CH | S | O | |
| H | CH$_3$ | H | OCH$_3$ | CH$_3$ | CH | S | O | |
| H | CH$_3$ | H | OCH$_3$ | CH$_3$ | N | S | O | |
| H | CH$_3$ | H | OCH$_3$ | OCH$_3$ | CH | O | S | |
| H | CH$_3$ | H | CH$_3$ | OCH$_2$CH$_2$OCH$_3$ | N | O | O | |
| H | CH$_3$ | H | CH$_3$ | OCH$_2$CF$_3$ | N | O | O | |
| H | CH$_3$ | H | OCH$_3$ | SCH$_3$ | N | O | O | |
| H | CH$_3$ | H | CH$_3$ | CF$_3$ | CH | O | O | |
| H | CH$_3$ | H | OCH$_3$ | 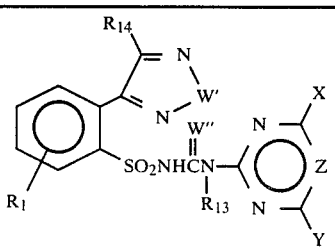 | CH | O | O | |
| H | CH$_3$ | H | OCH$_3$ | CH$_2$OCH$_3$ | CH | O | O | |
| H | CH$_3$ | H | CH$_3$ | OC$_2$H$_5$ | N | O | O | |
| H | CH$_3$ | H | OCH$_3$ | CH(OCH$_3$)$_2$ | CH | O | O | |

TABLE IIc

| $R_1$ | $R_{13}$ | $R_{14}$ | X | Y | Z | W' | W'' | m.p. (°C.) |
|---|---|---|---|---|---|---|---|---|
| H | H | H | CH$_3$ | CH$_3$ | CH | O | O | |
| H | H | H | OCH$_3$ | OCH$_3$ | CH | O | O | |
| H | H | H | CH$_3$ | OCH$_3$ | CH | O | O | |
| H | H | H | CH$_3$ | CH$_3$ | N | O | O | |
| H | H | H | OCH$_3$ | OCH$_3$ | N | O | O | |
| H | H | H | OCH$_3$ | CH$_3$ | N | O | O | |
| H | H | Cl | OCH$_3$ | OCH$_3$ | CH | O | O | |
| H | H | Cl | CH$_3$ | OCH$_3$ | CH | O | O | |
| H | H | OCH$_3$ | CH$_3$ | CH$_3$ | CH | S | O | |
| H | H | Cl | OCH$_3$ | OCH$_3$ | N | O | O | |

TABLE IIc-continued

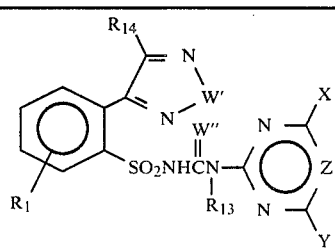

| $R_1$ | $R_{13}$ | $R_{14}$ | X | Y | Z | W' | W'' | m.p. (°C.) |
|---|---|---|---|---|---|---|---|---|
| H | H | Cl | CH$_3$ | OCH$_3$ | N | O | O | |
| H | H | OCH$_3$ | OCH$_3$ | OCH$_3$ | CH | O | O | |
| H | H | OC$_2$H$_5$ | OCH$_3$ | OCH$_3$ | CH | O | O | |
| H | H | SCH$_3$ | OCH$_3$ | OCH$_3$ | CH | O | O | |
| H | CH$_3$ | H | OCH$_3$ | OCH$_3$ | CH | O | O | |
| H | H | H | CH$_3$ | CH$_3$ | CH | S | O | |
| H | H | H | OCH$_3$ | OCH$_3$ | CH | S | O | |
| H | H | H | CH$_3$ | CH$_3$ | N | S | O | |
| H | H | H | CH$_3$ | OCH$_3$ | N | S | O | |

TABLE IIc-continued

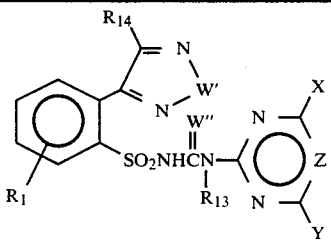

| R₁ | R₁₃ | R₁₄ | X | Y | Z | W' | W" | m.p. (°C.) |
|---|---|---|---|---|---|---|---|---|
| H | H | H | OCH₃ | OCH₃ | N | S | O | |
| H | H | Cl | OCH₃ | OCH₃ | CH | S | O | |
| H | H | Cl | OCH₃ | CH₃ | CH | S | O | |
| H | H | Cl | OCH₃ | CH₃ | N | S | O | |
| H | H | OC₂H₅ | OCH₃ | OCH₃ | CH | S | O | |
| H | H | SCH₃ | OCH₃ | OCH₃ | CH | S | O | |
| H | H | CH₃ | OCH₃ | OCH₃ | CH | O | O | |
| H | H | C₂H₅ | OCH₃ | OCH₃ | CH | O | O | |

TABLE IId

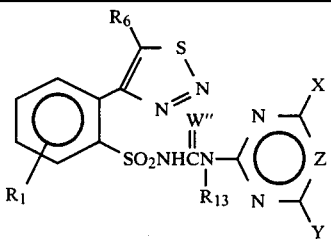

| R₁ | R₆ | R₁₃ | X | Y | Z | W" | m.p. (°C.) |
|---|---|---|---|---|---|---|---|
| H | H | H | CH₃ | CH₃ | CH | O | 189–192° |
| H | H | H | CH₃ | OCH₃ | CH | O | 190–193° |
| H | H | H | OCH₃ | OCH₃ | CH | O | 199–203° |
| H | H | H | CH₃ | CH₃ | N | O | 190–194° |
| H | H | H | OCH₃ | CH₃ | N | O | 174–177° |
| H | H | H | OCH₃ | OCH₃ | N | O | 167–172° |
| H | CH₃ | H | OCH₃ | OCH₃ | CH | O | |
| H | CH₃ | H | CH₃ | OCH₃ | N | O | |
| H | C₂H₅ | H | OCH₃ | OCH₃ | CH | O | |
| H | C₂H₅ | H | CH₃ | OCH₃ | N | O | |
| H | H | CH₃ | OCH₃ | OCH₃ | CH | O | |
| H | H | H | OCH₃ | OCH₃ | CH | S | |
| H | H | H | Cl | OCH₃ | CH | O | |
| H | H | H | OCH₃ | CH₂OCH₃ | CH | O | |
| H | H | H | CH₃ | OC₂H₅ | N | O | |
| H | H | H | OCH₃ | CH(OCH₃)₂ | CH | O | |
| H | H | H | OCH₃ | 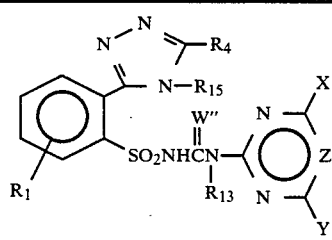 | CH | O | |
| H | H | H | OCH₃ | SCH₃ | N | O | |

TABLE IId-continued

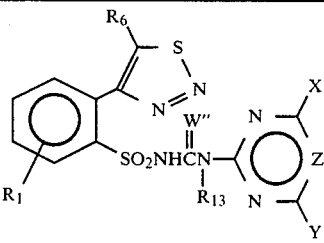

| R₁ | R₆ | R₁₃ | X | Y | Z | W" | m.p. (°C.) |
|---|---|---|---|---|---|---|---|
| H | H | H | CH₃ | CF₃ | CH | O | |
| H | H | H | OCH₃ | C₂H₅ | CH | O | |
| H | H | H | Cl | NH₂ | CH | O | |

TABLE IIe

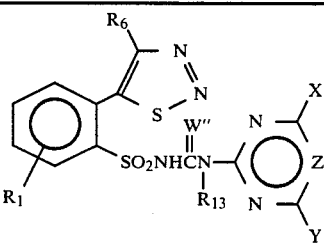

| R₁ | R₆ | R₁₃ | X | Y | Z | W" | m.p. (°C.) |
|---|---|---|---|---|---|---|---|
| H | H | H | CH₃ | CH₃ | CH | O | |
| H | H | H | CH₃ | OCH₃ | CH | O | |
| H | H | H | OCH₃ | OCH₃ | CH | O | |
| H | H | H | CH₃ | CH₃ | N | O | |
| H | H | H | OCH₃ | CH₃ | N | O | |
| H | H | H | OCH₃ | OCH₃ | N | O | |
| H | CH₃ | H | OCH₃ | OCH₃ | CH | O | |
| H | CH₃ | H | CH₃ | OCH₃ | N | O | |
| H | C₂H₅ | H | OCH₃ | OCH₃ | CH | O | |
| H | C₂H₅ | H | CH₃ | OCH₃ | N | O | |
| H | H | CH₃ | OCH₃ | OCH₃ | CH | O | |
| H | H | H | OCH₃ | OCH₃ | CH | S | |
| H | H | H | Cl | OCH₃ | CH | O | |
| H | H | H | OCH₃ | CH₂OCH₃ | CH | O | |
| H | H | H | CH₃ | OC₂H₅ | N | O | |
| H | H | H | OCH₃ | CH(OCH₃)₂ | CH | O | |
| H | H | H | OCH₃ | 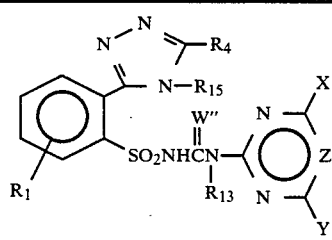 | CH | O | |
| H | H | H | OCH₃ | SCH₃ | N | O | |
| H | H | H | CH₃ | CF₃ | CH | O | |
| H | H | H | OCH₃ | C₂H₅ | CH | O | |
| H | H | H | Cl | NH₂ | CH | O | |

TABLE III

| R₁ | R₄ | R₁₃ | R₁₅ | X | Y | Z | W‴ | m.p. (°C.) |
|---|---|---|---|---|---|---|---|---|
| H | CH₃ | H | CH₃ | CH₃ | CH₃ | CH | O | |
| H | CH₃ | H | CH₃ | OCH₃ | OCH₃ | CH | O | |
| H | CH₃ | H | CH₃ | CH₃ | OCH₃ | CH | O | |

TABLE III-continued

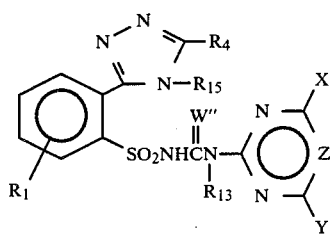

| R₁ | R₄ | R₁₃ | R₁₅ | X | Y | Z | W″ | m.p. (°C.) |
|---|---|---|---|---|---|---|---|---|
| H | CH₃ | H | CH₃ | CH₃ | CH₃ | N | O | |
| H | CH₃ | H | CH₃ | OCH₃ | OCH₃ | N | O | |
| H | CH₃ | H | CH₃ | CH₃ | OCH₃ | N | O | |
| H | H | H | CH₃ | OCH₃ | OCH₃ | CH | O | |
| H | C₂H₅ | H | CH₃ | OCH₃ | OCH₃ | CH | O | |
| H | C₂H₅ | H | CH₃ | OCH₃ | CH₃ | N | O | |
| H | CH₂CH₂CH₃ | H | CH₃ | OCH₃ | OCH₃ | CH | O | |
| H | CH₂(CH₂)₂CH₃ | H | CH₃ | OCH₃ | CH₃ | N | O | |
| H | CH₃ | H | C₂H₅ | OCH₃ | OCH₃ | CH | O | |
| H | CH₃ | H | CH₂CH₂CH₃ | OCH₃ | OCH₃ | CH | O | |
| H | CH₃ | H | CH(CH₃)₂ | OCH₃ | OCH₃ | CH | O | |
| H | CH₃ | CH₃ | CH₃ | OCH₃ | OCH₃ | CH | O | |

TABLE IIIa

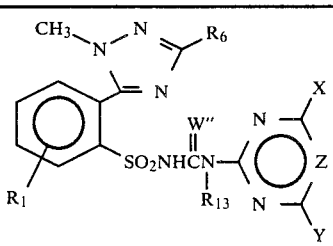

| R₁ | R₆ | R₁₃ | X | Y | Z | W″ | m.p. (°C.) |
|---|---|---|---|---|---|---|---|
| H | H | H | CH₃ | CH₃ | CH | O | |
| H | H | H | CH₃ | OCH₃ | CH | O | |
| H | H | H | OCH₃ | OCH₃ | CH | O | |
| H | H | H | CH₃ | CH₃ | N | O | |
| H | H | H | CH₃ | OCH₃ | N | O | |
| H | H | H | OCH₃ | OCH₃ | N | O | |
| H | CH₃ | H | CH₃ | CH₃ | CH | O | |
| H | CH₃ | H | OCH₃ | OCH₃ | CH | O | |
| H | CH₃ | H | CH₃ | OCH₃ | CH | O | |
| H | CH₃ | H | CH₃ | CH₃ | N | O | |
| H | CH₃ | H | CH₃ | OCH₃ | N | O | |
| H | CH₃ | H | OCH₃ | OCH₃ | N | O | |
| H | C₂H₅ | H | OCH₃ | OCH₃ | CH | O | |
| H | C₂H₅ | H | CH₃ | OCH₃ | CH | O | |
| H | C₂H₅ | H | OCH₃ | CH₃ | N | O | |
| 5-F | CH₃ | H | OCH₃ | OCH₃ | CH | O | |
| 6-Cl | CH₃ | H | CH₃ | CH₃ | CH | O | |
| 4-Br | CH₃ | H | OCH₃ | OCH₃ | CH | O | |
| 3-CH₃ | CH₃ | H | OCH₃ | OCH₃ | CH | O | |
| 5-CF₃ | CH₃ | H | OCH₃ | OCH₃ | CH | O | |
| 5-OCH₃ | CH₃ | H | OCH₃ | OCH₃ | CH | O | |
| H | CH₃ | CH₃ | OCH₃ | OCH₃ | CH | O | |

TABLE IIIb

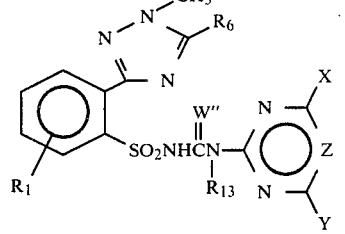

| R₁ | R₆ | R₁₃ | X | Y | Z | W″ | m.p. (°C.) |
|---|---|---|---|---|---|---|---|
| H | CH₃ | H | CH₃ | CH₃ | CH | O | |
| H | CH₃ | H | OCH₃ | OCH₃ | CH | O | |
| H | CH₃ | H | CH₃ | CH₃ | N | O | |
| H | CH₃ | H | OCH₃ | OCH₃ | N | O | |
| H | CH₃ | H | OCH₃ | CH₃ | N | O | |
| H | C₂H₅ | H | OCH₃ | OCH₃ | CH | O | |
| H | C₂H₅ | H | CH₃ | OCH₃ | CH | O | |
| H | C₂H₅ | H | CH₃ | CH₃ | N | O | |
| H | C₂H₅ | H | OCH₃ | OCH₃ | N | O | |
| H | C₂H₅ | H | CH₃ | OCH₃ | N | O | |
| H | H | H | OCH₃ | OCH₃ | CH | O | |
| H | H | H | CH₃ | OCH₃ | CH | O | |
| H | H | H | CH₃ | CH₃ | CH | O | |
| H | H | H | OCH₃ | CH₃ | N | O | |
| H | H | H | OCH₃ | CH₃ | N | O | |
| H | CH₃ | CH₃ | OCH₃ | OCH₃ | CH | O | |
| H | CH₃ | CH₃ | CH₃ | OCH₃ | N | O | |

TABLE IIIc

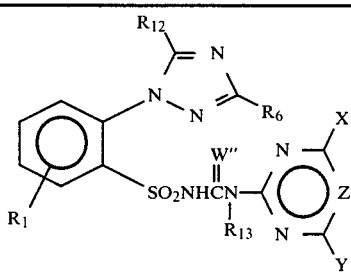

| R₁ | R₆ | R₁₂ | R₁₃ | X | Y | Z | W″ | m.p. (°C.) |
|---|---|---|---|---|---|---|---|---|
| H | H | H | H | CH₃ | CH₃ | CH | O | 198–202° |
| H | H | H | H | CH₃ | OCH₃ | CH | O | 214–217° |
| H | H | H | H | OCH₃ | OCH₃ | CH | O | 228–231° |
| H | H | H | H | CH₃ | CH₃ | N | O | 220–224° |
| H | H | H | H | OCH₃ | OCH₃ | N | O | 202–210° |
| H | H | H | H | OCH₃ | CH₃ | N | O | 200–204° |
| H | CH₃ | CH₃ | H | OCH₃ | OCH₃ | CH | O | |
| H | CH₃ | CH₃ | H | OCH₃ | CH₃ | CH | O | |
| H | CH₃ | CH₃ | H | CH₃ | CH₃ | CH | O | |
| H | CH₃ | CH₃ | H | CH₃ | OCH₃ | N | O | |
| H | C₂H₅ | CH₃ | H | CH₃ | OCH₃ | CH | O | |
| H | C₂H₅ | CH₃ | H | OCH₃ | OCH₃ | CH | O | |
| H | C₂H₅ | CH₃ | H | OCH₃ | CH₃ | N | O | |
| H | C₂H₅ | CH₃ | H | CH₃ | CH₃ | CH | O | |
| H | H | H | CH₃ | OCH₃ | OCH₃ | CH | O | |
| H | H | H | H | OCH₃ | CH₂OCH₃ | CH | O | |
| H | H | H | H | CH₃ | OC₂H₅ | N | O | |
| H | H | H | H | OCH₃ | CH(OCH₃)₂ | CH | O | |
| H | H | H | H | CH₃ | C₂H₅ | CH | O | |
| H | H | H | H | Cl | NH₂ | CH | O | |
| H | H | H | H | Cl | NHCH₃ | CH | O | |
| H | H | H | H | Cl | N(CH₃)₂ | CH | O | |
| H | H | H | H | Cl | OCH₃ | CH | O | |
| H | CH₃ | CH₃ | H | OCH₃ | OCH₃ | N | O | |
| H | H | H | CH₃ | OCH₃ | CH₃ | N | O | |
| H | H | H | CH₃ | OCH₃ | CH₃ | CH | O | |
| H | CH₃ | CH₃ | H | CH₃ | CH₃ | N | O | |

TABLE IIId

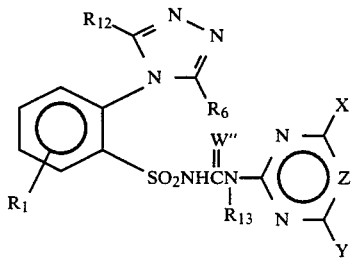

| R₁ | R₆ | R₁₂ | R₁₃ | X | Y | Z | W″ | m.p. (°C.) |
|---|---|---|---|---|---|---|---|---|
| H | H | H | H | CH₃ | CH₃ | CH | O | |
| H | H | H | H | OCH₃ | OCH₃ | CH | O | |
| H | H | H | H | CH₃ | OCH₃ | CH | O | |
| H | H | H | H | CH₃ | CH₃ | N | O | |
| H | H | H | H | OCH₃ | OCH₃ | N | O | |
| H | H | H | H | CH₃ | OCH₃ | N | O | |
| H | H | H | CH₃ | OCH₃ | CH₃ | CH | O | |
| H | H | CH₃ | H | CH₃ | CH₃ | CH | O | |
| H | H | CH₃ | H | OCH₃ | CH₃ | CH | O | |
| H | H | CH₃ | H | OCH₃ | OCH₃ | CH | O | |
| H | H | CH₃ | H | CH₃ | CH₃ | N | O | |
| H | H | CH₃ | H | OCH₃ | OCH₃ | N | O | |
| H | H | CH₃ | H | OCH₃ | CH₃ | N | O | |

TABLE IIId-continued

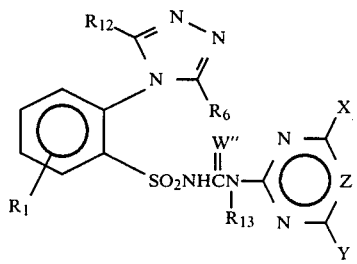

| R₁ | R₆ | R₁₂ | R₁₃ | X | Y | Z | W″ | m.p. (°C.) |
|---|---|---|---|---|---|---|---|---|
| H | CH₃ | CH₃ | H | OCH₃ | OCH₃ | CH | O | |
| H | CH₃ | CH₃ | H | OCH₃ | CH₃ | CH | O | |
| H | CH₃ | CH₃ | H | CH₃ | CH₃ | CH | O | |
| H | CH₃ | CH₃ | H | OCH₃ | OCH₃ | N | O | |
| H | CH₃ | CH₃ | H | OCH₃ | CH₃ | N | O | |
| H | C₂H₅ | CH₃ | H | OCH₃ | OCH₃ | CH | O | |
| H | C₂H₅ | CH₃ | H | OCH₃ | CH₃ | N | O | |
| H | C₂H₅ | CH₃ | H | OCH₃ | CH₃ | CH | O | |
| 5-F | H | H | H | OCH₃ | OCH₃ | CH | O | |
| 6-Cl | H | H | H | OCH₃ | OCH₃ | CH | O | |
| 4-Br | H | H | H | OCH₃ | CH₃ | CH | O | |
| 3-CH₃ | H | H | H | OCH₃ | CH₃ | CH | O | |
| H | H | H | H | CH₃ | CH₃ | CH | O | |
| H | H | H | CH₃ | OCH₃ | CH₃ | N | O | |
| H | CH₃ | CH₃ | H | CH₃ | CH₃ | N | O | |

TABLE IV

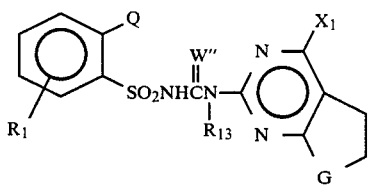

| Q | R₁ | R₁₃ | W″ | X₁ | G | m.p.(°C.) |
|---|---|---|---|---|---|---|
| 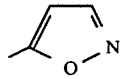 | H | H | O | CH₃ | O | |
| 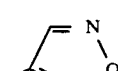 | H | H | O | CH₃ | O | |
| 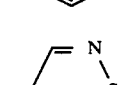 | H | H | O | Cl | S | |
| 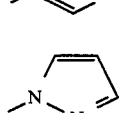 | H | H | O | CH₃ | O | |
| 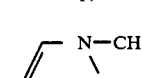 | H | H | O | OCH₃ | O | |
| 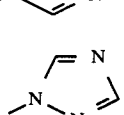 | H | H | O | CH₃ | O | |
| 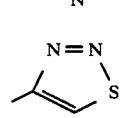 | H | H | O | CH₃ | O | |

TABLE IV-continued

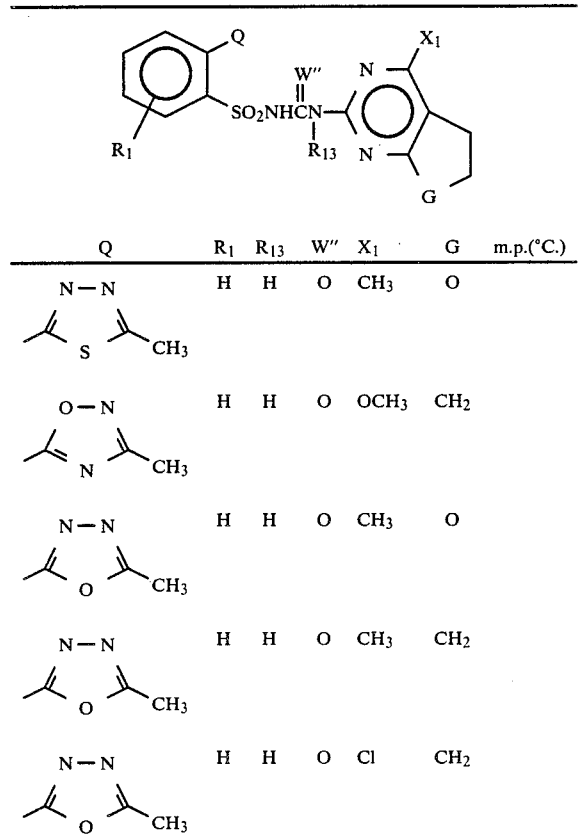

| Q | $R_1$ | $R_{13}$ | W" | $X_1$ | G | m.p.(°C.) |
|---|---|---|---|---|---|---|
| N—N, S, CH₃ | H | H | O | $CH_3$ | O | |
| O—N, N, CH₃ | H | H | O | $OCH_3$ | $CH_2$ | |
| N—N, O, CH₃ | H | H | O | $CH_3$ | O | |
| N—N, O, CH₃ | H | H | O | $CH_3$ | $CH_2$ | |
| N—N, O, CH₃ | H | H | O | Cl | $CH_2$ | |

TABLE V

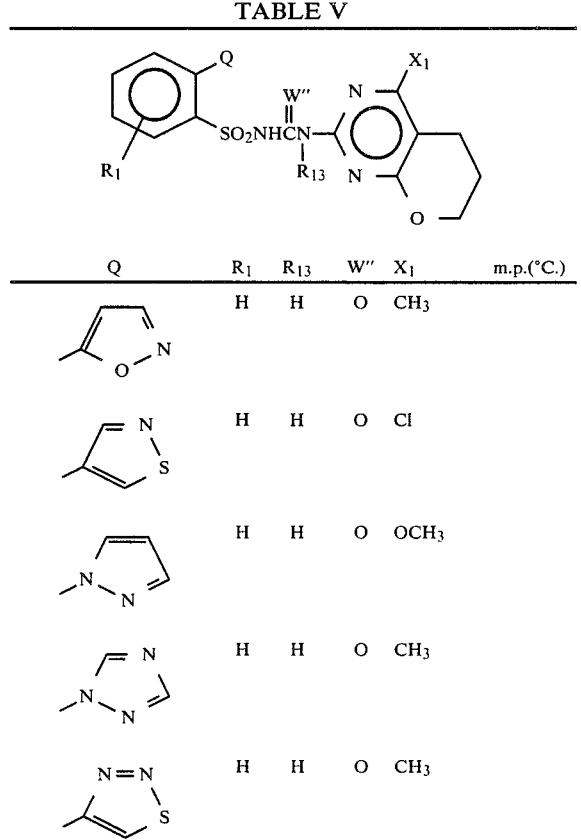

| Q | $R_1$ | $R_{13}$ | W" | $X_1$ | m.p.(°C.) |
|---|---|---|---|---|---|
| isoxazole | H | H | O | $CH_3$ | |
| isothiazole | H | H | O | Cl | |
| N-methylpyrazole | H | H | O | $OCH_3$ | |
| N-methyltriazole | H | H | O | $CH_3$ | |
| thiadiazole | H | H | O | $CH_3$ | |

TABLE V-continued

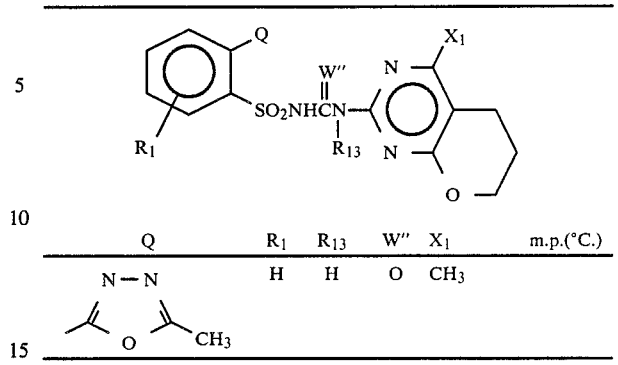

| Q | $R_1$ | $R_{13}$ | W" | $X_1$ | m.p.(°C.) |
|---|---|---|---|---|---|
| N—N, O, CH₃ | H | H | O | $CH_3$ | |

TABLE VI

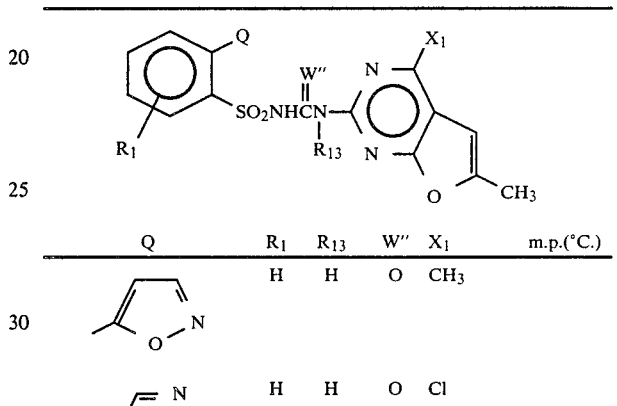

| Q | $R_1$ | $R_{13}$ | W" | $X_1$ | m.p.(°C.) |
|---|---|---|---|---|---|
| isoxazole | H | H | O | $CH_3$ | |
| isothiazole | H | H | O | Cl | |
| N-methylpyrazole | H | H | O | $OCH_3$ | |
| N-methyltriazole | H | H | O | $CH_3$ | |
| thiadiazole | H | H | O | $CH_3$ | |
| N—N, O, CH₃ | H | H | O | $CH_3$ | |

TABLE VII

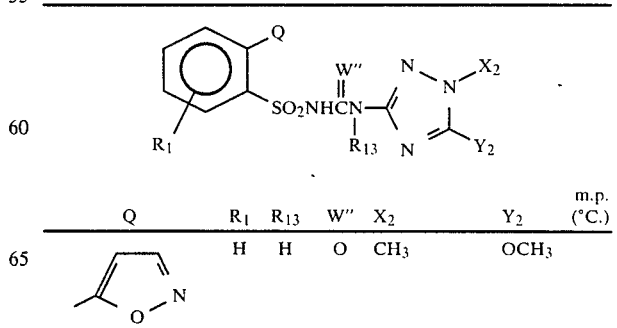

| Q | $R_1$ | $R_{13}$ | W" | $X_2$ | $Y_2$ | m.p. (°C.) |
|---|---|---|---|---|---|---|
| isoxazole | H | H | O | $CH_3$ | $OCH_3$ | |

TABLE VII-continued structure:
benzene ring with Q (ortho), R$_1$ (other position), SO$_2$NHC(=W''')N(R$_{13}$)-[heterocycle with N, X$_2$, Y$_2$]

| Q | R$_1$ | R$_{13}$ | W''' | X$_2$ | Y$_2$ | m.p. (°C.) |
|---|---|---|---|---|---|---|
| isoxazole (N-O) | H | H | O | C$_2$H$_5$ | OCH$_3$ | |
| isoxazole (N-O variant) | H | H | O | CH$_2$CH$_2$CH$_3$ | OCH$_3$ | |
| isothiazole (N-S) | H | H | O | CH$_2$CF$_3$ | OCH$_3$ | |
| N-methylpyrazole (N—CH$_3$, N) | H | H | O | CH$_3$ | OC$_2$H$_5$ | |
| pyrazole | H | H | O | CH$_3$ | OCH$_3$ | |
| oxadiazole (O, N, N-CH$_3$) | H | H | O | CH$_3$ | SCH$_3$ | |
| thiadiazole (N=N, S) | H | H | O | CH$_3$ | OCH$_3$ | |
| thiadiazole (N—N, S, CH$_3$) | H | H | O | CH$_3$ | SC$_2$H$_5$ | |
| pyrazole | H | H | O | CH$_3$ | OCH$_3$ | |
| oxadiazole (O—N, N, CH$_3$) | H | H | O | CH$_2$CF$_3$ | SCH$_3$ | |
| oxadiazole (N—N, O, CH$_3$) | H | H | O | CH$_3$ | OCH$_3$ | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE VIII

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 28

| Wettable Powder | |
|---|---|
| 2-(isoxazol-5-yl)-N—13 [4,6-dimethoxypyrimidin-2-yl)-aminocarbonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 29

| Wettable Powder | |
|---|---|
| 2-(isoxazol-5-yl)-N—[(4-methoxy-6-methylpyrimidin-2-yl)aminocarbonyl]benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 30

| Granule | |
|---|---|
| Wettable Powder of Example 29 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 31

| Extruded Pellet | |
|---|---|
| N—[(4,6-dimethoxypyrimidin-2-yl)aminocarbonyl]-2-(1- and/or 2-methyl-1H—pyrazol-3-yl)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 32

| Oil Suspension | |
|---|---|
| N—[(4,6-dimethoxypyrimidin-2-yl)aminocarbonyl]-2-(1-methyl-1H—pyrazol-4-yl)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 33

| Wettable Powder | |
|---|---|
| N—[(4-methoxy-6-methyl-1,3,5-triazin-2-yl)aminocarbonyl]-2-(1- and/or 2-methyl-1H—pyrazol-3-yl)-benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through U.S.S. No. 50 sieve (0.3 mm opening) and packaged.

EXAMPLE 34

| Low Strength Granule | |
|---|---|
| N—[(4-methoxy-6-methyl-1,3,5-triazin-2-yl)aminocarbonyl]-2-(1-methyl-1H—pyrazol-4-yl)benzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 35

| Aqueous Suspension | |
|---|---|
| N—[(4,6-dimethoxypyrimidin-2-yl)aminocarbonyl]-2-(isoxazol-4-yl)benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 36

| Solution | |
|---|---|
| 2-(isoxazol-4-yl)-N—[(4-methoxy-6-methylpyrimidin-2-yl)aminocarbonyl]benzenesulfonamide, sodium salt | 5% |
| water | 95% |

The salt is added directly to the water with stirring to produce the solution, which may then be packaged for use.

EXAMPLE 37

| Low Strength Granule | |
|---|---|
| 2-(isoxazol-4-yl)-N—[(4-methoxy-6-methyl-1,3,5-triazin-2-yl)aminocarbonyl]benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 38

| Granule | |
|---|---|
| 2-(isoxazol-5-yl)-N—[(4,6-dimethoxypyrimidin-2-yl)-aminocarbonyl]benzenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 39

| High Strength Concentrate | |
|---|---|
| N—[(4,6-dimethoxypyrimidin-2-yl)aminocarbonyl]-2-(1-methyl-1H—pyrazol-4-yl)benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 40

| Wettable Powder | |
|---|---|
| N—[(4,6-dimethoxypyrimidin-2-yl)aminocarbonyl]-2-(1- and/or 2-methyl-1H—pyrazol-3-yl)benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 41

| Wettable Powder | |
|---|---|
| 2-(isoxazol-5-yl)-N—[(4-methoxy-6-methylpyrimidin-2-yl)aminocarbonyl]benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 42

| Oil Suspension | |
|---|---|
| N—[(4-methoxy-6-methyl-1,3,5-triazin-2-yl))aminocarbonyl]-2-(1- and/or 2-methyl-1H—pyrazol-3-yl)benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 43

| Dust | |
|---|---|
| N—[(4-methoxy-6-methyl-1,3,5-triazin-2-yl)aminocarbonyl]-2-(1-methyl-1H—pyrazol-4-yl)benzenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

UTILITY

The compounds of the present invention are powerful herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective pre- or post-emergence weed control in crops, such as wheat, barley, rice, soybeans and corn.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels in the range of about 0.01 to 2 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow.

TEST A

Seeds of crabgrass (Digitaria sp.), barnyard-grass (*Echinochloa crusgalli*), wild oats (*Avena fatua*), sicklepod (*Cassia obtusifolia*), morningglory (Ipomoea sp.), cocklebur (Xanthium sp.), sorghum, corn, soybean, rice, wheat and nutsedge tubers (*Cyperus rotundus*) were planted in a growth medium and treated pre-emergence with a non-phytotoxic solvent solution of the compounds of Table A. At the same time, cotton having five leaves (including cotyledonary ones), bush beans with the third trifoliolate leaf expanding, crabgrass, barnyardgrass and wild oats with two leaves, sicklepod with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three-five leaves were sprayed with a non-phytotoxic solvent solution of the compounds of Table A. Other containers of the above-mentioned weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment.

The following rating system was used:
0=no effect;
10=maximum effect;
C=chlorosis or necrosis;
D=defoliation;
E=emergence inhibition;
G=growth retardation;
H=formative effects;
I=increased chlorophyl;
P=terminal bud kill;
S=albinism;
U=unusual pigmentation;
X=axillary stimulation;
6F=delayed flowering; and
6Y=abscised buds or flowers.

The ratings are summarized in Table A. The compounds tested are highly active herbicides. Certain of the compounds have utility for weed control in wheat.

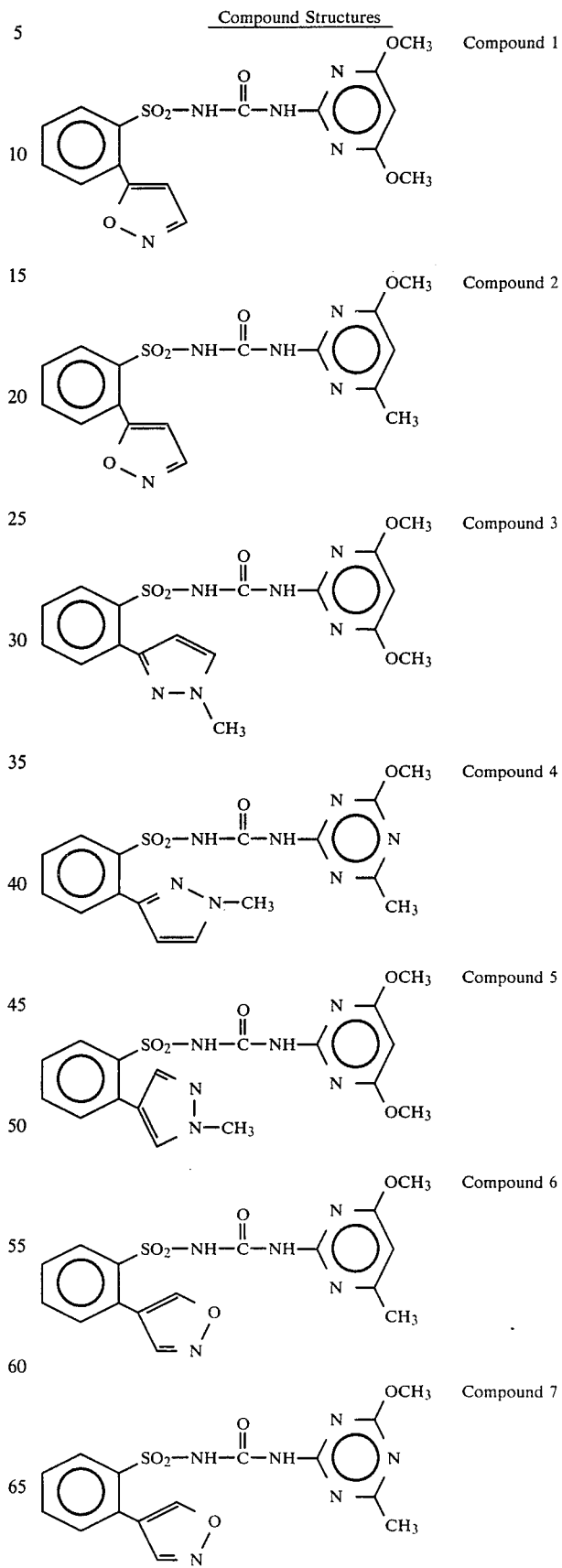

Compound Structures

-continued
Compound Structures
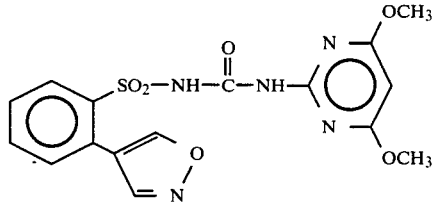
Compound 8
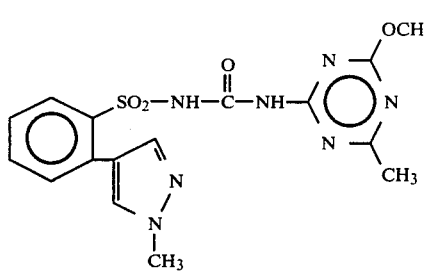
Compound 9
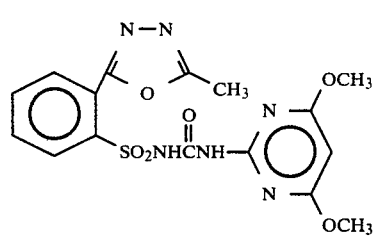
Compound 10
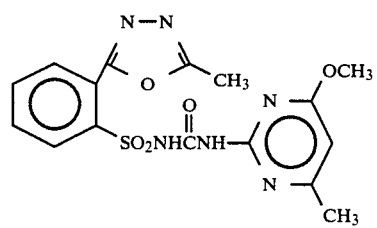
Compound 11
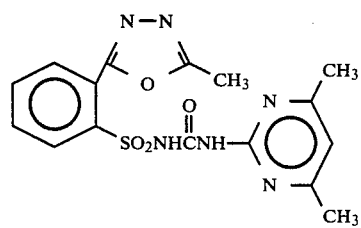
Compound 12
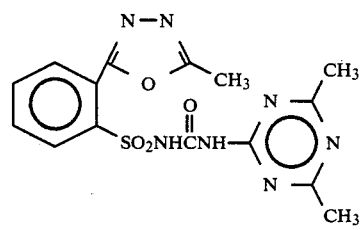
Compound 13
-continued
Compound Structures
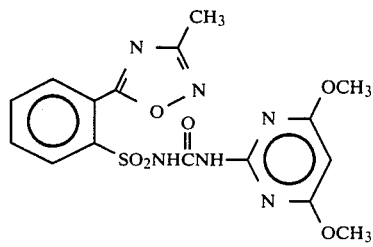
Compound 14
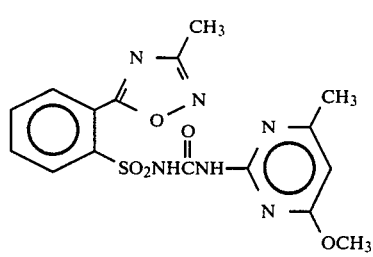
Compound 15
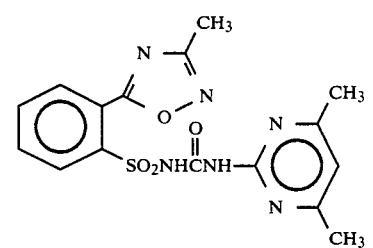
Compound 16
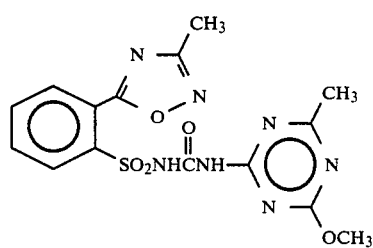
Compound 17
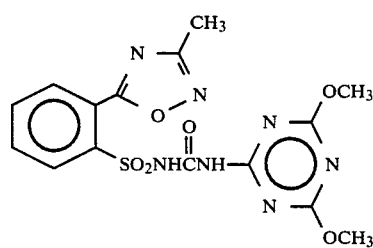
Compound 18
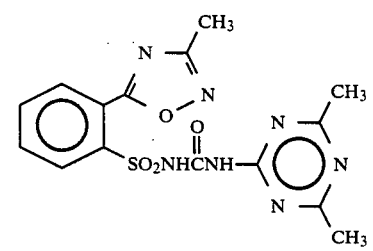
Compound 19

-continued
Compound Structures
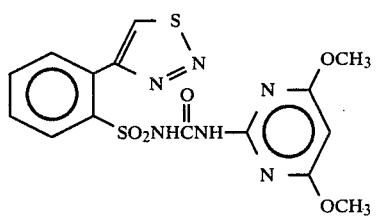
Compound 20
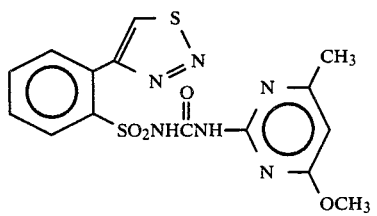
Compound 21
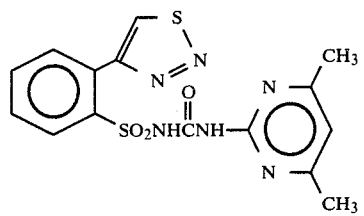
Compound 22
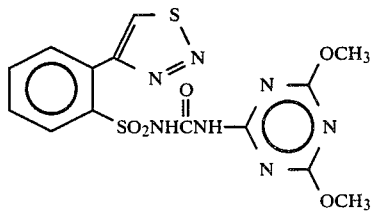
Compound 23
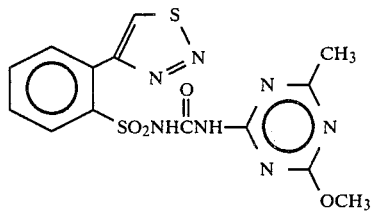
Compound 24
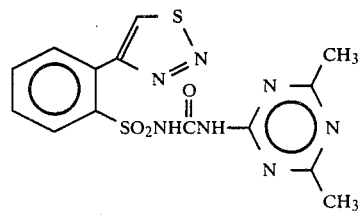
Compound 25
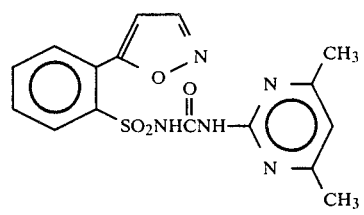
Compound 26
-continued
Compound Structures
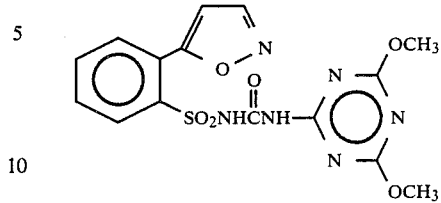
Compound 27
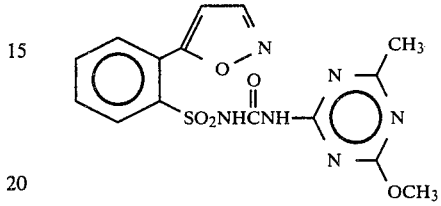
Compound 28
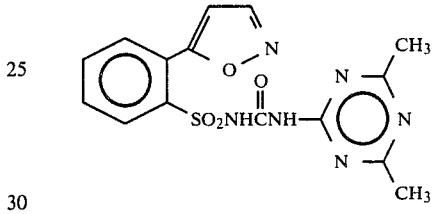
Compound 29
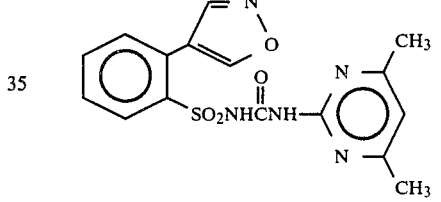
Compound 30
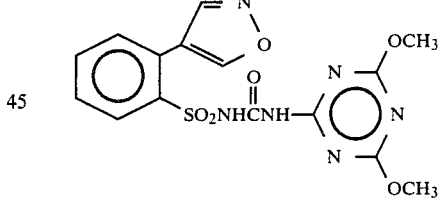
Compound 31
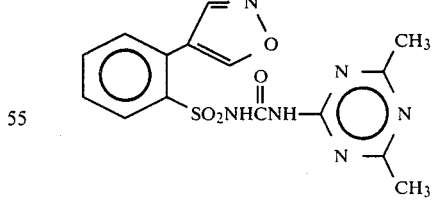
Compound 32
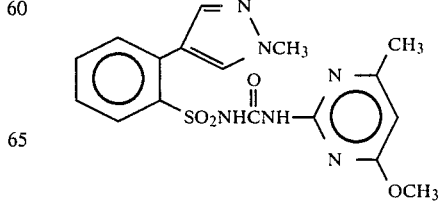
Compound 33

-continued
Compound Structures
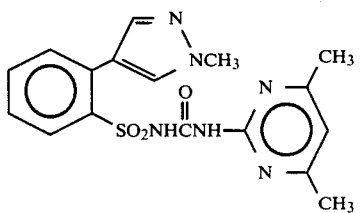
Compound 34
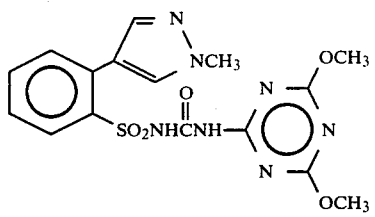
Compound 35
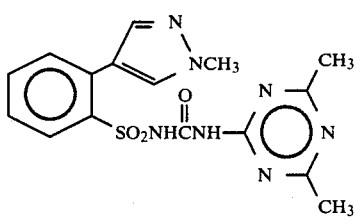
Compound 36
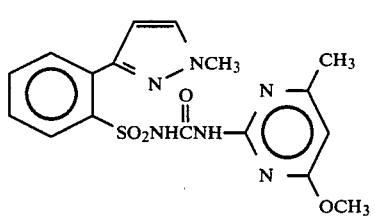
Compound 37
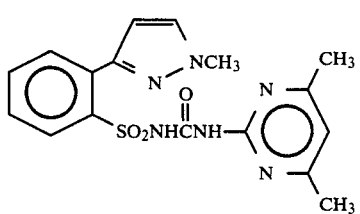
Compound 38
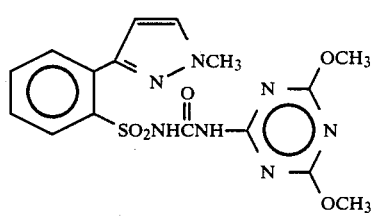
Compound 39
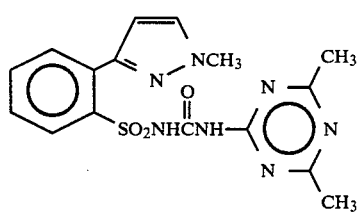
Compound 40
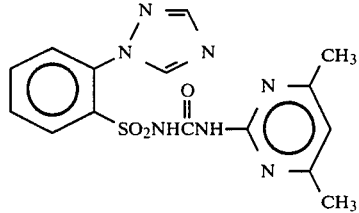
Compound 41
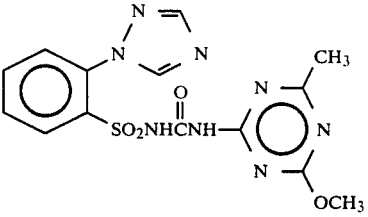
Compound 42
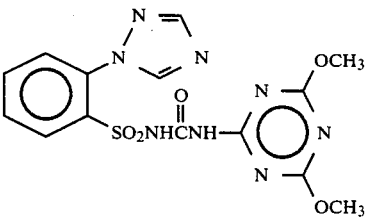
Compound 43
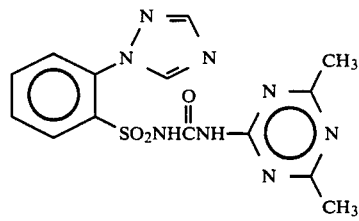
Compound 44
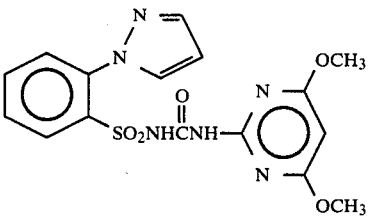
Compound 45
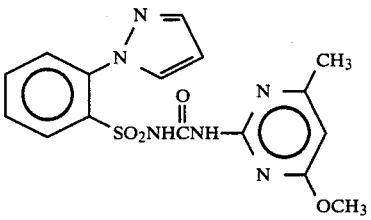
Compound 46
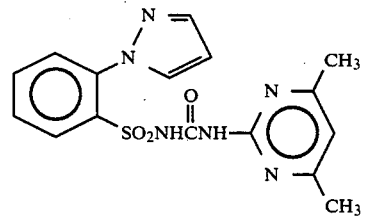
Compound 47

-continued
Compound Structures
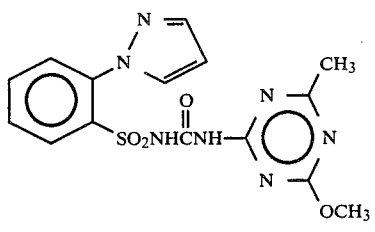
Compound 48
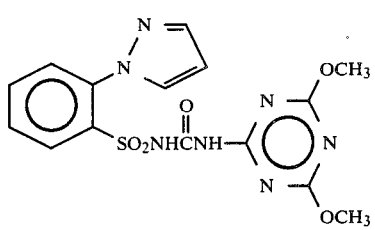
Compound 49
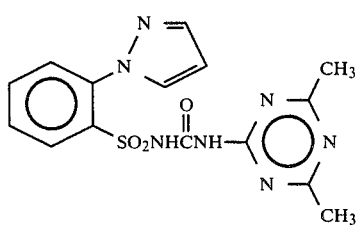
Compound 50
-continued
Compound Structures
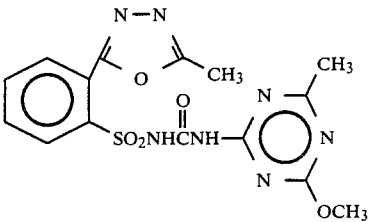
Compound 51
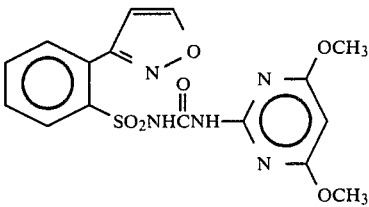
Compound 52
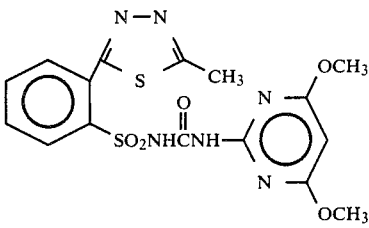
Compound 53
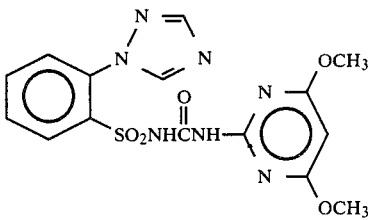
Compound 54
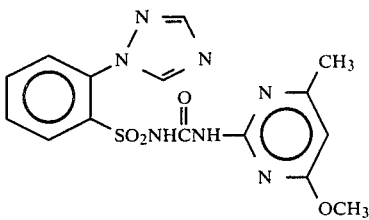
Compound 55

TABLE A

POST-EMERGENCE

| | Cmpd. 1 | Cmpd. 2 | Cmpd. 3 | Cmpd. 3 | Cmpd. 4 | Cmpd. 4 | Cmpd. 5 | Cmpd. 5 | Cmpd. 6 | Cmpd. 7 | Cmpd. 8 | Cmpd. 8 | Cmpd. 9 | Cmpd. 9 |
|---|---|---|---|---|---|---|---|---|---|---|---|---|---|---|
| Rate kg/ha | .05 | .05 | .4 | .05 | .4 | .05 | .4 | .05 | .05 | .05 | .4 | .05 | .4 | .05 |
| Bush bean | 9C | 10C | 9C | 9C | 9C | 5C,9G,6Y | 5C,9G,6Y | 6C,9G,6Y | 9C | 9C | 9C | 9C | 9C | 9C |
| Cotton | 9C | 9C | 6C,9G | 6C,9G | 6C,9G | 5C,9G | 5C,9H | 6C,9G | 6C,9G | 9C | 9C | 6C,9G | 9C | 6C,9G |
| Morningglory | 4C,8G | 10C | 6C,9G | 6C,9G | 5C,9G | 5C,9H | 5C,9H | 6C,9G | 6C,9G | 10C | 10C | 9C | 6C,9G | 9C |
| Cocklebur | 9C | 10C | 6C,9G | 6C,9G | 3C,5H | 4C,5H | 3C,9H | 10C | 6C,9G | 9C | 10C | 6C,9G | 6C,9G | 6C,9G |
| Sicklepod | 9C | 9C | 6C,9G | 6C,9G | 2G | 0 | 4C,9G | 5C,9G | 9C | 9C | 10C | 10C | 6C,9G | 6C,9G |
| Nutsedge | 6C,9G | 4C,8G | 6C,9G | 6C,9G | 2C,8G | 1C | 6C,9G | 5C,9H | 2C,7H | 8C | 3C,7H | 3C,7H | 3C,8G | 3C,8G |
| Crabgrass | 2C,6G | 2C,8G | 5G | 5G | 10C | 9C | 3C,8G | 2C,5H | 9C | 6C,9H | 9C | 9C | 9C | 9C |
| Barnyardgrass | 9C | 9C | 4C,9H | 4C,9H | 2C | 1C | 10C | 10C | 2C,7G | 2C | 9C | 2C,5G | 10C | 5C,9G |
| Wild Oats | 8G,5X | 3C,9G | 2C,9G | 2C,9G | 0 | 0 | 10C | 3C,9H | 9C | 6C,9H | 3C,9G | 2C,8G | 1C | 2C,8G |
| Wheat | 2C,7G | 3C,9G | 3C,9G | 3C,9G | 2C | 0 | 2C,9G | 2C,3G | 2C,9G | 0 | 4C,9G | 5C,9G | 7U,9C | 5U,9C |
| Corn | 5U,9G | 5U,9G | 3U,9G | 3U,9G | 7U,9C | 5C,9G | 5C,9G | 5C,9G | 3C,9G | 5U,9G | 9C | 5U,9C | 9C | 2C,9G |
| Soybean | 9C | 9C | 9C | 9C | 9C | 3C,9G | 6C,9G | 6C,9G | 9C | 9C | 9C | 9C | 9C | 3C,9G |
| Rice | 5C,9G | 6C,9G | 5C,9G | 5C,9G | 1C,3G | 0 | 1C,9H | 5C,9G | 5C,9G | 2C,7G | 6C,9G | 4C,9G | 4C,9G | 4C,9G |
| Sorghum | 3U,9G | 3U,9G | 4U,9G | 4U,9G | 3C,9H | 2C,9G | 1C,9H | 9H | 4U,9C | 3C,8G | 4U,9C | 4U,9C | 6U,9G | 2C,9G |

| | Cmpd. 10 | Cmpd. 11 | Cmpd. 12 | Cmpd. 13 | Cmpd. 14 | Cmpd. 15 | Cmpd. 16 | Cmpd. 17 | Cmpd. 18 | Cmpd. 19 | Cmpd. 20 | Cmpd. 21 | Cmpd. 22 | Cmpd. 23 | Cmpd. 24 | Cmpd. 25 |
|---|---|---|---|---|---|---|---|---|---|---|---|---|---|---|---|---|
| Rate kg/ha | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |
| Bush bean | 9C | 9C | 9C | 6C,9G,6Y | 9C | 9C | 9C | 9C | 9C | 4C,9G,6Y | 9C | 6C,9G,6Y | 9C | 9C | 9C | 5C,9G,6Y |
| Cotton | 5C,9G | 4C,9G | 5C,9G | 4C,8G | 5C,9G | 5C,9G | 4C,9G | 4C,9G | 4C,9G | 3C,4G | 6C,9G | 4C,9G | 5C,9G | 5C,9G | 6C,9G | 4C,9G |
| Sorghum | 10C | 10C | 10C | 5C,9G | 2U,9G | 1C,9G | 9G | 9G | 1C,8H | 2G | 3U,9G | 5U,9G | 9C | 1C,5H | 9C | 2U,9G |
| Corn | 10C | 9C | 9C | 5U,9G | 5U,9G | 4U,9C | 9C | 2C,9G | 3C,9H | 1C,4G | 2U,9H | 2C,9H | 2C,8G | 1U,9H | 2U,9H | 3U,9G |
| Soybean | 10C | 9C | 9C | 1C,2G | 9C | 5C,9G | 4C,9G | 5C,9G | 5C,9G | 4H | 4C,8G | 4C,9G | 5C,9G | 5C,9G | 2C,8G | 3C,9G,5X |
| Wheat | 9C | 9C | 9C | 0 | 1C,6G | 10C | 5C,9H | 0 | 0 | 0 | 1C | 1C,7G | 1C | 1C | 1C,3G | 1C,2G |
| Wild Oats | 9C | 9C | 6C,9G | 5C,9H | 2C,9G | 5C,9G | 5C,9G | 2C | 0 | 0 | 2C | 3C,9H | 1C | 1C | 1C,5G | 1C,4G |
| Rice | 6C,9G | 6C,9G | 9C | 5C,9G | 5C,9G | 5C,9G | 5C,9H | 6G | 1C,2G | 3G | 5C,8G | 5C,9G | 4G | 1C,5G | 5C,9G | 5C,9G |
| Barnyardgrass | 9C | 5C,9G | 9C | 2C,5G | 5C,9G | 5C,9G | 3C,6H | 3C,6H | 0 | 0 | 3C,8G | 6C,9G | 2C,5H | 1C,4H | 1C,4H | 3C,8H |
| Crabgrass | 9G | 9C | 9C | 4C,8H | 5C,9G | 3C,8G | 1C | 1C | 5C,9G | 3C,4G | 2C,8G | 2C,8G | 3G | 0 | 0 | 2C,5G |
| Morningglory | 9C | 5C,9G | 9C | 5C,9H | 4C,8H | 4C,9G | 9C | 9C | 5C,9G | 3C,4H | 3C,8G | 4C,9G | 5C,9G | 5C,9G | 9C | 10C |
| Cocklebur | 9C | 10C | 10C | 5C,9H | 5C,9H | 5C,9G | 9C | 9C | 10C | 4H | 9C | 10C | 10C | 10C | 10C | 10C |
| Sicklepod | 9C | 10C | 10C | 3H,5C | 2C,9G | 5C,9G | 9C | 4C,9G | 5C,9G | 1C | 5C,9G | 5C,9G | 3C,8G | 3C,8G | 6C,9G | 3C,7G |
| Nutsedge | 5C,9G | 10C | 6C,9G | 3C,9G | 2C,8G | 5C,9G | 4C,9G | 5C,9G | 4C,9G | 2C,7G | 9C | 9C | 2C,6G | 4C,8G | 5C,9G | 5C,9G |
| Sugar beet | 9C | 9C | 9C | 5C,8G | 9C | 9C | 1C,9H | 9C | 9C | 4G | 4C,9G | 4C,9C | 4U,9G | 4U,9C | 6U,9C | 2C,9G |

POST-EMERGENCE

| | Cmpd. 26 | Cmpd. 27 | Cmpd. 28 | Cmpd. 29 | Cmpd. 30 | Cmpd. 31 | Cmpd. 32 | Cmpd. 33 | Cmpd. 34 | Cmpd. 35 | Cmpd. 36 | Cmpd. 37 | Cmpd. 38 | Cmpd. 39 | Cmpd. 40 |
|---|---|---|---|---|---|---|---|---|---|---|---|---|---|---|---|
| Rate kg/ha | 0.05 | 0.05 | 0.05 | 0.05 | 0.05 | 0.05 | 0.05 | 0.05 | 0.05 | 0.05 | 0.05 | 0.05 | 0.05 | 0.05 | 0.4 |
| Bush bean | 9C | 9C | 9C | 9C | 9C | 6C,9G,6Y | 4C,9G,6Y | 6C,9G,6Y | 5C,9G,6Y | 3C,9G,6Y | 4C,9G,6Y | 5C,9G,6Y | 4C,5G,6Y | 6C,9G,6Y | 5C,9G,6Y | 6C,6G,6Y |
| Cotton | 5C,9G | 5C,9G | 9C | 5C,9G | 9C | 5C,9G | 4C,9G | 6C,9G | 4C,9G | 3C,9G | 4C,9G | 4C,9G | 2C,5G | 3C,8H | 4C,9G | 4C |
| Sorghum | 2C,7H | 2C,7H | 2C | 1C,9G | 1C,9G | 2C,9G | 1C,9G | 2C,9H | 4C,9G | 2C,7H | 9G | 4C,9G | 3C,7H | 2C,5H | 3U,9G | 3C,8H |
| Corn | 3U,9C | 3C,9G | 3U | 4U,9C | 2U,8G | 9C | 3U,9G | 2C,8G | 2C,9G | 3C,9H | 2C,9H | 2C,9H | 0 | 2C,8H | 3C,9G,5X | 3C,8H |
| Soybean | 4C,8G | 9C | 4G | 9C | 9C | 5C,9G | 6C,9G | 5C,9G | 4C,9G | 4C,9G | 2C,8H | 4C,9G | 1C,5G | 3C,8G | 1C,2G | 3C,9H |
| Wheat | 6C,9G | 9C | 1C | 2C,9H | 8G | 2C,9G | 3G | 2C,9G | 2C,9G | 0 | 2C,9G | 4C,9G | 2C | 0 | 1C,4G | 1C |
| Wild Oats | 0 | 0 | 4C | 9C | 6C,9G | 4C,9G | 2C,9G | 4C,9G | 4C,9H | 4C,9H | 4C,9G | 4C,9G | 4G | 4C,7H | 5C,9G | 2C |
| Rice | 5C,9G | 1C,7G | 5C | 5C,9G | 5C,9H | 4C,9G | 4C,9G | 5C,9H | 6C,9G | 1C,4G | 5C,9G | 4C,8G | 2C,5H | 1C | 5C,9G | 3C,9G |
| Barnyardgrass | 10C | 2C,9H | 5C | 5C,9H | 3C,8G | 5C,9H | 5C,9H | 5C,9H | 2C,9H | 4C,9H | 6C,9H | 5C,8H | 5C,9H | 4C,7H | 5C,9H | 2C,8H |
| Crabgrass | 4C,9G | 1C,5G | 6G | 4C,8H | 3C,8G | 1C,5G | 2C,6G | 3C,9G | 1C,3G | 1C,3G | 1C,6G | 8G | 1C,4G | 1C | 1C,3G | 1C |
| Morningglory | 10C | 10C | 10C | 3C,9G | 10C | 5C,9G | 5C,9G | 5C,9G | 4C,9G | 4C,9G | 5C,9G | 5C,9G | 4C,8G | 4C,8G | 3C,7H | 3C |
| Cocklebur | 10C | 10C | 10C | 9C | 9C | 9C | 9C | 9C | 3C,7G | 3C,8H | 9C | 9C | 2C,2H | 4C,8H | 3C | |

| | | | | | | | | | | | | | | | |
|---|---|---|---|---|---|---|---|---|---|---|---|---|---|---|---|
| Sicklepod | 9C | 5C,9G | 9C | 5C,9G | 5C,9G | 4C,7H | 4C,8H | 5C,8H | 4C,8H | 4C,8H | 5C,8H | 4C,6H | 2C,2H | | 5C | 4C |
| Nutsedge | 5C,9G | 2C,6G | 6G | 2C,6G | 9G | 4G | 8G | 9G | 1C | 8G | 1C,9G | 2C,9G | 5G | | | 0 |
| Sugar beet | — | — | — | — | 5C,9G | 4C,9G | 4C,9G | 2C,8G | 4C,9G | 3C,8H | 2C,7G | 2C,5G | | | 3C,8G | 4C,7G |

TABLE A-continued

| | Cmpd. 40 | Cmpd. 41 | Cmpd. 42 | Cmpd. 43 | Cmpd. 44 | Cmpd. 45 | Cmpd. 46 | Cmpd. 47 | Cmpd. 48 | Cmpd. 49 | Cmpd. 50 | Cmpd. 51 | Cmpd. 52 | Cmpd. 53 | Cmpd. 54 | Cmpd. 55 |
|---|---|---|---|---|---|---|---|---|---|---|---|---|---|---|---|---|
| Rate kg/ha | 0.05 | 0.05 | 0.05 | 0.05 | 0.05 | 0.05 | 0.05 | 0.05 | 0.05 | 0.05 | 0.05 | 0.4 | 0.05 | 0.05 | 0.05 | 0.05 |

POST-EMERGENCE

| | | | | | | | | | | | | | | | | |
|---|---|---|---|---|---|---|---|---|---|---|---|---|---|---|---|---|
| Bush bean | 1C | 4C,9G,6Y | 6C,9G,6Y | 6C,9G,6Y | 1C | 9G | 9D,9G,6Y | 2C,9H,6Y | 9C | 9C | 5C,9G,6Y | 6C,9G,6Y | 9C | 9C | 9C | 5S,9G,6Y |
| Cotton | 1C | 5C,9G | 4C,8H | 4C,4H | 0 | 8H | 6C,9G | 6C,9G | 5C,9H | 5C,9G | 4C,8H | 4C,8G | 5C,9G | 6C,9G | 6C,9G | 5C,9G |
| Sorghum | 1C | 5C,9G | 2C | 3C,4G | 0 | 2C,5G | 3C,9G | 3C,9G | 2C,8H | 4C | 0 | 5U,9G | 5U | 1U,9H | 2C,9G | 5C,9G |
| Corn | 1C | 2C,9G | 2C,8H | 2C | 0 | 0 | 2U,9H | 2U,9H | 5C,8H | 6G | 2C,2H | 9C | 4U | 5C,9G | 2U,9G | 6C,9G |
| Soybean | 1C | 4C,8H | 2C,5H | 2C,2H | 3U,9G | 2C,6H | 3C,8H | 3C,8H | 5C,9G | 4C,9G | 2C,9G | 4C,9G | 5C | 5C,9G | 9C | 6C,9G |
| Wheat | 0 | 3C,9G | 0 | 0 | 5C,9G | 0 | 1C,3G | 1C,3G | 0 | 0 | 0 | 0 | 9G | 1C,7G | 4G | 8G |
| Wild Oats | 1C | 2C,9G | 0 | 0 | 5C,9G | 2C,6G | 3C,9G | 2C,9G | 1C | 0 | 6G | 1C,3G | 2C | 2C,9G | 5G,5X | 2C,9H |
| Rice | 1C | 5C,9G | 2C | 1C | 0 | 2C,9G | 2C,6G | 5C,9G | 4G | 0 | 0 | 8G | 5C | 6C,9G | 4C,9G | 5C,9G |
| Barnyardgrass | 1C | 4C,8H | 2C | 1C | 0 | 9G | 9C | 3C,5H | 0 | 0 | 6G | 5C,9H | 9C | 9C | 5C,9H | 10C |
| Crabgrass | 0 | 1C,4G | 1C | 0 | 0 | 0 | 2C,7G | 3C,5H | 0 | 0 | 0 | 1C,5G | 6C | 3C,7G | 3C,8G | 3C,7G |
| Morningglory | 4C | 5C,9G | 3C | 2C,2H | 5C,9H | 2C,5G | 5C,9G | 5C,9G | 5C,9H | 9C | 4C,9H | 2C,8G | 9C | 5C,9G | 10C | 9C |
| Cocklebur | 1C | 5C,9G | 1C | 1C | 5C,9G | 2C,3G | 5C,9G | 4C,9G | 10C | 8G | 3C,9G | 10C | 9C | 9C | 9C | 9C |
| Sicklepod | 1C | 5C,9G | 3C | 2C,5G | 9C | 0 | 4C,8H | 3C,4H | 5C,9H | 4C,9G | 3C,4H | 4C,8H | 9C | 5C,9G | 9C | 4C,6G |
| Nutsedge | 0 | 2C,5G | 2C | 0 | 10C | 2C,9G | 5C,9G | 4C,8G | 5G | 9G | 2C | 6C,9G | 10C | 6C,9G | 5C,9G | 2C,8G |
| Sugar beet | 1C | — | 0 | — | 5C,9G | — | 9C | 3C,8G | 9C | 9C | 9C | 9C | 9C | 9C | — | — |

| | Cmpd. 1 | Cmpd. 2 | Cmpd. 3 | Cmpd. 3 | Cmpd. 4 | Cmpd. 4 | Cmpd. 5 | Cmpd. 5 | Cmpd. 6 | Cmpd. 7 | Cmpd. 8 | Cmpd. 8 | Cmpd. 9 | Cmpd. 9 |
|---|---|---|---|---|---|---|---|---|---|---|---|---|---|---|
| Rate kg/ha | .05 | .05 | 0.4 | 0.05 | 0.4 | 0.05 | 0.4 | 0.05 | 0.05 | 0.05 | 0.4 | 0.05 | 0.4 | 0.05 |

PRE-EMERGENCE

| | | | | | | | | | | | | | | |
|---|---|---|---|---|---|---|---|---|---|---|---|---|---|---|
| Morningglory | 3C,9G | 9C | 3C,9G | 9G | 3C,9G | 9G | 3C,9G | 2C,8H | 3H | 10C | 1C,9H | 1C,9H | 9C | 1C,9H |
| Cocklebur | 9H | 9H | 9H | 9H | 3C,9H | 8H | 3C,9H | 9H | 2C,7H | 9H | 9H | 9H | — | — |
| Sicklepod | 3C,9G | 3C,9G | 3C,9G | 5C,8G | 3C,7H | 2C,5H | 3C,9G | 5C,9H | 2C,2H | 9C | 3C,9G | 3C,9G | 9C | 7C,9G |
| Nutsedge | 10E | 10E | 10E | 10E | 0 | 0 | 10E | 2C,9H | 2C,4G | 1C,6G | 10E | 10E | 5C,9G | 6G |
| Crabgrass | 2C,5G | 2C,8G | 2C,6G | 1C,3G | 1C | 2C,6H | 2C,6H | 2C,8H | 0 | 1C,3G | 2C,7H | 2C,7H | 4C,8G | 2C,5G |
| Barnyardgrass | 5C,9H | 6C,9H | 6C,9H | 9H | 2C,9H | 1C | 6C,9H | 9H | 2C,6H | 2C,7H | 5C,9H | 5C,9H | 9C | 3C,9H |
| Wild Oats | 2C,9G | 5C,9G | 2C,9G | 2C,9H | 1C | 0 | 3C,9G | 2C,6G | 0 | 2C,6G | 2C,6G | 2C,6G | 3G | 3C,8G |
| Wheat | 2C,9G | 9G | 9G | 2C,9H | 0 | 0 | 1C,9G | 2C,9G | 2C | 2C | 2C,9G | 2C,9G | 3C,9H | 0 |
| Corn | 2U,9G | 9H | 2C,9G | 2C,8H | 2C,9G | 9G | 5C,9G | 3C,9G | 0 | 1C,9G | 3C,9H | 3C,9H | 3C,9H | 2C,8H |
| Soybean | 9H | 10E | 9H | 2C,9H | 9H | 2C,5H | 9H | 2C,9H | 9H | 9H | 2C,8H | 2C,8H | 9H | 3C,9H |
| Rice | 10E | 10E | 10E | 2C,9H | 2C,5G | 0 | 8H | 5C,9H | 10E | 5G | 5C,9H | 5C,9H | 10E | 3C,8G |
| Sorghum | 2C,9G | 9H | 10H | 2C,9H | 2C,9H | 2C,9H | 2C,9H | 2C,8H | 7C,9H | 1C,6H | 7C,9H | 2C,9H | 2C,9H | 9G |

| | Cmpd. 10 | Cmpd. 11 | Cmpd. 12 | Cmpd. 13 | Cmpd. 14 | Cmpd. 15 | Cmpd. 16 | Cmpd. 17 | Cmpd. 18 | Cmpd. 19 | Cmpd. 20 | Cmpd. 21 | Cmpd. 22 | Cmpd. 23 | Cmp. 24 | Cmpd. 25 |
|---|---|---|---|---|---|---|---|---|---|---|---|---|---|---|---|---|
| Rate kg/ha | 0.05 | 0.05 | 0.05 | 0.05 | 0.05 | .05 | .05 | .05 | .05 | .05 | .05 | .05 | .05 | .05 | .05 | .05 |

PRE-EMERGENCE

| | | | | | | | | | | | | | | | | |
|---|---|---|---|---|---|---|---|---|---|---|---|---|---|---|---|---|
| Sorghum | 10H | 10H | 10H | 2C,8H | 10H | 10H | 3C,9H | 4C,9H | 2C,8H | 3H | 5C,9H | 5C,9H | 5C,9H | 5C,9H | 2C,8H | 2C,9H |
| Corn | 5C,9H | 9H | 5C,9G | 4C,7G | 4C,9G | 10E | 3C,9H | 3C,9H | 9H | 2C,7H | 2C,9G | 2C,9G | 10E | 2C,9G | 2C,9H | 2C,9H |
| Soybean | 9H | 9H | 3C,6H | 9H | 9H | 9H | 8H | 2C,9H | 9H | 2C,2H | 2C,2H | 2C,6H | 2C,5H | 3C,4H | 3C,4H | 3C,3H |
| Wheat | 3C,9H | 5C,9G | 10E | 2G | 5C,9G | 5C,9G | 2C,9G | 1C | 2C,6H | 2C,4G | 5G | 1C,9G | 3C,9H | 0 | 3C,5H | 0 |
| Wild Oats | 4C,8G | 6C,9H | 4C,9G | 6H | 5C,9G | 5C,9G | 10E | 3C,6H | 2C,4G | 0 | 7G | 2C,9G | 10E | 1C,3G | 1C,3G | 1C,7G |
| Rice | 10E | 10E | 5C,9H | 2C,5G | 10E | 10E | 10E | 2C,9H | 2C | 2C,9G | 10E | 9H | 10E | 3C,7G | 3C,7G | 3C,8H |
| Barnyardgrass | 5C,9G | 6C,9H | 5C,9G | 5C,7G | 5C,9H | 5C,9H | 5C,9H | 5C,9H | 2C,9G | 0 | 5C,9H | 5C,9H | 5C,9H | 2C,5H | 2C,6H | 10E |
| Crabgrass | 2C,8G | 6C,9H | 5C,9G | 2C,3G | 2C,4G | 3C,7G | 1C,4G | 5C,9H | 2C,9H | 2C,9G | 2C | 2C,5G | 2C,5G | 1C | 2C,6G | 1C,2G |
| Morningglory | 9C | 9C | 9G | 9C | 9H | 9C | 9H | 9C | 9C | 0 | 9C | 5C,9G | 5C,9G | 9C | 9C | 9G |
| Cocklebur | 9H | 9H | 9H | 9G | 9H | 9H | 9H | 9C | 2C,9H | 8H | — | 9H | 8H | 9H | 9H | — |

TABLE A-continued

| | | | | | | | | | | | | | |
|---|---|---|---|---|---|---|---|---|---|---|---|---|---|
| Sicklepod | 9G | 9G | 9G | 1C | 5C,9G | 9C | 8H | 5C,9G | 4C,9G | 3H | 2C,9G | 3C,9G | 5C,9G |
| Nutsedge | 10E | 10E | 10E | 0 | 10E | 10E | 10E | 10E | 10E | 0 | 10E | 10E | 2C,7G |
| Sugar beet | 10E | 10E | 10E | 5G | 10E | 10E | 5C,9G | 9C | 5C,9G | 7G | 5C,9G | 9C | 6C,9G |
| Rate kg/ha | Cmpd. 26 0.05 | Cmpd. 27 0.05 | Cmpd. 28 0.05 | Cmpd. 29 0.05 | Cmpd. 30 0.05 | Cmpd. 31 0.05 | Cmpd. 32 0.05 | Cmpd. 33 0.05 | Cmpd. 34 0.05 | Cmpd. 35 0.05 | Cmpd. 36 0.05 | Cmpd. 37 0.05 | Cmpd. 38 0.05 | Cmpd. 39 0.05 | Cmpd. 40 0.4 |

PRE-EMERGENCE

| | | | | | | | | | | | | | | | |
|---|---|---|---|---|---|---|---|---|---|---|---|---|---|---|---|
| Sorghum | 10H | 1C,6G | 4C,8H | 2C,9H | 5C,9H | 4C,9H | 3C,8G | 5C,9H | 4C,9H | 1C,4G | 2C,8H | 5C,9H | 2C,5G | 3C,5G | 2C,3G |
| Corn | 10H | 3C,9G | 2C,9G | 3U,9H | 9H | 3C,9H | 1C,8G | 9H | 3C,9G | 2C,5G | 2C,5G | 2C,9G | 1C | 4C,8G | 3C,6H |
| Soybean | 9H | 9H | 8H | 8H | 9H | 2C,8H | 1C | 8H | 3C,7H | 0 | 0 | 3C,6H | 0 | 4C,3H | 2C |
| Wheat | 5C,9H | 0 | 4G | 9H | 1C,9H | 8G | 1C,5G | 3C,9G | 3C,9G | 0 | 1C | 2C,9G | 3G | 1C,2G | 0 |
| Wild Oats | 5C,9H | 2C | 2C,6G | 10H | 4C,9H | 8G | 2C,7H | 4C,8G | 4C,8G | 0 | 2C | 4C,8G | 2G | 1C,3G | 0 |
| Rice | 10E | 4C,9H | 5C,9H | 10E | 10E | 3C,8H | 5C,9H | 5C,9H | 3C,9H | 3C,8H | 3C,8H | 3C,9H | 1C | 0 | 2C |
| Barnyardgrass | 5C,9H | 2C,5H | 2C,7H | 10H | 9H | 3C,9H | 3C,7H | 5C,9H | 5C,9H | 2C | 2C,5G | 4C,9H | 2C,4G | 2C,5G | 2C |
| Crabgrass | 2C,8G | 2C | 2C | 2C,5G | 1C,7G | 2C | 0 | 3C,9G | 2C,8H | 9G | 1C | 2C,7G | 2G | 0 | 1G |
| Morningglory | 9H | 9H | 9C | 9G | 7G | 9G | 1C | 9G | 9C | 9G | 2C,7C | 9C | 2C,4G | 3C,8H | 3C,7H |
| Cocklebur | 9H | 9H | 9H | 9H | 9H | 2C,3H | 1C | 9H | 9H | 9H | — | 9H | 2C | 3C,9H | 0 |
| Sicklepod | 9G | 9G | 9G | 9G | 9G | 2C,2H | 4C,6H | 2C,8G | 3C,8G | 2C,7G | 2C,5G | 8G | 2C | 3C | 0 |
| Nutsedge | 10E | 10E | 10E | 10E | 10E | 9G | 0 | 10E | 10E | 7G | 8G | 2C,7G | 4G | 1C | 0 |
| Sugar beet | 10E | 10E | 10E | 10E | 10E | 4C,9G | 10E | 10E | 4C,9G | 10E | 3C,6G | 0 | 0 | 3C,7G | 2G |
| Rate kg/ha | Cmpd. 40 0.05 | Cmpd. 41 0.05 | Cmpd. 42 0.05 | Cmpd. 43 0.05 | Cmpd. 44 0.05 | Cmpd. 45 0.05 | Cmpd. 46 0.05 | Cmpd. 47 0.05 | Cmpd. 48 0.05 | Cmpd. 49 0.05 | Cmpd. 50 0.05 | Cmpd. 51 0.05 | Cmpd. 52 0.05 | Cmpd. 53 0.05 | Cmpd. 54 0.05 | Cmpd. 55 0.05 |

PRE-EMERGENCE

| | | | | | | | | | | | | | | | |
|---|---|---|---|---|---|---|---|---|---|---|---|---|---|---|---|
| Sorghum | 1C | 3C,6G | 0 | 1C | 0 | 9C | 9C | 4C,9H | 2C,9H | 2C,7H | 3G | 2C,9H | 10H | 5C,9H | 10E | 6C,9H |
| Corn | 1C | 4C,7G | 1C | 2C,5G | 0 | 9H | 5C,9H | 3C,9H | 3C,8H | 3C,8H | 2C,4G | 5C,9H | 9H | 2C,8H | 2C,9H | 5C,9H |
| Soybean | 0 | 1C,1H | 0 | 0 | 0 | 9H | 9H | 3C,7H | 2C,8H | 9H | 2C,4H | 4C,7H | 9H | 3C,5H | 9H | 9H |
| Wheat | 0 | 4G | 0 | 0 | 0 | 0 | 1C,7G | 4G | 0 | 0 | 0 | 1C | 2C,8G | 8G | 6G | 2C,9H |
| Wild Oats | 0 | 1C,3G | 0 | 0 | 0 | 3C,5G | 2C,9G | 3C,9G | 3C,4G | 1C | 2C,4G | 1C | 2C,9G | 2C,8H | 2C,6G | 3C,9H |
| Rice | 1C | 3C,5H | 0 | 0 | 0 | 5C,9H | 5C,9H | 4C,9G | 0 | 0 | 0 | 5C,8G | 10E | 10E | 10E | 9H |
| Barnyardgrass | 1C | 1C | 2H | 1C | 0 | 4C,9H | 2C,8H | 2C | 1C | 1C | 2C,4G | 2C,7H | 3C,9G | 5C,9H | 3C,9H | 3C,9H |
| Crabgrass | 3G | 0 | 2G | 2G | 0 | 1C,3G | 2C | 1C | 0 | 0 | 0 | 0 | 2C,3G | 1C,5G | 3C,7G | 3C,6G |
| Morningglory | 0 | 8H | 0 | 0 | 0 | 9C | 9C | 9H | 9C | 9C | 2C,8H | 8G | 9C | 9C | 9C | 2C,9G |
| Cocklebur | 2G | 8H | 0 | 0 | 0 | 9H | 9H | 9H | 2C,8H | 9H | 2C,7G | 9H | 8G | 9H | 9H | 9H |
| Sicklepod | 0 | 2C | 0 | 0 | 0 | 5C,9G | 5C,9G | 8G | 5C,9G | 2C,8H | 2C,7G | 8G | 9C | 5C,9G | 9H | 2C,9G |
| Nutsedge | 3G | 0 | 0 | 0 | 0 | 10E | 9G | 9G | 7G | 7G | 3G | 2C,9G | 10E | 10E | 9G | 2C,8G |
| Sugar beet | 0 | — | 0 | 0 | 0 | 10E | 5C,9G | 3C,9H | 5C,9G | 5C,9G | 2C,6H | 4C,8G | 4C,9G | 10E | 10E | 10E |

TEST B

Two plastic bulb pans were filled with fertilized and limed Fallsington silt loam or Woodstown sandy loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyard-grass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B. Note that the compounds are highly active herbicides, and that several of them have utility for selective weed control in crops such as wheat or soybeans (e.g., see Compound Nos. 22, 23 and 24).

TABLE B
PRE-EMERGENCE ON FALLSINGTON SILT LOAM SOIL

| | Compound 1 | | Compound 2 | | Compound 3 | | Compound 4 | | Compound 5 | | Compound 6 | | Compound 7 | | Compound 8 | | Compound 9 | | Compound 10 | |
|---|---|---|---|---|---|---|---|---|---|---|---|---|---|---|---|---|---|---|---|---|
| Rate kg/ha | 0.03 | 0.12 | 0.03 | 0.12 | 0.03 | 0.12 | 0.06 | 0.25 | 0.03 | 0.12 | 0.015 | 0.03 | 0.03 | 0.12 | 0.03 | 0.12 | 0.03 | 0.12 | 0.015 | 0.06 |
| Crabgrass | 5G | 6G | 7G | 7G | 0 | 0 | 0 | 4G | 2G | 7G,3H | 0 | 5G,5C | 0 | 4G | 2G | 2G | 0 | 3G | 8G | 9G |
| Barnyardgrass | 7G | 10C | 10C | 10C | 2G | 8G,9C | 6G,3H | 9G,7C | 9G,5H | 9G,9C | 5G,5C | 6G,5H | 2G | — | 4G,2H | 9G,9C | 3G,3H | 9G,8C | 9G | 9G,9C |
| Sorghum | 8G,5H | 10C | 10E | 10E | — | — | — | — | 5G,3H | 0 | 2G | 6G,3H | — | — | — | 0 | — | 10C | 10C | 10C |
| Wild Oats | 5G | 5G | 10E | 7G,3H | — | — | 0 | 2G | 6G,3H | 8G | 6G | 2G | 0 | 6G,3H | 0 | 0 | 3G,3H | 6G,3H | 7G | 9G,9C |
| Johnsongrass | 7G,5H | 9G,8C | 9G,9C | 9G,9C | 4G | 7G,3H | 3G | 6G,3H | 6G,3H | 5G | 6G | 2G | 0 | 6G,3H | 3G | 3G | 0 | 7G,5C | 6G | 9G,9C |
| Dallisgrass | 6G | 6G | 8G,3H | 0 | 0 | 0 | 0 | 3G | 5G | 5G | 2G | 2G | 0 | 6G,3H | 4G | 3G | 0 | 5C,6G | 6G | 9G |
| Giant foxtail | 6G | 8G,8C | 9G,9C | 10C | 7G,5C | 4G,5H | 2G | 6G,3H | 6G,3H | 5G,3H | 3G | 3G | 0 | 0 | 4G,3H | 8G,8C | 3G | 10C | 8G | 9G,9C |
| Ky. bluegrass | 8G,5C | 9G,9C | 8G,9C | 10C | 5G | 8G,8C | 2G | 7G,7C | 6G | 10C | — | 0 | 7G,5C | 3G | 0 | 10C | 10C | 5C,6G | 8G | 9G |
| Cheatgrass | 10C | 10E | 10E | 10E | 2G | 6G,5H | 4G | 7G | 6G,3C | 8G,8C | — | 7G,5H | 3G | 10C | 8G,8C | 10C | 0 | 10C | 9G | 9G,9C |
| Sugar beets | 10C | 10E | 10E | 10E | 0 | 2H,5G | 8G,7C | 9G,9C | 8G,8C | 8G,8C | 10C | 7G | 10C | 10C | 10C | 10C | 10C | 6G,5H | 7G | 9G,9C |
| Corn | 3G | 5G | 7G,5H | 8G,5H | 0 | 5G,3H | 4G | 10E | 4G,3H | 5G,5H | — | 9G,9C | 7G,5H | 7G,5H | 3G,2U | 6G,5H | 2U | 10C | 10C | 10C |
| Mustard | 10E | 10E | 10E | 10C | 7G,5H | 10C | 8G,5H | 9G,8C | 8G,5H | 9G,5H | 7G | 9G,9C | 10C | 10C | 10C | 10C | 10C | 10C | 10C | 10C |
| Cocklebur | 3G | 5G | 6G,3H | 8G,5H | 0 | 10C | 3G | 7G,7C | 0 | 4G,3H | 6G,5H | 2G | 9G,9C | 9G,9C | 4G,3H | 7G,5H | 8G,9C | 6G,5H | 7G | 9G |
| Pigweed | 10E | 10E | 10E | 10E | 0 | 5G,3H | 7G | 9G,9C | 0 | 8G,8C | 0 | 8G,8C | 10C | 10C | 10C | 10C | — | 10C | — | 8G |
| Nutsedge | 6G | 8G | 8G | 10E | 5G | 5G | 0 | 4G | 4G | 5G | 6G,3H | 7G | 5G | 9G | 3G | 3G | 8G | 10C | 10C | — |
| Cotton | 7G | 9G,9C | 9G,8C | 10C | 4G | 8G | 2G | 5G,5H | 3G | 5G,3H | 5G | 5G | 9G,5H | 5G | 3G | 8G,5H | 5G,3H | 3G | 9G | 9G |
| Morningglory | 6G,3C | 6G,3H | 9G,8C | 8G,5H | 0 | 8G,5H | 6G,3H | 8G,5H | 3G | 4G,3H | 0 | 0 | 10C | 8G,5H | 3G | 6G,5H | 6G,5H | 6G,5H | 10C | 10C |
| Sicklepod | 7G | 8G,8C | 9G,8C | 8G,5C | 0 | 3H | 3G | 5G,3H | 3G | 7G,7C | 6G,3H | 7G | 9G,7C | 7G | 6G,3H | 7G,3H | 7G,3H | 6G,5H | 10C | 8G |
| Teaweed | 6G,3H | 8G,8C | 8G,8C | 10C | 0 | 3H | 2C | 6G,3H | 2G | 9G,9C | 5G | 9G | 9G,9C | 9G,9C | 3G | 3G,2C | 2C | 3G,2C | 8G | 8G |
| Velvetleaf | 7G,5H | 10C | 9G,9C | 10C | 0 | 5G,3H | 3C | 7G,5H | 2G | 4G,3H | 0 | 9G | 9G,9C | 9G,9C | 4G,3H | 6G,5H | 2C,4G | 6G,5H | 9G | 9G,9C |
| Jimsonweed | 6G | 8G,7C | 10C | 10C | 0 | 7G,5H | 0 | 8G,3H | 3G | 8G,3H | 3H,5G | 10C | 10C | 10C | 3H,4G | 3G,2H | 3G | 2C,4G | 7G | 7G,7H |
| Soybean | 4G,2H | 7G,5H | 5G,5H | 8G,8C | 0 | 5G,5H | 6G,5H | 8G,5H | 2G | 5G,4H | 6G | 5G,3H | 9G,9C | 5G,4H | 3G | 3G,2H | 3G | 3G | 10C | 10C |
| Rice | 7G | 8G,8C | 7G,5C | 9G,9C | 3G | 6G,3H | — | 5G | 7G | 9G,5H | 7G | 8G,5H | 7G,3H | 9G,5H | 7G,3H | 7G,3H | 3G | 7G,3H | 10C | 7G,7H |
| Wheat | 5G | 5G | 7G | 8G,6C | 3G | 5G | — | 0 | 0 | 3G | 0 | 3G | 3G | 7G | 2G | 0 | 0 | 3G | 6G | 6G |

| | Compound 11 | | Compound 12 | | Compound 20 | | Compound 21 | | Compound 22 | | Compound 23 | | Compound 24 | | Compound 26 | | Compound 27 | | Compound 28 | | Compound 29 | | Compound 30 | |
|---|---|---|---|---|---|---|---|---|---|---|---|---|---|---|---|---|---|---|---|---|---|---|---|---|
| Rate kg/ha | 0.015 | 0.06 | 0.03 | 0.06 | 0.03 | 0.12 | 0.03 | 0.12 | 0.03 | 0.12 | 0.03 | 0.12 | 0.03 | 0.12 | 0.03 | 0.12 | 0.03 | 0.12 | 0.03 | 0.12 | 0.03 | 0.12 | 0.03 | 0.12 |
| Crabgrass | 8G | 8G | 3G | 5G | 5G | 5G | 6G | 7G | 5G | 7G | 0 | 0 | 5G | 5G | 9G | 9G | 5G | 5G | 4G | 5G | 5G | 8G | 4G | 8G |
| Barnyardgrass | 9G | 9G,9C | 9G | 9G,9C | 9G | 9G | 6G | 9G | 8G | 9G | 3G | 4G | 3G | 7G | 9G,9C | 10C | 5G | 9G | 5G | 6G | 5G | 9G | 9G,9C | 10C |
| Sorghum | 10C | 10C | 10C | 10C | 9G | 9G | 10C | 10C | 9G | 9G | 7G | 8G | 8G | 9G | 10C | 10C | 5G | 10C | 10C | 10C | 7G | 10C | 10C | 10C |
| Wild Oats | 8G | 10C | 8G | 8G | 4G | 9G | 7G | 9G | 9G | 9G | 0 | 0 | 3G | 3G | 8G | 8G | 3G | 4G | 3G | 4G | 10C | 8G | 7G | 8G |
| Johnsongrass | 8G | 9G,9C | 8G | 9G,9C | 9G | 9G | 9G | 9G | 9G | 9G | 0 | 10C | 5G | 9G,9C | 9G,9C | 10C | 4G | 9G,9C | 3G | 9G | 7G | 10C | 4G | 10C |
| Dallisgrass | 8G | 8G | 8G | 9G | 8G | 8G | 9G | 9G | 9G | 9G | 4G | 0 | 2G | 8G | 8G | 10C | 2G | 10C | 0 | 3G | 10C | 8G | 8G | 9G |
| Giant foxtail | 9G | 9G,9C | 9G | 9G,9C | 8G | 8G | 9G | 9G | 9G | 9G | 0 | 5G | 6G | 10C | 10C | 10C | 2G | 10C | 2G | 6G | 8G | 10C | 6G | 10C |
| Ky. bluegrass | 9G | 9G,9C | 9G | 9G,9C | 9G | 9G | 9G | 10C | 9G | 10C | 5G | 6G | 6G | 10C | 10C | 10C | 3G | 10C | 8G | 10C | 10C | 10C | 10C | 10C |
| Cheatgrass | 9G | 10C | 9G | 10C | 8G | 10C | 10C | 10C | 9G | 10C | 2G | 8G | 6G | 10C | 10C | 10C | 10C | 10C | 10C | 10C | 10C | 10C | 4G | 10C |
| Sugar beets | 10C | 10C | 10C | 10C | 10C | 10C | 10C | 10C | 9G | 10C | 5G | 10C | 7G | 7G | 10C | 10C | 10C | 10C | 4G | 10C | 8G | 10C | 4G | 10C |
| Corn | 9G | 9G | 8G | 8G | 7G | 9G | 8G | 10C | 9G | 10C | 8G | 8G | 9G | 9G | 7H,8G | 10C | 6G,5H | 10C | 10C | 10C | 10C | 9G | 6G | 8G |
| Mustard | 10C | 10C | 10C | 10C | 10C | 10C | 10C | 10C | 9G | 10C | 7G | 7G | 10C | 9G | 10C | 10C | 7G,5H | 7G,3H | 7G | 10C | 10C | 10C | 10C | 10C |
| Cocklebur | 10C | 10C | 8G | 8G | 8G | 10C | 10C | 10C | 9G | 10C | 9G | 9G | 9G | 9G | 8G,7H | 10C | 9G | 6G,2H | 10C | 10C | 9G | 9G,9C | 9G | 10C |
| Pigweed | — | — | 10C | 10C | 5G | 7G | 10C | 10C | — | 8G | — | — | — | — | 10C | 10C | — | 10C | 4G | 10C | 9G | 8G | 7G | 9G |
| Nutsedge | 10C | 10C | 8G | 9G | 5G,3H | 6G,3H | 9G | 9G | 9G | 9G | 5G | 4G | 4G | 10C | 10C | 10C | 7G | 7G | 4G | 8G | 8G | 8G | 10C | 10C |
| Cotton | 8G | 8G | 8G | 7G | 5G,3H | 5G,3H | 7G | 7G | 8G | 9G | 5G | 6G | 6G | 8G | 10C | 10C | 9G | 9G | 10C | 10C | 8G | 8G | 6G | 6G |
| Morningglory | 9G | 9G | 10C | 8G | 6G,3H | 5G,5H | 7G | 7G | 6G | 9G | 6G | 6G | 5G | 8G | 9G,9C | 9G | 8G | 7G | 4G | 8G | 10C | 8G | 4G | 6G |
| Sicklepod | 9G | 9G | 8G | 7G | 7G,5H | 7G,5H | 8G | 9G | 7G | 8G | 5G | 7G | 6G | 7G | 9G | 8G | 7G | 8G | 10C | 8G | 10C | 8G | 8G | 8G |
| Teaweed | 8G | 8G | 8G | 8G | 6G,3H | 6G,5H | 8G | 10C | 9G | 10C | 8G | 9G | 6G | 7G | 9G | 10C | 7G | 6G | 6G | 6G | 8G | 6G | 8G | 8G |
| Velvetleaf | 9G | 9G | 9G | 9G | 5G | 5G | 9G | 9G | 9G | 9G | 7G | 9G | 8G | 9G | 9G | 9G | 8G | 7G | 4G | 7G | 6G | 8G | 8G | 8G |

TABLE B-continued
PRE-EMERGENCE ON
FALLSINGTON SILT LOAM SOIL

| | Compound 31 | | Compound 32 | | Compound 33 | | Compound 34 | | Compound 35 | | Compound 36 | | Compound 37 | | Compound 53 | | Compound 54 | | Compound 55 | |
|---|---|---|---|---|---|---|---|---|---|---|---|---|---|---|---|---|---|---|---|---|
| Rate kg/ha | 0.12 | 0.03 | 0.12 | 0.03 | 0.12 | 0.03 | 0.12 | 0.03 | 0.12 | 0.03 | 0.12 | 0.03 | 0.12 | 0.03 | 0.12 | 0.03 | 0.12 | 0.015 | 0.12 | 0.03 | 0.015 |
| Crabgrass | 2G | 0 | 5G | 0 | 8G,3C | 6G,3C | 6G | 3G | 2G | 0 | 0 | 0 | 5G | 0 | 5G | 2G | 2G | 0 | 5G | 2G | 0 |
| Barnyardgrass | 6G | 3G | 8G | 4G | 9G,9C | 9G,9C | 9G,9C | 5G | 6G | 5G | 5G | 4G | 8G | 6G | 9G | 7G | 8C,8C | 7G,5H | 6G,3C | 5G | 2G |
| Sorghum | 5G | 2G | 9G | 4G,3H | 9G | 9G | 9G | 3G | 7G,5H | 3G | 9G | 6G,3H | 10C | 9G | 9G,9C | 9G,9C | 10C | 10C | 10C | 9G,7H | 8G,5H |
| Wild Oats | 4G | 2G | 9G | 5G | 9G | 6G | 8G | 6G | 5G | 5G | 6G | 2G | 7G | 5G | 6G | 5G | 4G | 2G,3H | 0 | 4G | 2G |
| Johnsongrass | 6G | 5G | 8G | 7G | 9G | 8G | 9G | 7G | 5G | 4G | 9G | 3G | 9G | 8G | 9G | 5G | 5H,6G | 0 | 0 | 9G,8H | 5G,5H |
| Dallisgrass | 0 | 0 | 0 | 0 | 9G | 8G | 9G | 2G | 0 | 0 | 8G | 0 | 8G | 5G | 8G | 5G | 2G | 5G | 4G | 6G | 0 |
| Giant foxtail | 2G | 0 | 9G | 4G | 9G | 8G | 9G | 6G | 3G | 2G | 0 | 0 | 3G | 3G | 9G | 5G | 7G | 5G | 4G | 7G,5C | 3G |
| Ky. bluegrass | 3G | 2G | 10C | 7G | 10C | 9G | 9G | 7G | 9G | 8G | 4G | 0 | 3G | 3G | 9G | 8G | 9G | 8G | 7G | 9G,9C | 7G |
| Cheatgrass | 5G | 2G | 10C | 8G | 9G,9C | 9G,9C | 9G,9C | 5G | 5G | 3G | 7G | 0 | 3G | 3G | 10C | 9G | 9G | 8G | 8G | 9G,9C | 7G |
| Sugar beets | 10C | 10C | 10C | 9G | 9G | 7G | 8G | 4G | 9G | 8G | 3G | 2G | 8G,8C | 4G | 10C | 9G | 10C | 9G | 9G | 10C | 8G |
| Corn | 5G | 3G | 9G,9C | 9G | 8G,7H | 8G,5H | 9G,9C | 5G | 5G | 2G | 3G | 0 | 3G | 3G | 6G | 4G | 8G,5C | 9G,7H | 3G | 8G,7H | 6G,5H |
| Mustard | 9G | 8G | 9G | 2G | 10C | 9G | 9G | 4G | 8G | 3G | 9G | 2G | 10C | 9G | 8G | 9G | 9G,9C | 9G,5H | 9G | 10C | 9G,9C |
| Cocklebur | 8G | 5G | 9G | 2G | 9G | 3G | 2G | 0 | 8G | 3G | 5G | 0 | 5G | 3G | 5G | 6G | 7G,7H | 3G | 9G,9C | 6G,7H | 5G,5H |
| Pigweed | — | — | — | — | — | — | — | — | — | — | — | — | — | — | — | — | — | — | — | — | — |
| Nutsedge | 9G | 8G | 8G | 8G | 8G | 9G | 9G | 6G | 7G | 4G | 0 | 0 | 6G | 6G | 10C | 10C | 10C | 10C | 10C | — | — |
| Cotton | 9G | 7G | 6G | 6G | 8G | 8G | 5G | 4G | 8G | 3G | 0 | 0 | 2G | 7G | 8G | 5G | 8G,5H | 6G | 7G | 6G,3C | 2G |
| Morningglory | 9G | 6G | 5G | 5G | 8G | 4G | 6G | 2G | 8G | 2G | 0 | 0 | 3G | 5G | 7G | 5G | 8G,7H | 6G,7H | 5G,5H | 7G | 4G |
| Sicklepod | 9G | 6G | 8G | 5G | 2G | 0 | 2G | 0 | 5G | 0 | 0 | 0 | 0 | 3G | 8G | 2G | 6G,5H | 5G,3H | 3G | 7G | 4C |
| Teaweed | 8G | 6G | 5G | 5G | 8G | 6G | 8G | 5G | 5G | 5G | 3G | 0 | 2G | 0 | 9G | 4G | 7G | 7G | 6G | 10C | 3G |
| Velvetleaf | 7G | 3G | 9G | 0 | 5G | 2G | 5G | 0 | 3G | 0 | 0 | 0 | 5G | 2G | 9G | 9G | 10C | 10C | 6G | 8G | 7G |
| Jimsonweed | 9G | 5G | 5G | 2G | 9G | 8G | 7G | 0 | 2G | 3G | 3G | 0 | 5G | 0 | 9G,9C | 5G | 5G | 4G | 3G | 3G | 2G |
| Soybean | 9G | 8G,5H | 9G | 6G | 7G,3C | 5G | 6G | 2G | 3G | 2G | 2G | 2G | 8G | 4G | 6G,7H | 3G,5H | 8G,5H | 7G,5H | 7G,3H | 8G,7H | 6G,5H |
| Rice | 7G | 3G | 10C | 10C | 10C | 9G | 10C | 6G | 7G | 2G | 9G | 7G | 9G | 10C | 10C | 10C | 10C | 10C | 8G | 9G | 7G |
| Wheat | 2G | 0 | 7G | 0 | 9G | 3G | 9G | 6G | 0 | 0 | 9G | 7G | 8G | 3G | 3G | 2G | 2G | 3G | 0 | 4G | 2G |

TEST C

Two ten-inch in diameter plastic pans lined with polyethylene liners were filled with prepared Woodstown sandy loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola kali*), tansy mustard (*Descuraina pinnata*), Galium aparine, tumble mustard (*Sisymbrium altissium*) kochia (*Kochia scoparia*), shepherd's purse (*Capsella bursapastoris*), Matricaria inodora, black nightshade (*Solanum nigrum*), yellow rocket (*Barbarea vulgaris*), wild mustard (*Brassica kaber*) or rapeseed and wild buckwheat (*Polygonum convolvulus*). Sometimes, Veronica persica was included among the test species. The above two pans were treated pre-emergence. At the same time two pans in which the above plant species were growing were treated post-emergence. Plant height at the time of treatment ranged from 1–15 cm depending on plant species.

The compounds applied were diluted with a non-phytotoxic solvent and sprayed over-the-top of the pans. An untreated control and a solvent alone control were included for comparison. The treatments were maintained in the greenhouse for 20 days at which time the treatments were compared to the controls and the effects visually rated. The recorded data are presented in Table C. It will be seen that the compounds have utility for weed control in cereal crops, such as wheat and barley.

TABLE C

| | Compound 4 | | | | Compound 7 | | | | Compound 35 | | | |
|---|---|---|---|---|---|---|---|---|---|---|---|---|
| | Pre-Emergence | | Post-Emergence | | Pre-Emergence | | Post-Emergence | | Pre-Emergence | | Post-Emergence | |
| Rate kg/ha | 0.01 | 0.03 | 0.01 | 0.03 | 0.015 | 0.06 | 0.015 | 0.06 | 0.06 | 0.015 | 0.06 | 0.015 |
| wheat | 0 | 1G | 0 | 5G | 0 | 0 | 0 | 2G | 0 | 0 | 0 | 0 |
| barley | 0 | 2G | 0 | 0 | 0 | 4G | 0 | 1G | 0 | 0 | 0 | 0 |
| wild oats | 0 | 2G | 0 | 0 | 2G | 2G | 0 | 0 | 0 | 0 | 0 | 0 |
| downy brome | 1C | 3G | 2G | 7G | 4G | 6G | 4G | 5G | 3G | 0 | 0 | 0 |
| cheatgrass | 1C,2G | 2C,6G | 0 | 7G | 2G | 1C,3G | 4G | 5G | 3G | 0 | 0 | 0 |
| blackgrass | 0 | 2C,4G | 0 | 5G | 1C,5G | 2C,8G | 1C,7G | 1C,6G | 2G | 0 | 0 | 0 |
| annual bluegrass | 0 | 4G | 0 | 3G | 5G | 6G | 6G | 6G | 4G | 0 | 0 | 0 |
| green foxtail | 2C,2G | 2C,3G | 0 | 0 | 1C,4G | 1C,5G | 6G | 5G | 0 | 0 | — | — |
| quackgrass | 2G | 3G | 0 | 2G | — | — | 5G | 4G | 0 | 0 | 2G | 0 |
| Italian ryegrass | 1C,2G | 2G | 0 | 2G | 5G | 1C,7G | 5G | 5G | 5G | 0 | 4G | 0 |
| ripgut brome | 1C,4G | 1C,6G | 0 | 6G | 1C,3G | 1C,6G | 5G | 4G | 4G | 0 | 2G | 0 |
| Russian thistle | 2G | 4G | 0 | 7C,6G | 1G,2G | 2C,5G | 4C,8G | 10C | 0 | 0 | 8C,9G | — |
| tansy mustard | 4G | 9G | 8G | 10C | 2C,9G | 1C,9G | 7C,8G | 10C | — | — | 10C | 10C |
| Galium aparine | — | — | 8G | 5C,8G | 7G | 1C,8G | 5G | 3C,7G | 2C,8G | 2C,5G | 7G | 3C,8G |
| tumble mustard | 7G | 9G | 10C | 10C | 2C,9G | 5C,9G | 5C,9G | 10C | 10C | 3C,9G | 9C,9G | 10C |
| kochia | 6G | 7G | 3G | 2C,2G | 5C,8G | 7C,9G | — | — | 3G | 0 | 3C,3G | 7G |
| shepherd's purse | 8G | 8G | — | — | 5C,9G | 2C,9G | 10C | 9C,9G | 8C,9G | 8G | 8G | 3G |
| Matricaria inodora | 0 | 4G | 7C,7G | 9C,9G | 1C,9G | 3C,9G | 7C,9G | 8C,9G | 8C,9G | 8G | 3C,8G | 5G |
| black nightshade | 3G | 5G | 0 | 0 | 2G | 1C,8G | 1C,4G | 10C | 3C,9G | 5G | 7G | 4G |
| yellow rocket | 2C,2G | 3C,5G | — | — | 2C,9G | 2C,9G | 2C,8G | 2C,9G | 7G | 4G | 4G | 3G |
| rapeseed | 1C,3G | 3C,7G | 10C | 10C | 2C,8G | 3C,9G | 10C | 10C | 9G | 5G | 3C,9G | 5G |
| wild buckwheat | 1C,3G | 2C,6G | 2C,8G | 9C,9G | 3C,8G | 4C,9G | 3C,7G | 7C,9G | 2C,8G | 4G | 8G | 5G |
| Veronica persica | | | | | | | | | | | 3G | 3G |

| | Compound 27 | | | | Compound 28 | | | | Compound 32 | | | |
|---|---|---|---|---|---|---|---|---|---|---|---|---|
| | Pre-Emergence | | Post-Emergence | | Pre-Emergence | | Post-Emergence | | Pre-Emergence | | Post-Emergence | |
| Rate kg/ha | 0.06 | 0.015 | 0.06 | 0.015 | 0.06 | 0.015 | 0.06 | 0.015 | 0.06 | 0.015 | 0.06 | 0.015 |
| wheat | 0 | 0 | 1G | 2G | 1G | 0 | 2G | 2G | 4G | 0 | 1G | 0 |
| barley | 0 | 0 | 2G | 2G | 2G | 0 | 3G | 2G | 5G | 0 | 3G | 0 |
| wild oats | 3G | 0 | 4G | 3G | 3G | 3G | 4G | 2G | 8G | 4G | 2G | 3G |
| downy brome | 4G | 2G | 7G | 4G | 8G | 5G | 7G | 5G | 8G | 2C,8G | 7G | 6G |
| cheatgrass | 4G | 0 | 3G | 4G | 8G | 3G | 6G | 4G | 2C,7G | 7G | 5G | 6G |
| blackgrass | 5G | 0 | 3G | 2G | 3C,9G | 5G | 7G | 5G | 5C,9G | 2C,7G | 3C,8G | 2C,7G |
| annual bluegrass | 7G | 3G | 3G | 2G | 8C,9G | 6G | 8G | 6G | 5C,9G | 3C,8G | 2C,8G | 2C,7G |
| green foxtail | 5G | 0 | — | — | 2C,8G | 4G | — | — | 7C,9G | 3C,6G | — | — |
| quackgrass | 5G | 0 | 4C | 5G | 7G | 5G | 4G | 3G | 8G | 8G | 10C | 7G |
| Italian ryegrass | 5G | 2G | 6G | 5G | 2C,8G | 6G | 7G | 5G | 5C,9G | 3C,8G | 7C,9G | 8G |
| ripgut brome | 7G | 0 | 5G | 4G | 2C,8G | 7G | 6G | 3G | 8G | 7G | 7G | 5G |
| Russian thistle | 2C,5G | 2G | 9C | 9C | 5C,8G | 2C,5G | 10C | 10C | 0 | 0 | 10C | 10C |
| tansy mustard | 8G | 10C | 10C | 10C | 10C | 10C | 10C | 10C | 10C | — | 10C | 10C |
| Galium aparine | 8G | 6G | 10C | 10C | 10C | 4G | 5G | 5G | 5G | 2C,5G | 7G | 3G |
| tumble mustard | 10C | 10C | 10C | 10C | 10C | 10C | 10C | 9G,9C | 10C | 9G | 10C | 9G,9C |
| kochia | 7G | 6G | 2G | 0 | 10C | 9G | 10C | 10C | 9G | 0 | 9G,9C | 10C |
| shepherd's purse | 10C | 10C | 10C | 10C | 10C | 10C | 10C | 10C | 10C | 8G | 10C | 10C |
| Matricaria inodora | 9C,9G | 8C,9G | 10C | 8C,8G | 9G,9C | 9C,9G | 10C | 10C | 8G | 6G | 10C | 8C,8G |
| black nightshade | 8G | 7G | 5G | 4G | 8G | 7G | 10C | 8G | 5G | 6G | 9C,9G | 5G |
| yellow rocket | 9G | 2C,8G | 4G | 4G | 10C | 9C,9G | 10C | 10C | 8G | 5G | 8G | 10C |
| rapeseed | 10C | 5C,9G | 9G,9C | 8C,8G | 8C,9G | 9C,9G | 10C | 10C | 8G | 5G | 10C | 7C,8G |
| wild buckwheat | 3C,9G | 8G | 10C | 6G | 3C,9G | 3C,8G | 10C | 9C,9G | 2C,9G | 7G | 9C,9G | 9C,8G |
| Veronica persica | | | 5G | 0 | | | 10C | 10C | | | 5G | 3G |

TEST D

The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table D.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), Sicklepod (*Cassia obtusifolia*), morningglory (*Ipomoea hederacea*), jimsonweed (*Datura stramonium*), cocklebur (*Xanthium pensylvanicum*), crabgrass (Digitaria sp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and mustard or rape. All plants were sprayed approximately 14 days after planting. Additional plant species such as johnsongrass and bindweed are sometimes added to this standard test in order to evaluate unusual selectivity.

Several of the compounds tested by this procedure are useful for the post-emergence control of weeds in crops such as rice, wheat, soybeans (see Compound No. 22) and corn (see Compound Nos. 7 and 23).

TABLE D

| | Compound 1 | | | | Compound 2 | | | Compound 3 | | | Compound 4 | | Compound 5 | | | Compound 6 | | |
|---|---|---|---|---|---|---|---|---|---|---|---|---|---|---|---|---|---|---|
| Rate kg/ha | 0.06 | 0.015 | 0.004 | 0.001 | 0.06 | 0.015 | 0.004 | 0.06 | 0.015 | 0.004 | 0.06 | 0.015 | 0.06 | 0.015 | 0.004 | 0.06 | 0.015 | 0.004 |
| Soybeans | 10G,4C | 10G,5C | 3C,9G | 6G | 10G,6C | 10G,4C | 3C,9G | 9G,8C | 9G,2C | 7G | 9G,4C | 8G,2C | 10G,6C | 10G | 6G,4C | 9G | 9G | 9G |
| Velvetleaf | 8G,5C | 10C | 10C | 6G | 10C | 10C | 10C | 7G,3C | 9G,9C | 8G | 9G,2C | 7G,6C | 10C | 10C | 3C,5G | 8G | 8G | 2G |
| Sesbania | 10C | 9G,4C | 10C | 10C | 10C | 10C | 10C | 9G | 10C | 3C,7G | 8G,2C | 6G | 9G,2C | 9G | 3C,5G | 10C | 10C | 7G |
| Sicklepod | 10G,6C | 10C | 9G | 7G | 10C | 10C | 9G | 3G,4C | 8G,2C | 6G | 9G,2C | 8G,2C | 10G | 8G,2C | 3C,4G | 10G | 3G,2C | 0 |
| Cotton | 10G,7C | 10C | 10C | 8G | 10C | 10C | 8G | 8G | 8G,2C | 5G | 8G,2C | 5G,2C | 9G,4C | 8G,2C | 10G,4C | 8G,4C | 8G,4C | 4G,2C |
| Morningglory | 10C | 10C | 8G | 4G | 9G,2C | 9G,2C | 9G,4C | 9G,6C | 9G,4C | 4G | 8G,5C | 5G,3C | 10C | 9G,2C | 10G | 9G,4C | 9G,4C | 4G |
| Alfalfa | 10C | 10C | 6C,8G | 10C | 10C | 10C | 10C | 5G | 5G | 2C | 7G,6C | 7G,6C | 9G,8C | 7G,5C | 1C,2G | 5G | 5G | 0 |
| Jimsonweed | 9G | 10C | 5G | 3G | 9G | 9C,9G | 7G | 6G | 2G | 1G | 2C | 4G | 4C | 4G | 3G,2C | 5G | 5G | 0 |
| Cocklebur | 9G | 9G,8C | 7G | 2G | 9G | 9G | 7G | 2H,5G | 4G | 1C,4G | 9G | 8G | 9G | 8G | 1C | — | — | 3G,1C |
| Corn | 9G,8C | 10C | 7G,3H | 1G | 10C | 10C | 3H,9G | 0 | 1G,1H | 0 | 7G,4U | 6G,4U | 8G,4C | 10P | 0 | 8G | 9G,1U | 7G,2H |
| Crabgrass | 0 | 0 | 3G | 0 | 0 | 0 | 6G | 6G | 3G | 2G | 2G | 0 | — | — | 3G | 6G | 6G | 6G |
| Rice | 8G,5C | 2C,3G | 4G | 2G | 8G,7C | 5G,6C | 7G | 7G | 6G,4C | 3G | 3G | 2G,2C | 6G,6C | 5G | 4G | 5G | 5G | 2G |
| Nutsedge | 10C | 9G | 9G | 0 | 10C | 10C | 8G | 1G | 6G | 0 | 0 | 0 | 7G | 4G | 6G,7C | 8G | 8G | 0 |
| Barnyardgrass | 10C | 10C | 9G,9C | 7G | 10C | 10C | 9G | 7G | 6G,2C | 3G | 5G | 8G | 8G,2C | 8G,2C | 3G | 8G | 8G,2H | 4G,2H |
| Wheat | 4G | 0 | 4G | 0 | 6G,6C | 2G,2C | 3G | 7G | 5G | 0 | 0 | 0 | 6G | 0 | 6G | 8G | 6G | 0 |
| Giant foxtail | 9G,7C | 9G,7C | 3G | 4G | 9G,9C | 5G,5C | 8G | 6G | 4G | 1G | SG | 8G | 6G | 5G,4C | 2G | 6G | 6G | 2G |
| Wild Oats | 3G | 0 | 0 | 0 | 7G,2C | 3G | 0 | 2G | 4G,2C | 4G | 0 | 0 | 5C | 0 | 5G | 4G | 6G | 0 |
| Sorghum | 7G,6C | 5C,6G | 8G | 2G | 10C | 6G,7C | 9G | 6G | 9G,7C | 7G | 6G | 6G | 10C | 4G | 3G,2C | 8G | 8G | 1H,4G |
| Sunflower | 10C | 10C | 5G | 4G | 10C | 10C | 9G | 7G | 5G | 9C | 10C | 10C | 10C | 10P | 2H,6C | 8G | 8G | 6G,3H |
| Mustard | 10C | 10C | 9G,8C | 9G,6C | 10C | 10C | 10C | 5G | 5G | — | 9G | 9G,4C | 10C | 6G,3C | — | 9G,5C | 9G,1U | 7G |
| Johnsongrass | 8G,5C | 5G,5C | 0 | 0 | 10C | 10C | 7G | 4G | 4G | 2C | 4G | 4G | 10C | 4G | 4G | 8G,6C | 6G | 6G |
| Sugar beets | 10C | 9G,9C | 9G | 9G,6C | 8G,8C | 10C | 9G | 2C | 5G | 0 | 9C,9C | 9G,3C | 9C,9C | 8G | 1G | 8G,2U | 5G | 2G |
| Bindweed | 10C | 8G | 0 | 0 | 10C | 10C | 6G | 0 | 0 | 0 | 8G | 4G | 8G | 4G | 4C,2G | 8G | 6G | 3G |
| Rape | | | | | | | | | | 9C | | | | | | | | |

| | Compound 7 | | Compound 8 | | | Compound 9 | | | Compound 20 | | Compound 21 | | Compound 22 | | Compound 23 | | Compound 24 | |
|---|---|---|---|---|---|---|---|---|---|---|---|---|---|---|---|---|---|---|
| Rate kg/ha | 0.015 | 0.004 | 0.06 | 0.015 | 0.004 | 0.06 | 0.015 | 0.001 | 0.06 | 0.015 | 0.06 | 0.015 | 0.06 | 0.015 | 0.06 | 0.015 | 0.06 | 0.015 |
| Soybeans | 10G,2C | 10C | 10C | 10C | 10G | 10G,5C | 8G | 5G | 10C | 8G,6C | 10C | 7G,4C | 7G,4C | 3G | 9G,7C | 5G,1C | 9C | 7G,2C |
| Velvetleaf | 7G,2C | 8G | 10C | 10C | 10C | 9G,5C | 8G,2C | 3G,4C | 10C | 10C | 9G | 9G | 9G | 9G | 7G | 9G | 10C | 9G |
| Sesbania | 9G,4C | 10C | 10C | 10C | 10C | 10C | 2C,8G | 5G | 10C | 10C | 10C | 10C | 10C | 10C | 10C | 10C | 10C | 8G |
| Sicklepod | 10C | 10G | 10C | 10G | 10C | 9G | 7G,5C | 0 | 10C | 9G | 10C | 10C | 8G | 6G | 10C | 10C | 10C | 8G |
| Cotton | 10C | 8G | 10C | 10C | 8G | 10C | 9G | 2C,7G | 10C | 8G,7C | — | — | 9C | 7C,8G | 9G | 10C | 10C | 10C |
| Morningglory | 9G,6C | 8G | 9G,6C | 9G,4C | 9G,9C | 10C | 9G,4U | 4G | 10C | 8C,7G | 6G,2C | 6G,2C | 8G,7C | 6G | 9G | 9C | 9G | 6G |
| Alfalfa | 8G | 9G | 4C,8G | 2C,7G | 9G,4C | 7C,3C | 6C,2C | 4G | 7G | 7G | 9C | — | 7G | 8G | 9G | 6G | 6G | 6G |
| Jimsonweed | 9G,2C | 9G | — | 6G | 3G | 7G | 9G | 4G | 0 | 2G | 10C | 6G,2C | 9G | 9G | 3G | 3G | 7G | 5G |
| Cocklebur | 9G | 10C | 9G | 8G | 8G | 8G | 8G | 5G | 3G | 3G | 10C | 7G | 7G,4C | 8G | 3G | 4G | 7G | 2G |
| Corn | 0 | 1H | 8G,1H | 7G,1H | 0 | 9G | 1H,7G | 6G,1H | 0 | 0 | 8G | 7G | 9C | 9C | 4G | 0 | 2G | 1G |
| Crabgrass | 3G | 0 | 3G | 2G | 6G | 3G | 2G | 0 | 6G | 3G | 0 | 4G | 9G | 7C,8G | 0 | 0 | 4G | 0 |
| Rice | 0 | 0 | 5G | 6C,6G | 4G | 3G | 2G | 0 | 6G | 3G | 3G | 0 | 9G | 6G | 1G | 0 | 2G | 2G |
| Nutsedge | 10C | 0 | 8G,3C | 8G | 6G | 2G | 6G,2C | 2C | 10C | 10C | 3G | 3G | 9C | 7G | 4C,5G | 1G | 3G | 1G |
| Barnyardgrass | 10C | 9G | 8G,4C | 8G | 4G | 3G | 0 | 4G | 4G | 4G | 8G | 8G | 9G | 1G | 0 | 0 | 1G | 0 |
| Wheat | 0 | 8G | 7G | 3G | 2G | 0 | 0 | 4G | 3G | 1G | 5G | 3G | 4G | 10C | 1C | 0 | 2G | 0 |
| Giant foxtail | 10C | 10G | 4C,8G | 3G | 6G | 0 | 6G,2C | 4G | 4G | 4G | 5G | 3G | 9G | 0 | 4C,5G | 0 | 3G | 0 |
| Wild Oats | 0 | 0 | 4G | 3G | 2G | 6G,2C | 4C,2C | 4G | 4G | 1G | 5G | 3G | 9G | 0 | 0 | 0 | 1G | 9G |
| Sorghum | 1H | 0 | 7G | 3G | 4G | 0 | 9G | 2G | 3G | 4G | 2G | 2G | 4G | 4G | 3G | 0 | 0 | 0 |
| Sunflower | 10C | 10C | 10P | 7G,7C | 10C | 9G,5C | 9G,3C | 3C,5G | 9G | 9G | 8G | 9G | 8G | 10C | 10C | 10C | 10C | 10C |
| Mustard | 10P | 10C | 9G,8C | 6G | 6G,5C | 9G,6C | 7G,6C | 4G,3C | — | — | 10C | 10C | 10C | 10C | — | — | — | — |
| Johnsongrass | 10C | 9G | 4G | 6G | 5C | 6G | 3G | 7G | 2G | 2G | 7G | 7G | 10C | 9G | 1G | 1G | 0 | 0 |
| Sugar beets | 9G,9C | 9G | 9G | 9G | 8G | 7G | 5G | 0 | 10C | 4C,5G | 10C | 8G | 10C | 0 | 10C | 10C | 10C | 10C |
| Bindweed | 8G | 0 | 7G | 1H,9G | 8G | 6G | 6C | — | — | — | — | — | 3G | — | 7G | 7G | 7G | 7G |

TABLE D-continued

|  | | | Compound 41 | | Cmpd. 54 | | | Compound 55 | | |
| --- | --- | --- | --- | --- | --- | --- | --- | --- | --- | --- |
| Rate kg/ha | | | 0.06 | 0.015 | 0.015 | 0.06 | 0.015 | 0.004 | 0.001 |
| Soybeans | | | 10C | 9C | 10C | 10C | 10C | 6G,7C | 7G,4C |
| Velvetleaf | | | 8G | 7G | 9G | 10C | 10C | 6G | 4G |
| Sesbania | | | 8G | 7G | 10C | 10C | 10C | 4G | 3G |
| Sicklepod | | | 9G | 8G | 8G | 8G | 4G | 7G | — |
| Cotton | | | 10C | 10C | 10C | 8C | 9G | 9G | 9G |
| Morningglory | | | 6G,4C | 4G | 10C | 8G | 8G | — | 6G |
| Alfalfa | | | 7G | 4G | 10C | 8C | 4C,9G | 7G | 6G |
| Jimsonweed | | | 8G | 9G | 9G | 6C,5G | 4G,5C | 4G | 6G |
| Cocklebur | | | 10C | 10C | 7G | 10C | 6G | 5G | 3G |
| Corn | | | 7C | 4G | 7G | 9G | 3C,8G | 4G | 3G |
| Crabgrass | | | 2G | 3G | 2G | 4G | 0 | 0 | 1G |
| Rice | | | 3C,6G | 1G | 8C | 2G,6C | 3C | 2G | 0 |
| Nutsedge | | | 9C | 0 | 8G | 4G,4C | 3G | — | 0 |
| Barnyardgrass | | | 1G | 3G | 0 | 8G | 7G | 3G | 2G |
| Wheat | | | 5G | 6G | — | 5G | 4G | 1G | 0 |
| Giant foxtail | | | 6G | 7G | 0 | 7G | 6G | 3G | 1G |
| Wild Oats | | | 8G | 7G | 8G | 7G | 7G | 4G | 2G |
| Sorghum | | | 8G | 7G | 10C | 8G | 8G | 8G | 6G |
| Sunflower | | | 6G | 3G | — | 9G | 4G | 8G | 4G |
| Mustard | | | — | — | — | — | — | — | — |
| Johnsongrass | | | 8G | 4G | 0 | 3C | 2G,1C | 0 | 0 |
| Sugar beets | | | 10C | 10C | 7G | 9G | 9C | 9G | 9G |
| Bindweed | | | 5G | 1G | 4G | 9G | 9G | 8G | 6G |
| Rape | | | 10C | 8C | 10C | 10C | 10C | 8C | 6G |

TEST E

This test was designed to evaluate the potential utility of compounds from within the scope of the invention for selective weed control in rice. The crop was transplanted into simulated paddies containing soil and propagules of barnyardgrass (Echinochloa sp.), water chestnut (Eleocharis sp.), and arrowhead (Sagittaria sp.). Three days after transplanting, the test chemicals were applied to the paddy water in a non-phytotoxic solvent at the rates shown in Table E. The paddies were maintained in a greenhouse, and plant response ratings were taken several weeks after application utilizing the rating system as described for Test A. Several of the compounds tested have potential utility for selective weed control in rice.

TABLE E

| Cmpd. No. | Rate (g/ha) | Rice | Barnyard-grass | Water Chestnut | Arrow-head |
|---|---|---|---|---|---|
| 1 | 0.5 | 0 | 9E | 3G | 3G |
| | 1 | 2C | 7E | 7G | 10G |
| | 2 | 2G | 10E | 10C | 3G |
| | 4 | 5G,2C | 10E | 10G,3C | 7G |
| | 5 | 3G | 6F,4E | 10C | 5G |
| | 20 | 10G,5C | 10E | 10C | 10C |
| 2 | 10 | 9G,2C | 10E | 7G | 10G |
| | 40 | 10G,5C | 9C | 8G,3C | 10E |
| 7 | 25 | 0 | 4G | — | 9G |
| | 100 | 0 | 4G | 8G | 10G,3C |
| 8 | 5 | 0 | 9C | — | 5G,3H |
| | 20 | 5I | 10C | 10C | 8G,2C |
| 5 | 5 | 0 | 9C | 3G | 2G,2H |
| | 10 | 5G | 8C | 6G | 5G,3H |
| | 20 | 7G | 10C | 9G | 9G |
| | 40 | 9G,3C | 10C | 9G,2C | 9G |
| 35 | 10 | 0 | 8C | 6G | 0 |
| | 40 | 0 | 10C | 9G | 9G,3H |

What is claimed is:

1. A compound of the formula:

SO₂NHC(W''')N(R₁₃)—A, with Q and R₁ substituents on phenyl ring where Q is

[structures of pyrazole, isoxazole, thiazole, triazole, thiadiazole rings with various R substituents]

W''' is O or S;
W is O, S or NR;
W' is O or S;
R is H or $C_1$–$C_4$ alkyl;
R₁ is H, F, Cl, Br, CH₃, CF₃ or OCH₃;
R₂ is H, CH₃, C₂H₅, Cl or Br;
R₃ is H, CH₃, C₂H₅, Cl, Br, OCH₃, OC₂H₅ or SCH₃;
R₄ is H or $C_1$–$C_4$ alkyl;
R₅ is H, CH₃, C₂H₅, Cl, Br, OCH₃, OC₂H₅ or SCH₃;
R₆ is H, CH₃ or C₂H₅;
R₇ is H or $C_1$–$C_4$ alkyl;
R₁₂ is H or CH₃;
R₁₂' is H or CH₃;
R₁₃ is H or CH₃;
R₁₄ is H, CH₃, C₂H₅, Cl, OCH₃, OC₂H₅ or SCH₃;
R₁₅ is $C_1$–$C_3$ alkyl;
A is

[pyrimidine/triazine structure with X, Y, Z substituents]

X is CH₃, OCH₃ or Cl;
Y is CH₃, C₂H₅, CH₂OCH₃, OCH₃, OC₂H₅, CH(OCH₃)₂, NH₂, NHCH₃, N(CH₃)₂, OCH₂CH₂OCH₃, OCH₂CF₃, SCH₃, CF₃ or

[dioxolane CH structure]

Z is CH;
and their agriculturally suitable salts; provided that
(a) when R₂ is Cl or Br, then W is O or S;
(b) when X is Cl, then Y is OCH₃, OC₂H₅, NH₂, NHCH₃ or N(CH₃)₂;
(c) when W''' is S, then R₁₃ is H and Y is CH₃, OCH₃, C₂H₅, OC₂H₅, CH₂OCH₃, CH(OCH₃)₂ or

[dioxolane CH structure]

(d) when Q is

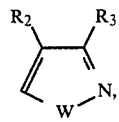

then one of $R_2$ or $R_3$ must be H, $CH_3$ or $C_2H_5$;
(e) when Q is

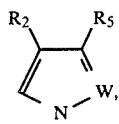

then one of $R_2$ or $R_5$ must be H, $CH_3$ or $C_2H_5$;
(f) the total number of carbon atoms of Q must be less than or equal to 8.

2. Compounds of claim 1 where R and $R_{15}$ are independently $CH_3$ or $C_2H_5$; $R_2$, $R_3$, $R_4$, $R_5$, $R_6$, $R_7$ and $R_{14}$ are independently H or $CH_3$; and W" is O.

3. Compounds of claim 2 where $R_1$ and $R_{13}$ are H.

4. Compounds of claim 3 where Y is $CH_3$, $CH_2OCH_3$, $OCH_3$, $OC_2H_5$, $CH(OCH_3)_2$ or

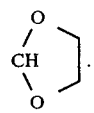

5. Compounds of claim 4 where

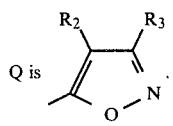

6. Compounds of claim 4 where

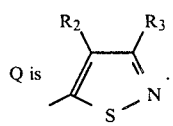

7. Compounds of claim 4 where

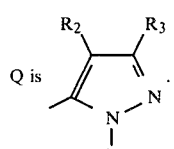

8. Compounds of claim 4 where

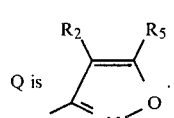

9. Compounds of claim 4 where

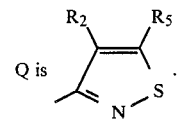

10. Compounds of claim 4 where

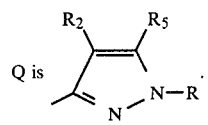

11. Compounds of claim 4 where

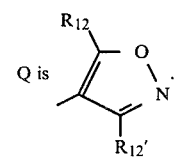

12. Compounds of claim 4 where

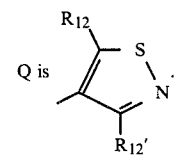

13. Compounds of claim 4 where

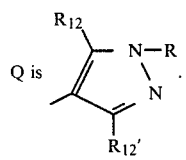

14. Compounds of claim 4 where

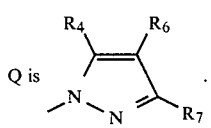

15. Compounds of claim 4 where

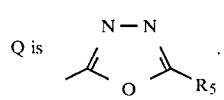

16. Compounds of claim 4 where

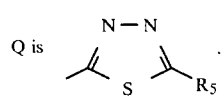

17. Compounds of claim 4 where

18. Compounds of claim 4 where Q is 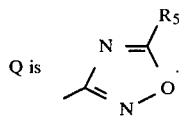

19. Compounds of claim 4 where Q is 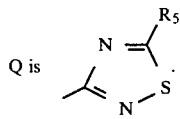

20. Compounds of claim 4 where Q is 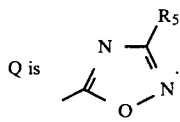

21. Compounds of claim 4 where Q is 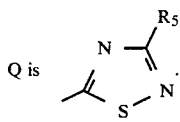

22. Compounds of claim 4 where Q is 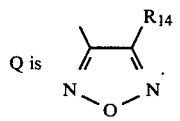

23. Compounds of claim 4 where Q is 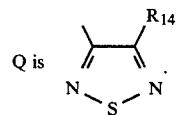

24. Compounds of claim 4 where Q is 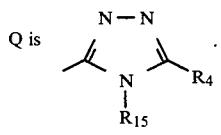

25. Compounds of claim 4 where Q is 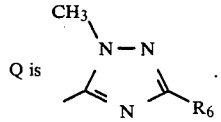

26. Compounds of claim 4 where Q is 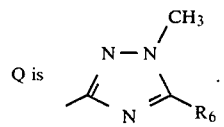

27. Compounds of claim 4 where Q is 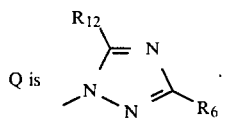

28. Compounds of claim 4 where Q is 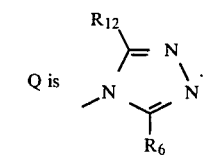

29. Compounds of claim 4 where Q is 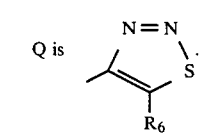

30. Compounds of claim 4 where Q is 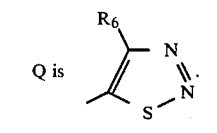

30. A compound of claim 1 selected from the group consisting of 2-(isoxazol-5-yl)-N-[(4,6-dimethoxypyrimidin-2-yl)aminocarbonyl]benzenesulfonamide 2-(isoxazol-5-yl)-N-[(4-methoxy-6-methylpyrimidin-2-yl)aminocarbonyl]benzenesulfonamide; N-[(4,6-dimethoxypyrimidin-2-yl)aminocarbonyl]-2-(1- and/or 2-methyl-1H-pyrazol-3-yl)benzenesulfonamide;

N-[(4,6-dimethoxypyrimidin-2-yl)aminocarbonyl]-2-(1-methyl-1H-pyrazol-4-yl)benzenesulfonamide; N-[(4,6-dimethoxypyrimidin-2-yl)aminocarbonyl]-2-(isoxazol-4-yl)benzenesulfonamide; and 2-(isoxazol-4-yl)-N-[(4-methoxy-6-methylpyrimidin-2-yl)aminocarbonyl]-benzenesulfonamide.

31. A composition suitable for controlling the growth of undesired vegetation which comprises an effective amount of a compound of claim 1 and at least one of the following: surfactant, solid or liquid diluent.

32. A composition suitable for controlling the growth of undesired vegetation which comprises an effective amount of a compound of claim 2 and at least one of the following: surfactant, solid or liquid diluent.

33. A composition suitable for controlling the growth of undesired vegetation which comprises an effective amount of a compound of claim 3 and at least one of the following: surfactant, solid or liquid diluent.

34. A composition suitable for controlling the growth of undesired vegetation which comprises an effective amount of a compound of claim 4 and at least one of the following: surfactant, solid or liquid diluent.

35. A method for controlling the growth of undesired vegetation which comprises applying to the locus to be protected an effective amount of a compound of claim 1.

36. A method for controlling the growth of undesired vegetation which comprises applying to the locus to be protected an effective amount of a compound of claim 2.

37. A method for controlling the growth of undesired vegetation which comprises applying to the locus to be protected an effective amount of a compound of claim 3.

38. A method for controlling the growth of undesired vegetation which comprises applying to the locus to be protected an effective amount of a compound of claim 4.

39. A compound of claim 1 which is N-[(4-methoxy-6-methylpyrimidin-2-yl)aminocarbonyl]-2-(1,2,3-thiadiazol-4-yl)benzenesulfonamide.

* * * * *